US009974478B1

(12) United States Patent
Brokaw et al.

(10) Patent No.: US 9,974,478 B1
(45) Date of Patent: May 22, 2018

(54) DISCREET MOVEMENT MEASUREMENT AND CUEING SYSTEM FOR IMPROVEMENT OF SAFETY AND EFFICACY OF MOVEMENT

(71) Applicants: Elizabeth Brokaw, Great Falls, VA (US); Dustin A. Heldman, Shaker Heights, OH (US); Christopher L. Pulliam, Shaker Heights, OH (US); Joseph P. Giuffrida, Hinckley, OH (US)

(72) Inventors: Elizabeth Brokaw, Great Falls, VA (US); Dustin A. Heldman, Shaker Heights, OH (US); Christopher L. Pulliam, Shaker Heights, OH (US); Joseph P. Giuffrida, Hinckley, OH (US)

(73) Assignee: Great Lakes NeuroTechnologies Inc., Cleveland, OH (US)

(*) Notice: Subject to any disclaimer, the term of this patent is extended or adjusted under 35 U.S.C. 154(b) by 127 days.

(21) Appl. No.: 14/576,581

(22) Filed: Dec. 19, 2014

(51) Int. Cl.
*A61B 5/103* (2006.01)
*A61B 5/117* (2016.01)
(Continued)

(52) U.S. Cl.
CPC .............. *A61B 5/486* (2013.01); *A61B 5/112* (2013.01); *A61B 5/1117* (2013.01);
(Continued)

(58) Field of Classification Search
CPC ....... A61B 5/486; A61B 5/1117; A61B 5/112; A61B 5/1124; A61B 5/4023;
(Continued)

(56) References Cited

U.S. PATENT DOCUMENTS 5,919,149 A * 7/1999 Allum .................. A61B 5/1116
600/595
7,369,896 B2 5/2008 Gesotti
(Continued)

OTHER PUBLICATIONS

Lewek et al. "The Relationship Between Spatiotemporal Gait Asymmetry and Balance in Individuals with Chronic Stroke", Journal of Applied Biomechanics, vol. 30, Issue 1, 2014, pp. 31-36.*

(Continued)

*Primary Examiner* — Devin Henson
(74) *Attorney, Agent, or Firm* — Brian Kolkowski

(57) ABSTRACT

The present invention relates to systems and methods for helping subjects improve safety and efficiency of their movements; particularly subjects who have suffered an injury or suffer from a movement or other such disorder. More particularly, the present invention relates to such a system and method for monitoring a subject's movement to detect or predict unsafe, undesirable, or impaired movements, or symptoms of movement disorders, and also a system for providing possible treatment methods for such conditions. The present invention further relates to a method and system of providing cues or stimuli to the subject when such unsafe or undesirable movements, instabilities or symptoms are detected or predicted. Most particularly, the present invention relates to a subject-customized and adaptive movement recovery system, and method of providing therapy and training to improve functional motor recovery and safety of movement of a subject suffering from an injury or from movement disorder(s).

14 Claims, 43 Drawing Sheets

(51) Int. Cl.
A61B 5/00 (2006.01)
A61B 5/11 (2006.01)
(52) U.S. Cl.
CPC .......... *A61B 5/4023* (2013.01); *A61B 5/4082* (2013.01); *A61B 5/6803* (2013.01); *A61B 5/6898* (2013.01); *A61B 5/7275* (2013.01); *A61B 5/7282* (2013.01); *A61B 5/7405* (2013.01); *A61B 5/7455* (2013.01); *A61B 5/1124* (2013.01); *A61B 5/6823* (2013.01); *A61B 5/6824* (2013.01); *A61B 5/7415* (2013.01)
(58) Field of Classification Search
CPC ... A61B 5/4082; A61B 5/6898; A61B 5/7275; A61B 5/7405; A61B 5/7415; A61B 5/7455; A61B 5/6824; A61B 5/6823
See application file for complete search history.

(56) References Cited

U.S. PATENT DOCUMENTS

| | | | |
|---|---|---|---|
| 8,409,116 B2 | 4/2013 | Wang et al. | |
| 8,436,737 B1* | 5/2013 | Trout | A61B 5/1116 340/573.1 |
| 8,554,325 B2 | 10/2013 | Molnar et al. | |
| 8,928,484 B2* | 1/2015 | Chang | A61B 5/0002 340/573.1 |
| 2008/0140137 A1* | 6/2008 | Wall, III | A61B 5/1036 607/2 |
| 2008/0281550 A1* | 11/2008 | Hogle | A61B 5/1038 702/127 |
| 2012/0101411 A1* | 4/2012 | Hausdorff | A61B 5/1117 600/595 |
| 2012/0277891 A1* | 11/2012 | Aragones | G06F 19/3481 700/91 |
| 2014/0276242 A1* | 9/2014 | Chen | A61B 5/112 600/595 |
| 2015/0018724 A1* | 1/2015 | Hsu | A61B 5/1116 600/595 |
| 2015/0164377 A1* | 6/2015 | Nathan | A61B 5/1122 600/595 |
| 2017/0004685 A1* | 1/2017 | Karsten | G06F 19/322 |

OTHER PUBLICATIONS

Inge Lim, Rehabilitation in Parkinson's disease: strategies for cueing, May 19, 2009.

A Nieuwboer et al. Cueing training in the home improves gait-related mobility in Parkinson's disease: the RESCUE trial, J Neurol Neurosurg Psychiatry 2007, vol. 78, pp. 134-140.

Charles T. Merbitz et al., Cueing and Logical Problem Solving in Brain Trauma Rehabilitation: Frequency in Patterns Clinician and Patient Behaviors, European Journal of Behavior Analysis 2003, vol. 4, pp. 45-58.

* cited by examiner

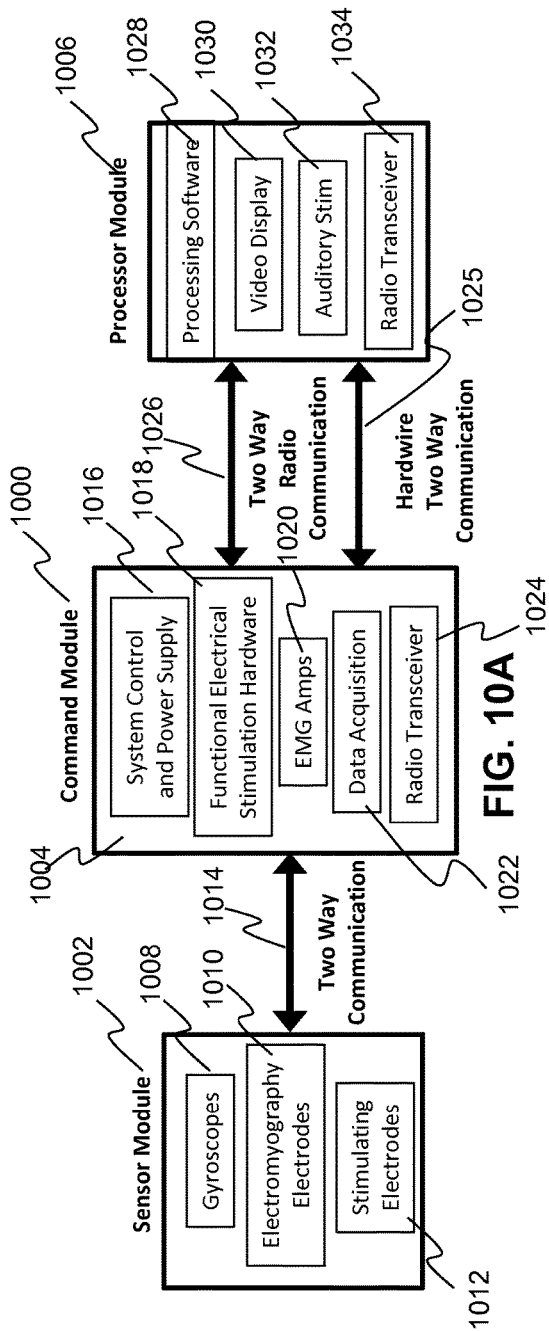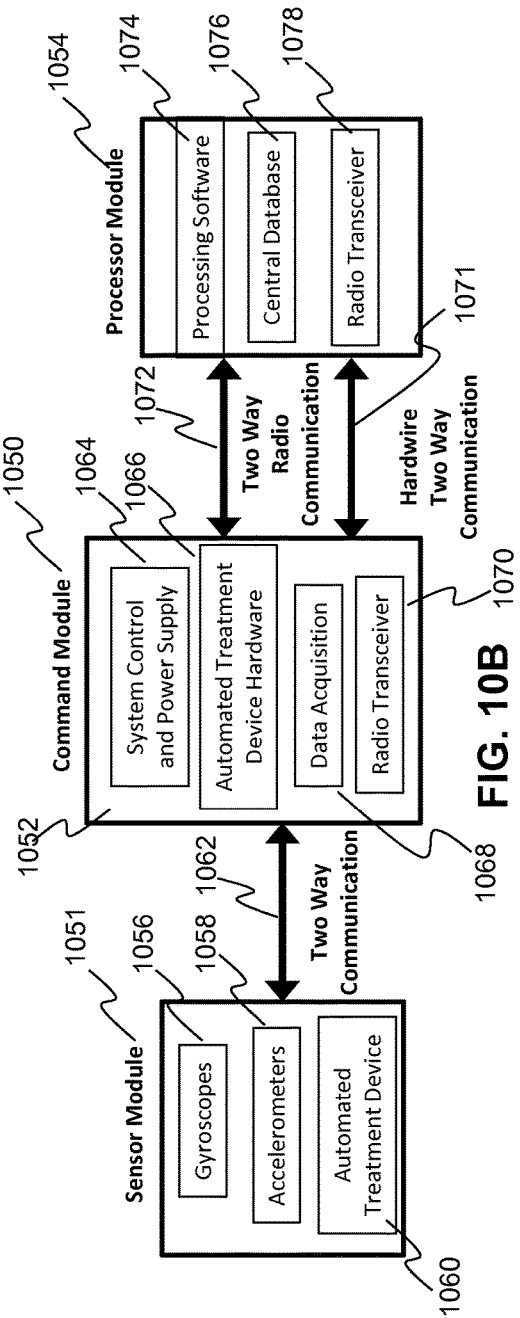

DISCREET MOVEMENT MEASUREMENT AND CUEING SYSTEM FOR IMPROVEMENT OF SAFETY AND EFFICACY OF MOVEMENT

BACKGROUND OF THE INVENTION

1. Field of the Invention

The present invention relates to a system and method for helping subjects improve the safety and efficiency of their movements. More particularly, the present invention relates to improving safety and efficiency of movement of subject's who have suffered an injury or suffer from a movement or other such disorders. More particularly, the present invention relates to such a system and method for monitoring a subject's movement to detect or predict unsafe or undesirable movements, instabilities and/or symptoms of movement disorders and also a system for providing cueing the subject to adjust for such conditions. The present invention further relates to a method and system of providing cues, warnings, messages or otherwise communicating to the subject when such unsafe or undesirable movements, instabilities or symptoms are detected or predicted. Most particularly, the present invention relates to a subject-customized and adaptive movement recovery system, and method of providing therapy and training with the goal of improving functional motor recovery and safety and stability of movement of a subject suffering from an injury or from a movement disorder.

2. Technology Review

Movement disorders and unsafe, undesirable or unstable movement, including those resulting from brain or spinal cord injury, or abnormalities affect millions of individuals worldwide. These movement disorders and unsafe, undesirable or unstable movements can be the result of traumatic brain injury (TBI), stroke, cerebral palsy (CP), Parkinson's disease (PD) and Parkinsonism, dystonia, chorea, Huntington's disease, ataxia, the many varieties of tremor, myoclonus, tics, Tourette's syndrome, restless leg syndrome, gait disorders, balance disorders, other movement disorders, and the like. Since these injuries or abnormalities can affect most parts of the brain or the spinal cord, the possible results are numerous. Effects can include instability, motor paralysis, sensory disturbances, language difficulties, memory problems, tremor, issues with swallowing or slurred speech. These disorders can also result in loss of motor control of the individual's extremities, including paralysis or weakness, abnormal muscle tone, abnormal posture, abnormal movement synergies and loss of coordination. Many individuals that experience a movement disorder develop a physical disability that affects activities of daily living including eating, dressing and personal hygiene.

Further, more specifically with regard to recovery from stroke, independent mobility has a large influence on quality of life, and locomotor function is an important component of disability, especially with respect to the level of disability as perceived by the subject. Stroke affects over 700,000 individuals each year in the United States and commonly results in long term gait impairment. Normal walking is a primary recovery goal after stroke and, while approximately 55% of individuals recover at least partial mobility independence, walking kinematics are commonly impaired by weakness and abnormal muscle synergies. The commonly occurring abnormal extensor synergy results in difficulty with hip, knee, and ankle flexion. As a result, individuals compensate using hip hiking, hip circumduction, shuffled gait, and other such compensatory movements that can be unsafe, undesirable or create instabilities. This disruption of normal kinematics results in asymmetrical gait, decreased walking speed, and decreased endurance. In fact, 60-80% of individuals that achieve ambulation after stroke walk with greatly reduced efficiency and at a speed that is insufficient for community ambulation.

Persons suffering from unsafe, undesirable or unstable movement are much more susceptible to falling, and injuries resulting therefrom. There are presently many fall detection systems on the market that are designed to detect falls after they have occurred, and such systems tends to exhibit a high degree of sensitivity and specificity for their detection in research, clinical or laboratory settings, but this does not correlate to success in real-world situations (i.e., during activities of daily living, outside of the clinical or laboratory setting) due to a high rate of false alarms or false positive detections. Such after-the-fact fall detection systems further exhibit limitations in usability, and raise privacy concerns, which could result in reduced acceptance of such fall detection systems. Wearable devices, mainly accelerometer based, have shown promise in this field; however, there are no wearable systems currently available to decrease unsafe or undesirable movement and instability and reduce the risk of falling through cueing.

Focused interventions are effective for recovery of normal gait. Research studies on rehabilitative interventions, including electrical stimulation and treadmill training, have shown that task-specific practice and use of auditory pacing cues have the greatest efficacy for improving coordination and overall gait. Unfortunately insurance reimbursable therapy time is limited and clinicians often need to focus on tasks such as fall recovery and transfer safety, and are unable to dedicate time to improving gait coordination patterns. Additionally, compliance with prescribed home exercise is generally low. Home-based technology paired with in-clinic therapy could improve compliance and encourage improved gait techniques, thus increasing recovery and improving the quality and safety of subject movement.

While a wide range of technologies have been developed to assist with mobility, such as walkers, orthotics, and electrical stimulation devices, significant limitations to mobility remain due to inefficiency of gait patterns after stroke and limitations to the technologies. While wearable home-based assistive devices exist to improve mobility (ex. Bioness L300, ankle foot orthoses), these generally focus on impairment compensation, not recovery. Walk-mate is an in-clinic rhythmic auditory cueing device for gait recovery after stroke which has had positive results in improving gait symmetry, but while results with the Walk-mate show promise for wearable cueing devices to improve gait parameters, the rhythmic auditory cueing it employs is not feasible during general activity where gait speed and duration vary based on numerous environmental and other uncontrolled conditions. Additionally, the use of repetitive auditory cueing such as the Walk-mate utilizes, while acceptable and comfortable to use in a clinical or lab setting, in the community would likely result in social stigma leading to nonuse by the subject.

Additionally, in the United States it is estimated that over 270,000 individuals are hospitalized each year for a traumatic brain injury (TBI) and survive. Additionally, over one million individuals are treated for TBI and released from an emergency department without hospital admission. While traumatic brain injury can result in a wide variety of cognitive and motor impairments, balance impairment is one of the most commonly reported symptoms. Studies have shown balance impairments in a range of 32% to 65% of individuals after mild to moderate TBI, and impaired balance is the most commonly reported impairment that remains ten years post injury. While individuals with mild brain injury typically resolve symptoms within three months, complaints of balance and cognitive impairment can persist long after even mild brain injury with one study reporting that between 10% and 15% of individuals are still symptomatic a year after mild traumatic brain injury. Studies have shown that individuals with TBI tend to have increased postural sway and slower weight shifting response, which makes it harder to recover from balance disturbances. Traumatic brain injury also commonly results in impaired perception of impairments, decreased safety awareness, impaired impulse control, and impaired ability to multitask. Cueing is a commonly used technique during many facets of traumatic brain injury rehabilitation. During therapy, clinicians provide cues when their client's balance by visual observation becomes unstable. These cues focus the individual's attention on balance and away from secondary tasks. After a balance cue the individual concentrates on stabilizing their body to prevent a potential fall. These cues also help to increase the individual's awareness of their balance impairment by pointing out periods of instability. While cueing is commonly used during therapy, individuals currently do not have a way to independently obtain this type of feedback in their home and community.

The ability to evaluate balance, gait, and posture in the home and community is important for understanding how impairment affects daily activity. While research with activity monitors to assess individuals after stroke has shown good results, activity level alone is not sufficient to understand the cause of gait limitations. Sensor technology, such as described in U.S. Pat. No. 8,187,20, hereby incorporated by reference, has been able to capture clinically meaningful kinematic measures with high correlation to clinician scores and the ability to quantify deep brain stimulation response during the Unified Parkinson's Disease Rating Scale gait and balance tasks. Additionally researchers have in a limited way used accelerometers and gyroscopes successfully to evaluate balance, gait and posture, and to identify gait features in unimpaired and impaired individuals with some degree of correlation to measurements such as those captured with systems such as those that capture motion. Such sensors have also, in a limited way, evaluated gait impairment due to for example dropped foot after stroke. Additionally other researchers have demonstrated some degree of correlations between accelerometer based measurements and the Berg Balance Scale and Timed Up and Go clinical scores. The real-time, highly accurate evaluation of gait, balance and posture would be desirable to allow for cueing in the home and community that could reduce the risk of falls and help improve recovery. While cueing may not be able to completely replace assistive devices (e.g., walkers) for individuals with severe gait, balance and posture impairments during community ambulation, there is a need for a balance and stability cueing device that could increase the independence of a large subset of the stroke, TBI and movement disorder populations, and potentially increase gait, balance and posture awareness when used in conjunction with other forms of assistive technology.

Aside from, or in addition to, assistive modalities for helping improve therapy and outcomes of therapy, various other treatment methods exist for treating injuries and symptoms of diseases or disorder. Such other modalities may be used along with the proposed therapy improvement systems and methods to further increase the recovery and improvement time for certain subject. With respect to providing assistance in therapy or recovery, or in treating injuries or movement disorders that can lead to impairment of movement, there numerous methods or modalities, two of which include electrical stimulation, particularly deep brain stimulation (DBS) and functional electrical stimulation (FES), and the use of pharmaceutical treatments (i.e., medications, drugs). The effectiveness of both electrical stimulation and pharmaceutical treatment vary widely depending on a subject's individual impairments or symptoms and the causes thereof. Furthermore, the efficacy of each treatment or therapy method generally varies greatly throughout the day, as well as the life of the treatment due to numerous environmental and circumstantial factors that play a role in the severity of such symptoms such as spasticity.

It is therefore an object of the present invention to provide a system and method for treatment and therapy for individuals with movement impairment and disorders without needing a clinician to apply the treatment. It is still another object of the present invention to provide a system, which provides functional recovery. It is yet another object of the present invention to provide systems and methods for providing therapy to a subject to help improve recovery from stroke and TBI, as well as other injuries, diseases and disorders. It is further an object of the present invention to provide such systems and methods that can be worn or utilized by subjects while performing activities of daily living at home or in the community. It is still a further object of the present invention to provide such systems and methods that provide cues and more preferably subtle cues to the subject to help guide and focus the subject's attention to his or her movement and therapy in an inconspicuous manner that allows the subject to correct or otherwise address unsafe or undesirable movements, instability or symptoms in a manner that draws minimal attention to the subject and his or her therapy and training, thus avoiding social stigma.

SUMMARY OF THE INVENTION

The present invention relates to a system and method for helping subjects improve the safety and efficiency of their movements. More particularly, the present invention relates to improving safety and efficiency of movement of subject's who have suffered an injury, or who suffer from a movement or other such disorder. Still more particularly, the present invention relates to such a system and method for monitoring a subject's movement to detect or predict unsafe or undesirable movements, instabilities and/or symptoms of movement disorders, and in some embodiments also a system for providing possible treatment methods for such conditions. The present invention further relates to a method and system of providing cues, stimuli, warnings, messages or otherwise communicating to the subject when such unsafe or undesirable movements, instabilities or symptoms are detected or predicted. Most particularly, the present invention relates to a subject-customized and adaptive movement warning and recovery system, and method of providing therapy and training with the goal of improving the functional motor recovery and safety and stability of movement of a subject suffering from an injury or from a movement disorder.

The system of the present invention is preferably designed to be portable, small, lightweight, and capable of inconspicuous use by the subject. The system will utilize small wearable sensors or a device with sensors and include real-time kinematic analysis of movement characteristics during activities of daily living (ADL). The system further includes a component, device or system for providing cues to the subject based on detected or predicted impairment, unsafe or undesirable movement, instability, or movement disorder symptoms. The cues referred to in the present invention are designed alert the subject to the particular unsafe or undesirable movement, instability or symptom in order to draw the subject's focus and attention to the condition, and allow the subject to take corrective or preventative measures to change his or her movement or motion. Such cues thus aim to train the subject to be aware of unsafe or undesirable movements, instabilities or symptoms, and thus to improve the overall safety and quality of the subject's movement by increasing the awareness and attention to particular unsafe or undesirable movements or conditions of which the subject suffers.

While cues provided by clinicians during therapy sessions in the clinic are an effective means of providing therapy, training and awareness regarding movement, balance, posture or other impairments, there are currently no systems that provide such cueing outside of the clinical or laboratory setting, or in a clinic or laboratory setting with the objective, quantifiable review of a subject's movement, posture, balance, and/or stability. The systems of the present invention include the cueing device or mechanism in order to provide cueing capabilities preferably outside of the clinical or lab setting, but also inside, for subject's use while performing activities of daily living, rehabilitation, therapy, and the like. One example of a cueing mechanism for such use is a small vibrational motor to provide cues, such as at a similar magnitude and frequency to those used in silent mode for cellular phones. These cues will be provided by the cueing device or component at the initial detection of unsafe or undesirable movement or instability to improve movement quality and/or balance.

In order to provide cues in an intelligent, useful and meaningful manner based on the subject's measured movement, the system further included intelligent algorithms developed to recognize impaired gait, balance, posture and movement patterns and to trigger those cues to correct, prevent or otherwise address the behavior. For purposes of this invention, the ability to recognize and measure impaired gait, balance, posture, and movement patterns is intended to include impairments, disorders and unsafe or undesired motion of any portion of the body, including lower extremities, upper extremities, truck, head, and each of the constituent body parts thereof. Various stages of algorithms may be utilized with the present invention. A first stage of algorithms may preferably detect, in real-time, when abnormal gait, balance, posture or movement events, and the like occur by extracting various kinematic features (e.g., hip circumduction, gait asymmetry, trunk orientation, postural sway) in real-time. A second stage of algorithms may adaptively modulate and trigger cueing in response to abnormal gait, balance, posture and movement patterns. Hysteresis techniques may be utilized to minimize antagonistic cueing and maximize encouragement. Further, cues, as determined and produced by the invention's intelligent algorithms, will adapt and change according to the subject's condition. For example, the algorithms may control changes in the cues based on continuing movement measurement such that the cues may get progressively longer in duration with prolonged poor kinematics as measured by the system. The system may include user interface capabilities allowing subjects the ability to choose cue magnitudes and preferences, auditory, vibrational, visual and switch between them depending on the situation (e.g., vibrational in public and auditory at home).

Key physical design features of the devices of the present invention, namely the small, portable and wearable device and the mechanisms for providing private cues or stimuli, allow the systems of the present invention to be inconspicuously worn continuously throughout the day without attracting attention that could lead to social stigma, which is known to discourage community use and increase rates of abandonment of assistive technology for mobility. This type of low interference assistive technology could significantly increase use and encourage further community integration of individuals with gait, balance, posture and movement impairments. The wearable nature of the devices of the present invention makes it preferable to commonly used tools for quantitative balance and/or movement assessment such as force plates and gait mats, which are fixed location devices that cannot be used during activities of daily life. While accelerometers can be comparable to force plate measurements, for example with respect to balance, with positive results and good correlation with clinical measures of balance, these sensors have not typically been used for continuous home evaluation of balance. The present invention's ability to detect and record unsafe or undesirable movement or instability could be beneficial for the assessment of gait, balance, posture and movement issues, for example fall risk, during activities of daily living and to evaluate changes from a therapeutic intervention.

As noted, many embodiments of the present invention will utilize wearable sensors and, in certain embodiments, processors or processing devices. Examples of such processor or processing devices include smart phones, personal digital assistants (PDAs), laptop computers, tablet computers, personal electronic accessory devices such as watches, headphones, or the like, standalone processing devices designed specifically for use with applications of the present invention, personal fitness monitors, or the like, each embodiment including or being able to have coordinated application(s), program(s) or software installed in order to perform the analysis. The present invention preferably involves leveraging and adapting these technologies in an integrated platform with unique features to improve gait, balance, posture and movement in general or resulting from a movement disorder or disease, but also after injury (such as TBI or stroke)—a process and concept not currently known or utilized in the art. The system components provide a low-cost, portable platform that integrates sensing movement (e.g., gait patterns) and delivering cues from either or both the processor/interface/device (e.g., smart phone and associated application) and sensor(s) lends itself to many rehab and research markets stroke and TBI recovery and therapy or treatment of such injuries as well as movement disorders. The cueing device in some embodiments will provide sensory cueing (e.g., auditory or tactile vibrational) while the subject performs activities of daily living, which commonly plays an important role and has shown success in in-clinic therapy. The small wearable profile and sensory cueing will allow the system of the present invention to be worn under clothing during the day without attracting attention that could lead to social stigma, known to discourage community use and increase abandonment of assistive technology.

The system of the present invention, and use thereof, will improve movement kinematics resulting in improved safety and efficiency, reduced fall risk, improved therapy and training after injury, and increased community integration for individuals who suffer from movement disorders, movement or posture impairment, or other similar or related issues or conditions. The potential societal benefits of the present invention include increased community integration of individuals with gait, balance, posture or other movement impairment (such as from stroke, TBI or other movement disorders), increased or improved rehabilitation and the reduced incidence of injuries resulting from unsafe or undesirable movement in such populations. Improvements to gait, balance, posture, and other movements could increase community ambulation and improve overall health outcomes for individuals suffering such injuries, disorders and diseases. Additionally, the present invention has potential implications for improving evaluation of fall risk, a more specific form of balance or stability impairment. The system of the present invention could potentially help those with injuries or disorders or the aging population to better assess their risk of falling and take the necessary precautions to reduce the risk of injury. Further, the system is not merely a tool for those with existing injuries or impairments or who are at a higher risk for falls, but rather can be used as an ongoing assessment tool for those who are more susceptible to such injuries or impairments (e.g., the elderly), or even those subjects who merely wish to track their movement to ensure it is in safe ranges (e.g., athletes). The system can further actively engage clinicians and their clients to maximize recovery by integrating with conventional therapy and increasing carryover into daily life. As healthcare reimbursement models move toward accountable care organizations, technologies like the present invention will play an important role in increasing independent therapy, training and recovery, which will reduce impaired or symptomatic movement and improve overall health resulting in reduced hospital readmission. Additionally, the present invention will increase the quality and frequency of feedback provided to clinicians to improve mobility outcomes for individuals who are unable to receive routine therapy due to geographic or socio-economic limitations.

In enabling these numerous applications and uses, several key innovations of the present invention include integration of movement or motion sensing and predictive or preventative cueing; integration of therapy, training and care with activities of daily living to improve recovery from stroke, TBI or other injury, disorder or disease and to improve gait, balance, posture and movement; the system's ability to cue the wearer at the first sign of instability, unsafe, undesirable, or impaired movement or motion to increase focus on gait, balance, posture or movement. The features of the device, specifically the inconspicuous device design, subtle cueing mechanism and intelligent algorithms capable of providing real-time assessment of the subject's movement to provide the cues all combine to allow the system to help reduce the risk of social stigma that is common to assistive technology for gait, balance, posture, and movement while recording and evaluating instances of instability or unsafe or undesirable movement during activities of daily living, which could help assess overall safety and efficiency of movement and help individuals identify high risk activities, while also providing targeted technology to improve accessibility, compliance and engagement with care, therapy and training.

The application may also be used to review performance metrics and suggest additional therapy, training or home exercises that could further improve gait, balance, posture, or other movement. For example, if a subject utilized the hip circumduction pattern of gait, then stretching and muscle relaxation exercises might be recommended to reduce the effects of abnormal synergies and spasticity. Additionally, if asymmetry in limb swing speed is detected the application could suggest thinking about an upbeat song to try to keep rhythm. Collected data can be pushed to cloud based storage, central database(s) or remote locations where a clinician, physician, therapist or technician can monitor compliance or adjust cueing or exercise protocols using a web-based application or other communication method.

Still another important aspect of the present invention is the use of targeted technology to improve access to care. The present invention will expand use of techniques practiced during in-clinic therapy to improve gait, balance, posture and movement kinematics and carryover into daily activity, effectively increasing the effectiveness of in-clinic therapy time. Additionally, cloud-based connectivity of client performance and compliance data through mobile technology will improve clinician accessibility to client data through web applications. While one-on-one in-clinic therapy where clinicians provide key discussion of techniques to improve movement quality is essential, the present invention increases access for both geographic and socio-economic disparate populations. Individuals that live far from physicians, clinicians or therapists, or who cannot afford frequent visits, may only be able to receive in-clinic therapy on a very sporadic and intermittent basis. The technology of the present invention may increase the amount of time in training and feedback from therapists between sessions, benefitting underserved populations.

Still further, clinical innovation lies in the seamless integration between therapeutic intervention and daily activities to improve mobility outcomes for individuals suffering or recovering from injury or movement disorders. Combining the present invention with conventional therapy may increase the rate and extent of mobility recovery and therapeutic success. In addition to the cueing and therapy and training functions, the present invention may provide a motivational interface to encourage individuals to hit activity and kinematics goals between therapy sessions and to overcome the potential for lack of motivation that often hinders recovery, therapy and training. The cumulative effect of the cues and engagement with the clinician provided by the present invention will have a significant impact on effectiveness of therapy sessions and overall gait, balance, posture and movement improvement. Long-term data from the present invention will provide clinicians with an important view of the subject's home and community mobility. In some embodiments, clinicians will be able to view the subject's status, modify suggested exercises and goals, and track recovery. Additionally, this information could be beneficial for management of other treatments.

Some embodiments of present invention may provide for a system and method that can provide assistive backup treatment or therapy to the subject to supplement cueing effects, which may be insufficient to completely address the impairment at the subject's stage of therapy. In such embodiments, the present invention may manage electrical stimulation treatment, such as functional electrical stimulation (FES) or deep brain stimulation (DBS) systems, and determine subject customized electrical stimulation parameters such as amplitude, current, frequency, pulse width, and activation timing by utilizing accelerometric, gyroscopic or other movement related information, such as electromyography (EMG) data, or the like, and/or a central database, or system of databases, of subject and treatment histories. In other embodiments, the system and method may manage the titration, dosing and/or delivery of a medication, such as Baclofen pump dosing for lower extremity spasticity, or drug taken by the subject or when using an infusion or other medication pump system and provide for pharmaceutical parameters such as drug titrations, doses and times. Optionally, the present invention includes but is not limited to compliance, task time spent, muscle coordination and functional improvement by utilizing kinetic, gyroscopic or other movement related information, and/or electromyography (EMG) data. Many embodiments of the present invention further includes a system and methods of storing and cataloging the movement related information and subject specific treatments in a central database system to be used for continuous improvement of the treatment protocols for use with subjects in the future.

A number of embodiments of the present invention are envisioned in this disclosure. These embodiments are examples of the many embodiments encompassed by the present invention, but do not in any way limit the many other embodiments covered by this disclosure.

One embodiment of the present invention includes a method of providing rehabilitation and training or improving quality and safety of a subject's movement comprising steps of providing a portable therapy system or device to the subject, portable therapy system or device comprising at least one sensor having a signal related to the subject's movement, a processor comprising an algorithm and an output, and a cueing or stimulus device, measuring the subject's movement with the at least one sensor substantially continuously to acquire movement data, analyzing the movement data with the processor and algorithm to predict or detect the occurrence of at least one of gait, balance or posture impairment or a symptom of a movement disorder, transmitting the output of the algorithm to a cueing or stimulus device, and providing with the cueing or stimulus device a cue or stimulus to the subject based on the prediction or detection, wherein the cue or stimulus notifies the subject of the prediction or detection and allows the subject to react accordingly to prevent or correct the predicted or detected at least one of gait, balance or posture impairment or symptom of a movement disorder.

Another embodiment of the present invention includes a method of rehabilitation and training a subject or improving quality and safety of movement comprising steps of providing a portable therapy system or device to the subject, portable therapy system or device comprising at least one sensor having a signal related to the subject's balance or stability, a processor comprising an algorithm and an output, and a cueing or stimulus device, measuring the subject's balance or stability with the at least one sensor substantially continuously to acquire movement data, analyzing the movement data with the processor and algorithm to predict or detect imbalance or instability of the subject, transmitting the output of the algorithm to a cueing or stimulus device, and providing with the cueing or stimulus device a cue or stimulus to the subject based on the prediction or detection, wherein the cue or stimulus notifies the subject of the prediction or detection and allows the subject to react accordingly to prevent or correct the predicted or detected imbalance or instability.

Yet another embodiment of the present invention includes a method of rehabilitation and training a subject or improving quality and safety of movement comprising steps of providing a portable therapy system or device to the subject, portable therapy system or device comprising at least one sensor having a signal related to the subject's movement, a processor comprising an algorithm and an output, and a cueing or stimulus device, measuring the subject's movement with the at least one sensor substantially continuously to acquire movement data, analyzing the movement data with the processor and algorithm to predict or detect unsafe or undesirable movement of the subject, transmitting the output of the algorithm to a cueing or stimulus device, and providing with the cueing or stimulus device a cue or stimulus to the subject based on the prediction or detection, wherein the cue or stimulus notifies the subject of the prediction or detection and allows the subject to react accordingly to prevent or correct the predicted or detected unsafe or undesirable movement.

Still another embodiment of the present invention includes a method of providing rehabilitation and training or improving quality and safety of a subject's movement comprising steps of providing a portable therapy system or device to the subject, portable therapy system or device comprising at least one sensor having a signal related to the subject's movement, a processor comprising an algorithm and an output, and a cueing or stimulus device, measuring the subject's movement with the at least one sensor substantially continuously to acquire movement data, analyzing the movement data with the processor and algorithm to predict or detect the occurrence of at least one of gait, balance or posture impairment or a symptom of a movement disorder, transmitting the output of the algorithm to a cueing or stimulus device, providing with the cueing or stimulus device a cue or stimulus to the subject based on the prediction or detection, and providing treatment, therapy or assistance to the subject with a treatment or therapy device, wherein the cue or stimulus notifies the subject of the prediction or detection and allows the subject to react accordingly to prevent or correct the predicted or detected at least one of gait, balance or posture impairment or symptom of a movement disorder, and the treatment, therapy or assistance is provided based at least in part on a persisting or worsening predicted or detected gait, balance or posture impairment or movement disorder symptom.

Yet still another embodiment of the present invention includes a method of rehabilitation and training a subject or improving quality and safety of movement comprising steps of providing a portable therapy system or device to the subject, portable therapy system or device comprising at least one sensor having a signal related to the subject's balance or stability, a processor comprising an algorithm and an output, and a cueing or stimulus device, measuring the subject's balance or stability with the at least one sensor substantially continuously to acquire movement data, analyzing the movement data with the processor and algorithm to predict or detect imbalance or instability of the subject, transmitting the output of the algorithm to a cueing or stimulus device, providing with the cueing or stimulus device a cue or stimulus to the subject based on the prediction or detection, and providing treatment, therapy or assistance to the subject with a treatment or therapy device, wherein the cue or stimulus notifies the subject of the prediction or detection and allows the subject to react accordingly to prevent or correct the predicted or detected imbalance or instability, and the treatment, therapy or assistance is provided based at least in part on a persisting or worsening predicted or detected imbalance or instability.

Even still another embodiment of the present invention includes a method of rehabilitation and training a subject or improving quality and safety of movement comprising steps of providing a portable therapy system or device to the subject, portable therapy system or device comprising at least one sensor having a signal related to the subject's movement, a processor comprising an algorithm and an output, and a cueing or stimulus device, measuring the subject's movement with the at least one sensor substantially continuously to acquire movement data, analyzing the movement data with the processor and algorithm to predict or detect unsafe or undesirable movement of the subject, transmitting the output of the algorithm to a cueing or stimulus device, providing with the cueing or stimulus device a cue or stimulus to the subject based on the prediction or detection, and providing treatment, therapy or assistance to the subject with a treatment or therapy device, wherein the cue or stimulus notifies the subject of the prediction or detection and allows the subject to react accordingly to prevent or correct the predicted or detected unsafe or undesirable movement, and the treatment, therapy or assistance is provided based at least in part on a persisting or worsening predicted or detected unsafe or undesirable movement.

Still yet another embodiment of the present invention includes a portable therapy system or device for rehabilitation and training or to improve the quality and safety of a subject's movement comprising at least one sensor adapted to measure a subject's movement, the at least one sensor having a signal related to the subject's voluntary or involuntary movement, a processor comprising an algorithm adapted to predict or detect the occurrence of at least one of gait, balance or posture impairment or a symptom of a movement disorder and provide an output corresponding to the prediction or detection, and a cueing or stimulus device adapted to receive the output from the algorithm and provide at least one cue or stimulus to the subject based at least in part on the output of the algorithm, wherein the at least one cue or stimulus is adapted to notify the subject wearing the portable therapy system or device of the prediction or detection and allow the subject to react accordingly to prevent or correct the predicted or detected at least one of gait, balance or posture impairment or symptom of a movement disorder.

Even yet another embodiment of the present invention includes a portable therapy system or device for rehabilitation and training or to improve the quality and safety of a subject's movement comprising at least one sensor adapted to measure a subject's movement, the at least one sensor having a signal related to the subject's balance or stability, a processor comprising an algorithm adapted to predict or detect imbalance or instability of the subject and provide an output corresponding to the prediction or detection, and a cueing or stimulus device adapted to receive the output from the algorithm and provide at least one cue or stimulus to the subject based at least in part on the output of the algorithm, wherein the at least one cue or stimulus is adapted to notify the subject wearing the portable therapy system or device of the prediction or detection and allow the subject to react accordingly to prevent or correct the predicted or detected imbalance or instability.

Yet even another embodiment of the present invention includes a portable therapy system or device for rehabilitation and training or to improve the quality and safety of a subject's movement comprising at least one sensor adapted to measure a subject's movement, the at least one sensor having a signal related to the subject's voluntary or involuntary movement, a processor comprising an algorithm adapted to predict or detect unsafe or undesirable movement and provide an output corresponding to the prediction or detection, and a cueing or stimulus device adapted to receive the output from the algorithm and provide at least one cue or stimulus to the subject based at least in part on the output of the algorithm, wherein the at least one cue or stimulus is adapted to notify the subject wearing the portable therapy system or device of the prediction or detection and allow the subject to react accordingly to prevent or correct the predicted or detected unsafe or undesirable movement.

Still even another embodiment of the present invention includes a portable therapy system or device for rehabilitation and training or to improve the quality and safety of a subject's movement comprising at least one sensor adapted to measure a subject's movement, the at least one sensor having a signal related to the subject's voluntary or involuntary movement, a processor comprising an algorithm adapted to predict or detect the occurrence of at least one of gait, balance or posture impairment or a symptom of a movement disorder and provide an output corresponding to the prediction or detection, a cueing or stimulus device adapted to receive the output from the algorithm and provide at least one cue or stimulus to the subject based at least in part on the output of the algorithm, and a treatment, therapy or assistance device adapted to provide treatment, therapy or assistance beyond the cue or stimulus based on persisting or worsening gait, balance or posture impairment or movement disorder symptom, wherein the at least one cue or stimulus is adapted to notify the subject wearing the portable therapy system or device of the prediction or detection and allow the subject to react accordingly to prevent or correct the predicted or detected at least one of gait, balance or posture impairment or symptom of a movement disorder, and.

Even yet still another embodiment of the present invention includes a portable therapy system or device for rehabilitation and training or to improve the quality and safety of a subject's movement comprising at least one sensor adapted to measure a subject's movement, the at least one sensor having a signal related to the subject's balance or stability, a processor comprising an algorithm adapted to predict or detect imbalance or instability of the subject and provide an output corresponding to the prediction or detection, a cueing or stimulus device adapted to receive the output from the algorithm and provide at least one cue or stimulus to the subject based at least in part on the output of the algorithm, and a treatment, therapy or assistance device adapted to provide treatment, therapy or assistance beyond the cue or stimulus based on persisting or worsening imbalance or instability, wherein the at least one cue or stimulus is adapted to notify the subject wearing the portable therapy system or device of the prediction or detection and allow the subject to react accordingly to prevent or correct the predicted or detected imbalance or instability.

Yet even still another embodiment of the present invention includes a portable therapy system or device for rehabilitation and training or to improve the quality and safety of a subject's movement comprising at least one sensor adapted to measure a subject's movement, the at least one sensor having a signal related to the subject's voluntary or involuntary movement, a processor comprising an algorithm adapted to predict or detect unsafe or undesirable movement and provide an output corresponding to the prediction or detection, a cueing or stimulus device adapted to receive the output from the algorithm and provide at least one cue or stimulus to the subject based at least in part on the output of the algorithm, and a treatment, therapy or assistance device adapted to provide treatment, therapy or assistance beyond the cue or stimulus based on persisting or worsening unsafe or undesirable movement, wherein the at least one cue or stimulus is adapted to notify the subject wearing the portable therapy system or device of the prediction or detection and allow the subject to react accordingly to prevent or correct the predicted or detected unsafe or undesirable movement.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

BRIEF DESCRIPTION OF THE DRAWINGS

FIGS. 10A-10B. Block diagram of two embodiments of a movement disorder recovery system of the present invention for: 10A) reporting systems providing a report to a clinician and allowing feedback or intervention by the clinician; and 10B) automated treatment systems.

DETAILED DESCRIPTION OF THE PRESENT INVENTION

Figure 1A:
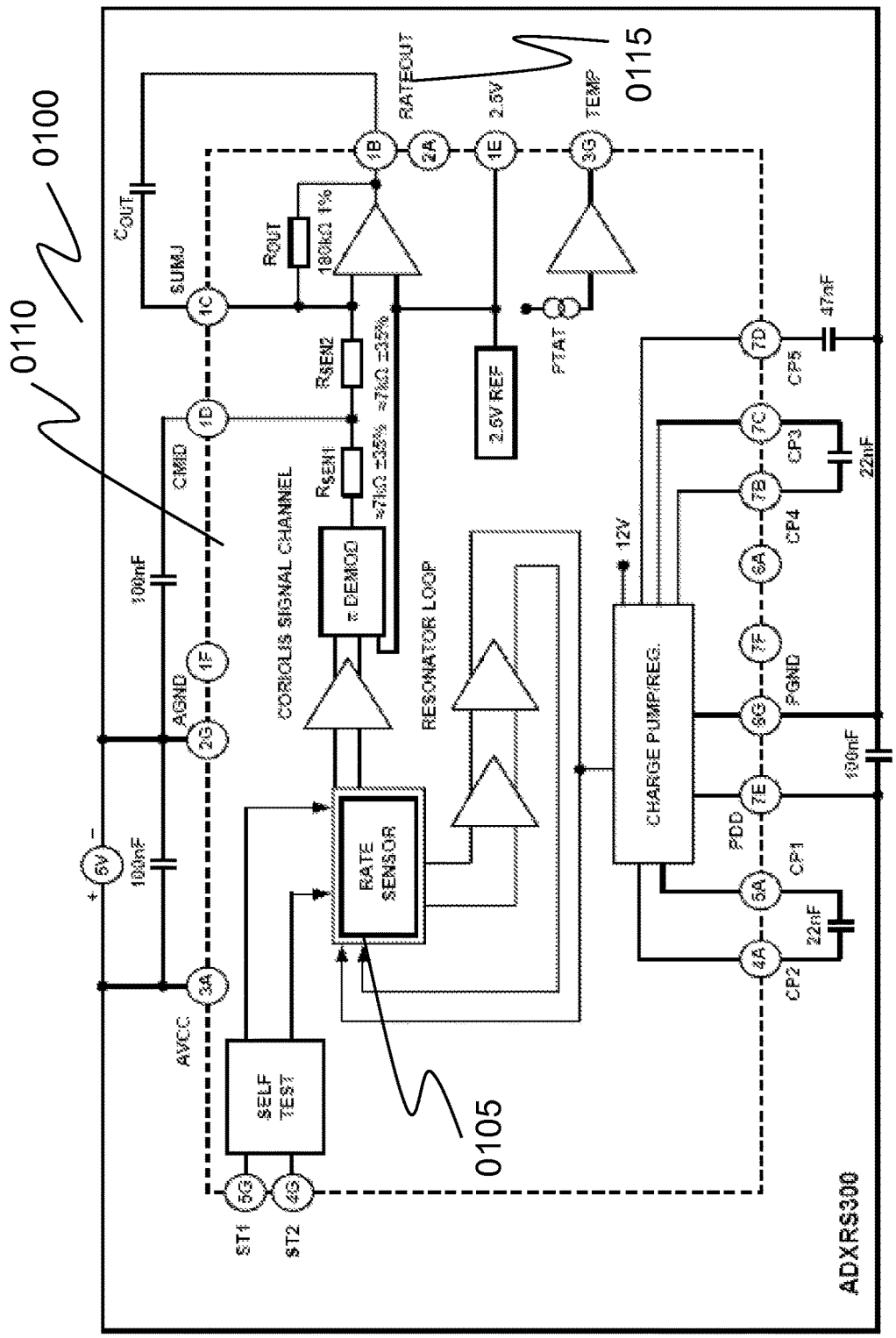
FIGS. 1A-1C. Electrical schematics of gyroscopes useful in the present invention: 1A) and 1B) are schematics of single-axis gyroscopes; and 1C) dual-axis gyroscope.

The present invention relates to a customizable and adaptive movement recovery, therapy and training system and method of improving the functional motor recovery, efficiency and safety of a subject suffering from an injury, a movement disorder, or any other movement impairment. The devices, systems and methods of the various embodiments of the present invention are used for customizing and monitoring treatment and therapy for various types of injuries and movement disorders. Allowing subjects to receive customized treatment and therapy in a non-hospital setting such as their home, and particularly while performing normal everyday activities of daily living, increases treatment and therapy efficacy, and hence the amount of functional improvement. Injuries or conditions affecting movement, particularly those affecting gait, balance, posture, may include, but are not limited to, traumatic brain injury (TBI), stroke, cerebral palsy, or Tourette's syndrome, and movement disorders and their symptoms for purposes of this application include, but are not limited to, those movement disorders stemming from a disease or injury to the nervous system where electrical stimulation, pharmaceutical treatment, or physical therapy has been or are determined to benefit the subject by either improving the subject's movement or by preventing either further degradation or not as rapid degradation of the subject's condition. Examples of such movement disorders and their symptoms that can be treated with the systems and methods of the present invention include, but are not limited to, stroke, traumatic brain injury, cerebral palsy Parkinson's disease (PD), essential tremor, dystonia, and symptoms such as abnormal muscle synergies, abnormal movement kinematics, tremor, bradykinesia, abnormal muscle tone (e.g. spasticity, dystonia, rigidity), and gait/balance disturbances. The systems and methods of the present invention can also preferably be used to prevent, detect, predict, treat or provide therapy for undesired or undesirable movements or conditions as well, such as compensation strategies that a subject might use to alleviate pain or discomfort from some other disordered, unsafe or symptomatic movement or condition, and also hyperextension of various parts of the body, such as during exercise or stretching. The subject on which the devices, system or method is used is a human or other form of animal.

The devices worn by the various subjects or the different systems of the various embodiments of the present invention are preferably portable. By portable it is meant among other things that the device is capable of being transported relatively easily. Relative ease in transport means that the therapy device is easily worn and carried, generally, in a carrying case to the point of use or application and then worn by the subject without significantly affecting their range of motion. Further, portability in the sense of the present invention preferably means that all or a portion of the subject-worn device(s) is concealable and not openly visible while being worn by the subject. Furthermore, the portable therapy system or device preferably should be relatively light-weight. By relatively light-weight, preferably the device weighs less than about 3 lbs., more preferably less than about 2 lbs., even more preferably less than about 1 lb., even more preferably less than about 0.5 lbs., still more preferably less than about 0.1 lbs., and most preferably less than about 20 grams. By being light-weight and further compact, the therapy device should gain greater acceptance for use by the subject. The entire therapy system including the therapy device, feedback modality, and other components including any processors, computers, video screens and the like preferably weigh less in total than about 15 lbs., more preferably less than about 10 lbs., even more preferably less than about 5 lbs., still more preferably less than about 2 lbs., and most preferably less than about 0.5 lbs. This system more preferably can fit in a reasonably sized carrying case so the subject or their caregiver can easily transport the system. Further, the portions of the device that are not worn by the subject while the device is in use (e.g., processing and cuing device—smart phone) should be easily and readily carryable and concealable, such as able to fit into a purse or pocket.

Another advantage of the systems and methods of the present invention is the ability to determine perform the steps of movement measurement and analysis steps including determining or predicting unsafe or undesirable movement, instability, or some other cause or condition requiring the subject's attention, transmitting a signal or output to the cueing device and providing a cue to the subject in real-time, herein referred to as movement analysis time. Preferably the system is able to measure the subject's movement, analyze the data and provide a cue to the subject in less than 2 minutes (this can be referred to as real time sensing, analysis and cueing). More preferably, the system can measure the subject's movement, analyze the data and provide a cue to the subject in less than 1 minute. Still more preferably, the system can measure the subject's movement, analyze the data and provide a cue to the subject in less than 30 seconds. Yet more preferably, the system can measure the subject's movement, analyze the data and provide a cue to the subject in less than 1 second. Even more preferably, the system can measure the subject's movement, analyze the data and provide a cue to the subject in less than 500 milliseconds. Still yet more preferably, the system can measure the subject's movement, analyze the data and provide a cue to the subject in less than 100 milliseconds. Even still more preferably, the system can measure the subject's movement, analyze the data and provide a cue to the subject in less than 50 milliseconds. Yet even more preferably, the system can measure the subject's movement, analyze the data and provide a cue to the subject in less than 1 millisecond. Most preferably, the system can detect or predict the unsafe or undesirable movement or instability and provide a cue to the subject essentially simultaneously.

Still another advantage of the present invention is the ability to provide a cue to a subject, herein referred to as cue or stimulus reaction time that is similarly a small amount of time. Cue or stimulus reaction time refers to the amount of time it takes for a typical subject to receive a cue or stimulus from the portable therapy system or device, recognize the cue or stimulus and what it means, and to respond to the cue or stimulus to prevent or correct the unsafe, undesirable or impaired movement. Preferably, the cue or stimulus reaction time is less than 2 minutes. More preferably, the cue or stimulus reaction time is less than 1 minute. Yet more preferably, the cue or stimulus reaction time is less than 30 seconds. Still more preferably, the cue or stimulus reaction time is less than 15 second. Still yet more preferably, the cue or stimulus reaction time is less than 2 seconds. Even still more preferably, the cue or stimulus reaction time is less than 1 seconds. Yet even more preferably, the cue or stimulus reaction time is less than 0.50 seconds. Still yet more preferably, the cue or stimulus reaction time is less than 0.10 seconds. Most preferably, preferably, the subject is able to receive, recognize and react to the cue or stimulus essentially simultaneously.

Effectively, the three distinct time periods defined above are intended to operate under the real-time constraints also defined above. In light of the rapid timing of the two stages defined above, the system therefor further provides the advantage of allowing the subject to react to the stimulus a very short period of time after the impaired or unsafe or undesirable movement is measured by the system, and this time period is herein referred to as measurement-to-reaction time. Preferably, the measurement-to-reaction time is less than 4 minutes. More preferably, the measurement-to-reaction time is less than 2 minutes. Still more preferably, the measurement-to-reaction time is less than 1 minute. Yet more preferably, the measurement-to-reaction time is less than 2 minutes. Even more preferably, the measurement-to-reaction time is less than 30 seconds. Still yet more preferably, the measurement-to-reaction time is less than 5 seconds. Even yet more preferably, the measurement-to-reaction time is less than 3 seconds. Yet still more preferably, the measurement-to-reaction time is less than 1 second. Even still more preferably, the measurement-to-reaction time is less than 750 milliseconds. Yet even more preferably, the measurement-to-reaction time is less than 250 milliseconds. Still even more preferably, the measurement-to-reaction time is less than 50 milliseconds. Most preferably, the system measures the subjects movement, analyzes the data transmits a signal or output to the cueing or stimulus device which delivers the cue or stimulus to the subject who recognizes the cue or stimulus and reacts to the cue or stimulus substantially simultaneously.

The present invention is able to provide these significant improvements over systems known to those of skill in the art based on the enhanced and improved hardware and software of the present invention. The sensors utilized with the present invention are more sensitive and accurate than traditional sensors known to those in the art, allowing the system to acquire cleaner, higher quality signals and measurements directly from the subject with less noise or artifacts that need to be removed, and thus minimizing the amount of pre-processing and signal conditioning required, and time required to do so, in order to properly distinguish unsafe, undesirable or disordered movement. Further, the processing components of the present invention are more powerful and the algorithms more efficient and better optimized, allowing the system to operate more quickly, more efficiently, and more accurately than those known in the art, further decreasing the time required to analyze the measured data and to predict or detect unsafe, undesirable or impaired movement.

The devices of the various embodiments of the present invention can form part of a system for use by individuals with movement disorders, a physician, veterinarian, technician, clinician or therapist for therapy, treatment and further diagnosis of a subject's injury or movement disorder; for pharmaceutical research; or for delivery of pharmaceutical compounds or other treatment or therapeutic methods. Other elements of this system may include but are not limited to receivers, routers, communication devices, processors, displays, output devices, drug delivery devices, electrical stimulators, databases, algorithms, and the like, some of which are described further in various embodiments described in more detail below.

The preferable portable therapy system or device, described in greater detail below, worn, carried by or attached to the subject, contains various physiological or movement sensor(s) used to measure the subject's external body motion and/or other physiological signals from the subject's body. The portable therapy system or device preferably comprises a device enclosure at least comprising the processing and analysis electronics of the system. The sensors of the portable therapy system or device may be included in or with, internal to, integrated into, or attached to the device enclosure, or may be separate from the device enclosure. Separate sensors may be individually attachable to the subject, or may be included in or with, internal to, integrated into, or attached to a sensor device that can be worn or attached to the subject's person, clothing or gear or equipment, or carried by the subject. Given the preferably subtle nature of the system of the present invention, the sensors may be integrated into the subject's clothing, jewelry (e.g., rings, bracelets, and the like), watches, etc. such that they can be worn and placed in contact with the subject to measure the subject's movement while be unnoticeable to others around the subject. The device enclosure may take on various forms in the various embodiments of the present invention. The device enclosure may be a standalone, manufactured device designed and manufactured specifically for use in the systems and with the methods described herein. Alternatively, the device enclosure may take the form of a commercially available device that allows software to be installed to perform the processing and analysis functions. In such embodiments, the device enclosure of the portable therapy system or device can be any smartphone, tablet, personal digital assistant (PDA), personal fitness or activity tracking and/or monitoring device, laptop or other computer or processing device that is readily and easily worn, carried, attached to or otherwise portable with the subject. With such commercial-product enclosure embodiments, the system preferably utilizes software or an application and a user interface, comprising necessary algorithms, installed on the device and used to receive, process and analyze movement data acquired from the sensor(s) of the system.

Preferably, the portable therapy system or device operates to provide a real-time feedback system wherein the sensors acquire movement data, the movement data is processed and analyzed, impaired or unsafe or undesirable movement is detected and a cue or stimulus is provided to the subject—all rapidly enough such that the subject can react to the cues and correct or prevent the impaired or unsafe or undesirable movement from continuing, worsening, or causing injury or harm to the subject. In some embodiments, the portable therapy system or device may optionally temporarily store the subject's movement or physiological data in onboard memory and/or transmit this data to an external device. In some embodiments, the portable therapy system or device may optionally directly or indirectly transmit the data to a centralized database, to multiple databases at the same or multiple locations, or to a cloud-based software or database where the data can be stored and accessed essentially immediately by authorized users who can analyze and/or further process the data, use it to diagnose or assess the subject's symptoms or disorders, or the like, onsite and/or at various other outside locations. Additionally, or alternatively, the portable therapy system or device can optionally transmit the movement or physiological data to an external computer device, or directly to a remote location for access by a clinician, physician or technician. Such optional transmission to a remote location preferably may include transmission directly to such a computer, storage or processing device at said remote location, or may involve a user (such as a clinician, physician or technician) at the remote location accessing the data or information through the database or databases as described.

The device enclosure or computer device is understood to be any type of device known to those skilled in the art usable for the intended purpose(s) or function(s), including, but not limited to, desktop computers, laptop computers, tablet computers, personal digital assistants (PDAs, "smart" cellular telephones, and the like). As noted above, the device enclosure or computer device may be a separate, standalone device provided as part of the present invention's system, but in many embodiments the device enclosure or computer device is any suitable device of any third-party manufacturer or provider who provides such devices for the intended function or purpose of the present invention. In such cases, a software installation providing the user interface, signal processing software, processing algorithms, diagnostic and analysis tools, and the like would simply be installed on the third-party computer device or tablet as software or an application (or "app"), or the interaction with the user(s) can be web based through a web portal. Additional processing or analysis capabilities may be included, for example those that allow for review by a clinician, physician, therapist or technician such as with a telemedicine application in real time or essentially real time or at a later time. Such additional tools may be used to analyze the subject's past movement or performance in order to diagnose various disorders, diseases, impairments or the like. Further, such tools may be used to determine or develop treatment methods, strategies and techniques for the subject going forward to address any predicted or detected impairments or disorders, or symptoms thereof. One example of such an analysis tools includes tuning maps, such as described in U.S. patent application Ser. Nos. 13/861,790 and 13/153,063 which are herein incorporated by reference, and which allows the clinician, physician or technician to review and/or determine the next, or preferably best (optimized) therapeutic settings or parameters for the subject's therapy, treatment or assistance device, such as a DBS device, in embodiments where such devices are included, based on the movement and analysis data measured and calculated by the system or device. The movement data would be used to populate tuning maps which can then be saved and/or transmitted for later analysis and/or review.

Various embodiments of the present invention may include different sensors known to those skilled in the art to sense motion, physiological conditions of the subject and the like. Of these various embodiments of the present invention some may include a sensor for measuring a subject's external body motion. Many types of sensors are known by those skilled in the art for measuring external body motion. These sensors include but are not limited to accelerometers, gyroscopes, magnetometers, resistive bend sensors, load cells, combinations thereof, and the like. The part of the body wearing the sensor and being measured for motion may be a limb (as at a wrist, ankle, heel, thigh, or finger) or may be the trunk of the body (as at a shoulder, waist, or torso) or according to other techniques known to those skilled in the art. In most embodiments, a combination using at least three axes each of an accelerometer and gyroscope is preferably used at a combination of limb and trunk locations.

As noted, various embodiments of the present invention may include at least one sensor for measuring a subject's external body motion. The invention may also include at least one sensor for indirectly measuring movement metrics. Many types of sensors are known by those skilled in the art for measuring external body motion or providing physiological signals through which body movement information may be derived. External body motion sensors include but are not limited to accelerometers, gyroscopes, magnetometers, resistive bend sensors, combinations thereof, and the like. Preferably, a combination using at least an accelerometer and gyroscope is used. Sensors through which body movement information may be derived include, but are not limited to, electromyogram (EMG), electrooculogram (EOG), electroencephalogram (EEG), electrocardiogram (EKG), or other physiological signals which can directly or indirectly measure movement metrics in the subject may be included if such sensors and signals may be used to sense, detect, measure, and/or quantify the subject's external body motion, or related aspects or kinematic features thereof.

In embodiments where a gyroscope is a sensor or one of the sensors of an embodiment of the present invention, any type of gyroscope may be used. Single-, dual-, and three-axis are available in the market, though the most preferable for use with the present invention are three-axis gyroscopes. Gyroscope sensors, described in greater detail below, can be used to measure orientation and angular momentum, or one as a function of the other. Orientation measurement is useful for determining spatial positioning of a particular body part, and movement in three-dimensional space.

In embodiments where an accelerometer is used, any type of accelerometer may be used. Single-, dual-, and three-axis are available in the market, though the most preferable for use with the present invention are three-axis accelerometers. Accelerometer sensors, described in greater detail below, can be used to measure acceleration, or more specifically, proper acceleration as opposed to coordinate acceleration. Acceleration measurements are useful for determining the acceleration and change in acceleration of a particular body part as it moves.

In preferred embodiments, a single sensor unit comprising at least an accelerometer and a gyroscope may be used. More preferably, a single chip containing both a 3-axis accelerometer and a 3-axis gyroscope, may be used. The sensor unit preferably not only comprises at least an accelerometer and a gyroscope, but also allows for integration of other sensors internal or external to the sensor unit. Preferably, the accelerometer and gyroscope are each three-axis sensors capable of measuring their respective movements (acceleration and orientation, respectively) in each of the three dimensions of movement (X, Y and Z). Each of the accelerometer and gyroscope may output a separate signal for their respective measurements in each axis, and these signals are all converted from analog to digital by a bank of analog-to-digital converters (ADC). The separate ADCs for each axis of the accelerometer and gyroscope allow for simultaneous sampling of each sensor and eliminate the need for an external multiplexer. Preferably the sensor unit as a whole, and the accelerometer and gyroscope in particular are capable of operation with low power consumption. Preferably, the accelerometer and gyroscope are user-programmable such that the user may define an operating range in which the sensors will work (e.g., the accelerometer may be programmed to operate from as low as ±2 g to as high as ±16 g, and the gyroscope maximum range from as low as ±250 degrees/second to as high as ±2000 degrees/second). Some embodiments may include other sensors integrated into the sensor unit as well, for example, a temperature sensor, which may be used to monitor the temperature of the sensor unit and ensure it is operating properly and under safe conditions.

Various embodiments of the present invention may include another variety of sensor for measuring the subject's electrical muscle activity through techniques such as electromyography (EMG) or the like. Electrodes, and particularly EMG electrodes are preferably used to acquire biopotential EMG signals relating to the electrical activity caused by the subject's muscles. With an EMG sensor, a voltage difference or difference in electrical potential is measured between at least two recording electrodes. The electrodes used can be any type known to those skilled in the art including both indwelling (needle), surface and dry electrodes, though preferably surface electrodes are used. Typical EMG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. More preferably, however, conductive fluids and skin preparation are avoided by the use of dry physiological recording electrodes of the type described in U.S. patent application Ser. No. 09/949,055, which are herein incorporated by reference. Dry electrodes provide the advantage that there is no gel to dry out and no skin to abrade or clean. Additionally if electrodes are used as the sensor(s), preferably at least three electrodes are used—two signal electrodes and one reference electrode.

In many embodiments, the portable therapy system or device comprises a kinetic sensor board (or subject worn external sensor). The kinetic sensor board is preferably configured with at least an accelerometer and a gyroscope for quantifying the subject's motion, and preferably at least one 3-axis accelerometer and at least one 3-axis gyroscope. The kinetic sensor board also preferably includes a microprocessor and a power interface section.

Another type or variety of sensor that may be used to measure the subject's movement may include visual or optical sensors such as video cameras or motion capture sensors that, in most embodiments, are not worn by the subject as are the other sensors discussed herein. Such sensors can be mounted or placed away from the subject and used to record and detect the subject's movement from a third-party perspective. Such sensors may combine traditional video sensors that capture picture or video along with other sensor or measurement technology that can provide quantifiable measurements of movement and recognition of movement, movement patterns, and even kinematic features of the movement (described in greater detail below). The preferred visual or optical sensor device for use with the present invention must be able to provide measurement of the kinematic features of the subject's movement in order to provide safe and effective cueing. Measurement of the kinematic featured of movement with a separate visual or optical sensor can performed by any sensors known to those of skill in the art combine with video sensor technology readily to provide the required measurements. By way of non-limiting example, a depth sensor comprising a laser array projector and an active pixel sensor or array of pixel sensors may be used, in conjunction the wide sensors, to correlate the subjects movement captured by video with the spatial measurements obtained by the depth sensor in order to determine the actual movement of the subject and be able to measure the various kinematic features of the movement. Such sensing technology utilizes the depth sensor to detect and recognize individual joint movement for multiple joints of the subject simultaneously, and thus allows a more robust and complete measurement of the subject's movement by creating and measuring the complete three dimensional movement of the subject. An example of the type of non-subject-worn sensor that can be used with the present invention is the Microsoft Kinect™ sensor.

Many other sensors are considered for use in the various embodiments of the present invention and may optionally be included based on the particular embodiment. Such other sensors may include microphones, magnetometers, resistive bend sensors, load cells, pressure sensors, altimeters, temperature sensors, physiological electrodes for EMG and other biopotential signals, and the like.

The sensor unit further preferably comprises a digital motion processor (DMP), which may perform some preprocessing or processing of the sensor signals using motion-related algorithms. The digital motion processor at least preprocesses and/or processes the accelerometer and gyroscope signals to begin the analysis of the signals and to decrease the processing load on the external processor. Many embodiments may include external or additional sensors that are not housed within the sensor unit, but whose signals are transmitted to the sensor unit for integration with the accelerometer and gyroscope signals for further transmission to external components such as a processor. Such external or additional sensors may include, but are not limited to, force sensors, magnetometers, pressure sensors, bend sensors, combinations thereof, and the like. These external or additional sensors communicate with the sensor unit by means of an auxiliary communications interface. A digital motion processor can integrate the signal(s) from these external or additional sensors along with the accelerometer and gyroscope signals and perform preprocessing or processing of all of the signals together, thus further streamlining the data acquisition process and reducing the workload of the external processor.

In many embodiments, the electrical components of the portable therapy system further include a power receiver. The power receiver is the component, which receives the electrical charge from the external power source (not shown). The external power source can be any device for supplying power to the portable therapy system. In some embodiments, the external power source may be a docking station to which the portable therapy system can be connected, attached, docked, or placed into whereby a physical or proximal connection is made between the docking station and the portable therapy system thus allowing power to be transferred via the physical or proximal connection. In other embodiments, the external power source may merely involve plugging the portable therapy system into a traditional power outlet. In still other embodiments, the external power source may be an inductive charging mat or pad onto which the portable therapy system is placed and power may be inductively transferred between induction coils in the charging mat or pad and the inductive coils in the power receiver of the portable therapy system, as described herein. As the power receiver, which may be wireless or wired depending on the embodiment, receives power, it transfers said power to a power manager which controls and directs where the incoming power is delivered.

The radio of the device controls and carries out communications between the device components, and between the portable therapy system or device and external devices (not shown). The radio receives power directly from the power manager. As described herein, the radio may be a Bluetooth® communications device to provide wireless communications with external components such as computers or processors, data acquisition circuitry, internet or cloud-based memory banks or databases, and the like, as well as internal components such as the internal portable therapy system or device memory, microprocessor, and the like. Both internal (between electrical components of the subject-worn sensor device) and external (between the subject-worn sensor device and external components or devices) communications may also be transmitted through wireless, wired, or a combination of both systems and methods. The microcontroller comprises algorithms and protocols for coordinating the operation of at least these internal electrical components, and in some embodiments also for preprocessing or processing sensor data.

The portable therapy system or device of the present invention further preferably comprises a transceiver module, or command module. Preferably the sensor unit and transceiver/command module are enclosed in the same housing constituting a single unit, though they may be separate units. The transceiver module includes communications electronics, such as a Bluetooth® radio to provide wireless communications with computer or processor device(s), on board memory, a microprocessor, and a battery power supply that supplies power to both the transceiver module and one or more sensor modules. The transceiver module may also include a USB port to provide battery recharging and serial communications with the subject PC. The transceiver module may also include a push button input.

In many embodiments, the transceiver/command module contains one or more electronic components such as a microprocessor for detecting and acquiring both the signals from the sensors, including gyroscopes and accelerometers, and for detecting and acquiring signals from the EMG electrodes or other such sensors when present. Preferably, the one or more electronic components also filter (and preferably amplify) the kinetic motion signals and EMG signals, and preferably convert these signals, which are in an analog form into a digital signal for transmission to a remote receiving unit, computer or other similar device. Though, more preferably, the device uses the herein described 3-axis accelerometer and 3-axis gyroscope chip which comprises ADC circuitry and thus outputs a digital signal. The one or more electronic components can be attached to, worn by, or carried by the subject as part of the portable therapy system or device. Further preferably, the one or more electronic components can receive a signal from remote devices such as the subject's portable therapy system or device (if an optional separate transceiver is used) or a remote database or clinician computer device. The one or more electronic components may include circuitry including, but not limited to, for example, electrode amplifiers, signal filters, analog to digital converter, Bluetooth® radio or other receiver, transmitter or transceiver components, a DC power source and combinations thereof. The one or more electronic components may comprise one processing chip, multiple chips, single function components or combinations thereof, which can perform all of the necessary functions of detecting a kinetic or physiological signal from the sensor or electrode, storing that data to memory, uploading data to a computer through a serial link, transmitting a signal corresponding to a kinetic or physiological signal to a receiving unit and optionally receiving a signal from a remote transmitter. These one or more electronic components can be assembled on a printed circuit board or by any other devices or methods known to those skilled in the art including but not limited to an ASIC chip. Preferably, the one or more electronic components can be assembled on a printed circuit board or by other means so its imprint covers an area less than 4 $in^2$, more preferably less than 2 $in^2$, even more preferably less than 1 $in^2$, still even more preferably less than 0.5 $in^2$, and most preferably less than 0.25 $in^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable.

Optionally, the data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

Preferably, the circuitry of the sensor board and/or transceiver module comprises a digital section. More preferably, the heart of the digital section of the sensor board is a micro-controller or processor. The microcontroller or processor preferably contains sufficient data and program memory, as well as peripherals which allow the entire digital section to be neatly bundled into a single carefully programmed processing chip. Still more preferably, the onboard counter/timer sections are used to produce the data acquisition timer.

Preferably, the circuitry for the one or more electronic components comprises nonvolatile, rewriteable memory for storing kinematic, movement, result, and other data, as well as RAM used to store operational data such as the pending mode (i.e., sleep or test mode), period and number of seconds to record data, daily alarm time, amount of time to collect data, and the like. Preferably, enough nonvolatile memory is included to record at least 8 hours of kinematic data. More preferably, enough nonvolatile memory is included to record at least 2 hours of kinematic data. Still more preferably, enough nonvolatile memory is included to record at least 6 hours of kinematic data. Yet more preferably, enough nonvolatile memory is included to record at least 8 hours of kinematic data. Even more preferably, enough nonvolatile memory is included to record at least 12 hours of kinematic data. Even yet more preferably, enough nonvolatile memory is included to record at least 24 hours of kinematic data. Still even more preferably, enough nonvolatile memory is included to record at least 48 hours of kinematic data. Even yet more preferably, enough nonvolatile memory is included to record at least 7 days of kinematic data. Further preferably, the system is designed to allow for over-the-air programming even once the circuit design has been completed and the circuit has been installed into the portable therapy system or device. In such embodiments, the firmware may contain a boot-loading program that, once turned on, looks for programming signals. Thus, such programming signals can be delivered and the device updated, even after manufacture and shipment to a clinic, or even when in the possession of a subject. Alternatively, the firmware may be updateable on demand either automatically, semi-automatically and may be done periodically as needed, on a set schedule, or ad hoc through interrogation of the system to determine if new parameters are needed.

Preferably the circuitry of the one or more electronic components includes an RF transmitter and/or an RF receiver, or a RF transceiver. Still more preferably the circuitry of the one or more electronic components includes a Bluetooth® radio system requiring an average of about 42 mA of electrical current to operate. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, or strip conduction or reflector antenna. The antenna is designed to include but not be limited to the best combination of usable range, production efficiency and end-system usability. The antenna can serve to just transfer data or for both transferring data to and for receiving control data received from a computer device and/or receiving unit which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode or sensor and/or the computer device and/or receiving unit. The couplers being used to measure the radiated or reflected radio wave transmission output. Any damage to the antenna (or also any faulty adaptation) thus can be registered, because it is expressed by increased reflection values.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system preferably includes an error control sub-architecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the remote communication station is capable of recognizing errors and requesting a renewed transmission of the data. In the presence of excessive transmission problems such as, for example transmission over excessively great distances or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

As noted above, the present invention may be used in conjunction with other treatment, therapy or assistance devices, systems and modalities, such as with deep brain stimulation (DBS) devices, Baclofen pumps, transcranial direct current stimulation (tDCS) devices, pharmaceutical delivery devices (e.g., drug titration and delivery systems, implanted or externally worn), and other such systems and devices. Such treatment, therapy or assistance devices and/or methods are intended to be complementary, and possibly even secondary considerations to the cueing and stimulation of the system, but to operate in a synergistic manner such that the cueing device can be used to control and complement the treatment or therapy device to best supply the proper amount, type or level of treatment or therapy to the subject. Examples of such treatment, therapy or assistance devices and/or methods include automated stimulation devices such as deep brain stimulation (DBS) and functional electrical stimulation (FES devices), and closed-loop or semi-closed loop drug or medication titration and delivery systems, each of which is described in greater detail below. The main object of the present invention is to provide a cue or stimulus to the subject so that the subject may be notified of a predicted or detected movement impairment, symptom of a movement disorder, unsafe or undesirable movement condition, or any other such impairment, and consciously take appropriate steps to prevent or counter the impairment or unsafe or undesirable condition. Through continuous use of the system, it is intended for the subject to train his or her behavior to be able to overcome and no longer experience the impairments or unsafe or undesirable conditions. However, if there may be impairments or unsafe or undesirable conditions that are too severe for the subject to address merely by focusing and correcting his or her movement, or that may arise so quickly that the subject does not have time to react accordingly, or where the subject ignores or misses the cue or stimulus and thus does not react thereto. Therefore, various embodiments of the present invention accommodate the use of such treatment, therapy or assistance devices in order to act where the subject cannot or does not or to assist the subject in acting accordingly in response to the provided cue or stimulus. In these embodiments, the included treatment, therapy or assistance device(s) would preferably only activate under circumstances where the subject is unable to or fails to react to the cues or stimulus and thus the predicted or detected impairment or unsafe or undesirable condition persists or worsens. In the case of a DBS device, the system may activate the DBS device to reduce the effects of abnormal muscle tone (dystonia) on gait or upper extremity movement quality. Similarly, with an FES device, the system may activate the FES device to provide electrical stimulation to a particular muscle to help the subject perform the necessary movement correction. A drug or medication titration and delivery system may be utilized to administer, for example, Baclofen through a Baclofen pump. The system would detect inability to use stretching and relaxation techniques to manage lower extremity spasticity effects on movement. The system would then increase the Baclofen dose to help reduce spasticity effects and improve gait. In another example, the system can titrate and deliver an anti-seizure medication or Parkinson's disease drug, if the system detects seizure or Parkinson's disease symptoms, respectively, and the subject cannot act to prevent the occurrence of the seizure or symptom. These devices are not intended to be an exclusive list of potential treatment, therapy or assistance devices contemplated for use with the present invention, but merely exemplary selections intended to show the type of devices contemplated for use and the manner in which they are best used in conjunction with the present invention.

The present invention includes various methods of measuring a subject's motion and muscle activity and using those parameters to provide feedback and control for therapy. These methods include a number of steps which may include but are not limited to measuring a subject's external body motion; transmitting wirelessly or over a hardwire link a signal based in part on the subject's measured external body motion; receiving the wirelessly transmitted signal or over a hardwire link; and providing feedback, electrical stimulation, automatic drug delivery, or other treatment protocols based in part on the signal.

Some embodiments of the present invention further include a treatment delivery system. The treatment delivery system utilizes in part the input from the external sensors as input into a closed loop control system to deliver electrical stimulation or medication to lessen or relieve the impairments or symptoms. Treatment delivery systems are intended to be used in conjunction or in addition to the other components of the system described herein and add treatment or therapy functionality to the movement measurement and cueing system. A system for electrical stimulation further comprises an implanted electrode which when activated sends an electrical stimulus to surrounding tissues such as a skeletal muscle or the globus pallidus internus of the brain. The system further comprises a pulse generator which activates to send an electrical current to the implanted electrode based in part on a signal from the at least one external sensor. Similarly, a treatment delivery system for medicine further comprises a reservoir for some form of medication, preferably liquid, that can either be delivered to the subject internally or transcutaneously. The system further comprises an actuator or pump which when activated and deactivated allows the medication to be delivered from the reservoir to the subject. Finally, the system further comprises a closed-loop control system which activates and deactivates the actuator or pump based in part on a signal from the at least one external sensor.

Various embodiments of the present invention include a device for providing deep brain stimulation (DBS) or functional electrical stimulation (FES) to the subject. Forms of electrical stimulation are advantageous compared to other therapies since it can be non-invasive with minimal side effects. The system may utilize electrodes placed on the surface of the skin (FES) or with implanted electrodes (DBS and FES). DBS and FES electrically stimulate the brain and individual muscles respectively to create a desired reaction, such as muscle contraction or inhibition. Some movement disorder subjects have paralyzed muscles while others have weak muscles that are over powered by spasticity of an opposing muscle group. Therefore, a muscle normally required for a therapy, but inactive due to a movement disorder can be included during therapy using FES. On the other hand, some movement disorder subjects suffer from involuntary muscle contractions, such as tremor. In these cases, treatments such deep brain stimulation can be used to help suppress such contractions. In addition, using FES at the sensory level helps the subject to localize the muscles used for a particular therapy task. Sensory stimulation in conjunction with physiotherapy may improve motor skills. Providing feedback from the subject's own movements facilitates motor learning and may drive cortical reorganization.

The main components of an electrical stimulation system of various embodiments of the present invention are the electrodes, the stimulator (or pulse generator), and sensors or switches. When FES is being used to move muscles, current pulses in the electrodes cause the weakened or paralyzed muscles to contract. In other applications, currents in the electrodes may produce electrical currents in the tissues without moving any muscles. The stimulator controls the strength and timing of the low-level pulses that flow to the electrodes. The sensors or switches control the starting and stopping of the pulses supplied by the stimulator.

Many modes of a FES device or system can be used in the movement disorder recovery system and methods of the present invention. Two modes which are used by way of example but not limitation include 1) adaptively modulating stimulation during therapy, and 2) increase muscle strength through exercise.

One embodiment of the electrical stimulation device, unit or system of the present invention is a battery powered device. This device, as an FES unit, can deliver up to four channels of stimulation using a 3.7V Lithium Polymer rechargeable battery. Each channel can deliver electrical impulses to a different target muscle. This device uses a two-stage stimulator power supply, which multiplies the small voltages from the battery into a voltage large enough for the desired stimulation. Each stage has a charge pump which pulls the charge directly from the batteries. Stage one produces five volts, while stage two produces 60 volts and contains the high voltage section and the main power regulator for the circuit. The 60 volts is produced by the high voltage section, which is comprised of a charge pump and two 2.2 µF capacitors placed in series. Each capacitor can hold up to 35 volts of charge. A bleed-off branch funnels any excess charge from the capacitors back to the charge pump, which acts as a feedback regulator preventing the charge pump from pulling more charge from the batteries. In this way, energy is not wasted. An LED is designed into the second stage to indicate voltage. The main power regulator produces 3.3 volts for the rest of the circuit.

The stimulator is attached to a processor. This acts as the central control unit for the stimulator. The unit includes two serial ports, an SPI port, and multiple timers and counters. The four output channels are set on the digital to analog converter using the SPI port. The digital to analog converter drives the amplitude of the four channels in the output stage.

The output stage is where the stimulation pulse is delivered. This phase is used to charge up the capacitors, which are then discharged. This is called the cathodic stimulating phase. The capacitors are recharged during the anodic recharging phase. The digital to analog converter sets the amplitude levels for each of the four channels. The converter has eight bits of resolution, which results in 0.2 mA steps from 0 to 50 mA. This analog output (for each channel) goes through the buffer amplifiers, which in turn control the gate on the output transistor. The speed at which the charge comes off the capacitors depends on the amplitude hitting the gate of the output transistor. This speed determines the amount of the stimulating current. When the capacitors discharge, the control unit turns off the cathodic phase and enables the capacitors to recharge (the anodic phase). During recharging, the control center connects the high voltage section to the output capacitor through a current-limiting FET circuit.

Another example of a battery powered electrical stimulation device may be a deep brain stimulation (DBS) unit. DBS units, powered by a rechargeable lithium-ion battery unit, can deliver stimulation to 1 or 2 leads which are generally implanted in the subthalamic nucleus, globus pallidus interna, or ventro intermediate nucleus of the thalamus. A DBS lead is connected to an implantable pulse generator (IPG), which serves as a controller and power source, via an extension cable tunneled subcutaneously to a subcutaneous pocket in the chest or abdominal cavity. The IPG typically includes the rechargeable lithium-ion battery and circuitry for telemetered communication with an external programming device used to adjust, or "tune," DBS lead stimulation parameters. Examples of DBS programming methods and systems are provided in U.S. patent application Ser. No. 13/861,790, U.S. patent application Ser. No. 13/918,948, U.S. patent application Ser. No. 14/022,323, and U.S. patent application Ser. No. 14/022,376, each of which are hereby incorporated by reference.

Various embodiments of the present invention that include a central database system may consist of one or many databases specialized to certain forms of subject and/or movement data, such as subject demographics, treatment history, disorder details, recorded movement data, current treatment protocols, movement scores, and the like. Movement scores are not simply meant to be a rescaling of a measured quantity. Rather, preferably they should be representative of a score that a skilled clinician might give to the subject during a movement analysis exam in the clinician's office using a standardized scale such as the Unified Parkinson's Disease Rating Scale (UPDRS), for example. The database may comprise an internal, integrated memory that is part of the portable therapy system or device, or may be an external, standalone computing and memory device or system in communication with the portable therapy system or device. The database may be prepopulated with information and data from various sources, including other third party subjects, or may be trainable and/or trained to include the instant subject's data. The trainable or trained database is preferably able to be continuously updated with new data from the instant subject either on a periodic, scheduled or continuous, substantially real-time basis. Preferably, the system comprises both internal database memory and an external database system whereby the internal database can be updated by communicating with the external database to include the most relevant data to the instant subject. Preferably, all databases will be adaptive to new subject information, and will grow in size as their use increases, thereby increasing the effectiveness of correlation algorithms as they have more information to compare and contrast with. The database system may be of any framework readily known to those skilled in the art, such as SQL, XML, or the like, so as to allow for relational queries between the databases and correlations with outside data.

Any database or database system of the present invention should comply with the Health Insurance Portability and Accountability Act (HIPAA) of 1996, particularly Title II of the act, which covers the privacy of protected subject and subject health care information. Protected information may be any part of the subject's medical record or payment history which may be linked to the individual. Such information related to this invention may include subject demographics, health history, recorded movement data, past and current treatment protocols, clinician notes, subject disorder diaries. All data may only be obtained and stored with HIPAA compliant subject authorization. All required procedures described in the United States Code and Code of Federal Regulations should be implemented. It is also noted that Subtitle D of the Health Information Technology for Economic and Clinical Health (HITECH) Act, enacted in 2009, extends the privacy and security provisions of HIPAA to business associates of entities using the present invention. Preferably, additional safeguards should also be taken, and every implemented procedure should be continually monitored for technological advances and/or security breaches.

Optionally, some embodiments of the system of the present invention include some form of instruction for the subject when the subject is required to perform specific, prescribed tasks, as opposed to monitoring and measuring movement solely during activities of daily living. These tasks, movements, or activities may be performed in order to calibrate the device, provide baseline measurements, as periodic exercises prescribed by a clinician as part of an assessment or treatment plan, or any other such use or purpose for measuring movement during a structured and known movement or set of movements. The instructions can be presented to the subject in writing, such as a paper given by the clinician, in text form on a video display such as a computer monitor, tablet or smartphone screen, presented via video (recorded, or pre-recorded or live broadcast or streamed video to the subject's video device, again including computer, tablet, phone, television, etc.), or via audio recording, phone call, teleconference, or the like. Preferably, a video or video conference is used which instructs the subjects to perform a series of tasks during which their kinetic motion and/or EMG can be measured. Since the system of the present invention is preferably used in the subject's home, a video giving directions and/or describing various tasks to be performed by the subject can be included with the system or available for streaming or download. The video may be accessed or viewed, for example but not by way of limitation, through use of video tape, DVD, as part of computer software provided, through the internet, or the like. The directions could include but are not limited to instructions on how to don the device, how to turn the device on, and the like. The description of various tasks could include but is not limited to exercises which are typically used by a clinician, physician, therapist or technician to evaluate a subject with movement impairment, injury, movement-affecting conditions or a movement disorder including but not limited to hand grasps, finger tapping exercises, other movements and the like. One embodiment of a video includes the technician, clinician or physician looking into the camera, as they would at a subject, and instructing them on device setup, instructing the subjects through each of the tasks to be performed, providing verbal encouragement via video after a task, and asking subject's to repeat a task if it was not completed. For embodiments for treating or assisting subject's with movement disorders such as Parkinson's disease preferably the technician, clinician or physician instructs the user through multiple tasks as per the UPDRS guidelines including, but not limited to, rest tremor, postural tremor, action tremor, all bradykinesia tasks (including but not limited to finger taps, hand grasps, and pronation/supination tasks), and/or rigidity tasks. More preferably, if the video is linked to the user interface software, the software will automatically detect if a subject has performed the requested task and provide feedback through the video to either repeat the task or continue to the next task.

The present invention may include various methods of measuring and scoring the severity of a subject's disordered or unsafe or undesirable movement, or symptoms of movement disorders. These methods include a number of steps which may include but are not limited to measuring a subject's external body motion; transmitting wirelessly a signal based in part on the subject's measured external body motion; receiving the wirelessly transmitted signal; downloading data from memory; and scoring the severity of a subject's movement disorder based in part on the wirelessly transmitted or downloaded signal. Optionally, an electromyogram of the subject's muscle activity may be obtained and used in part to score the severity of the subject's movement disorder. These steps and quantification methods are described in more detail in U.S. Pat. No. 8,187,209, which has been herein incorporated by reference.

Many embodiments of the present invention involve methods for providing rehabilitation, therapy, training and otherwise aiding a subject improving the safety and quality of his or her movement. These methods, and the devices described herein for performing the methods, can be used to help subjects recover from acute and traumatic injury such as traumatic brain injury or stroke, and the like, or to help treat and manage ongoing conditions, disorders or other movement-related issues, but particularly movement disorders including, but not limited to cerebral palsy (CP), Parkinson's disease (PD) and Parkinsonism, dystonia, chorea, Huntington's disease, ataxia, the many varieties of tremor, myoclonus, tics, Tourette's syndrome, restless leg syndrome, gait disorders, balance disorders, and the like.

Many method embodiments of the present invention include a step of providing a portable therapy system or device to a subject. The portable therapy system or device preferably, as described herein, comprises at least one sensor having a signal, a processor comprising an algorithm and an output, and a cueing or stimulus device. The portable therapy system or device may be a single enclosure with all components embedded, integrated or otherwise contained within or attached to the single enclosure. Alternatively, the portable therapy system or device may comprise an electronics housing or enclosure with the at least one sensor(s) place radially on one or more parts of the subject's body and in communication, either wired or wireless, with the electronics housing or enclosure. The signal of the at least one sensor may also depend on the particular embodiment utilized. In some embodiments, the signal from the at least one sensor may be related to the subject's movement, may be related to voluntary and/or involuntary movement, and may be as specific as movement of a particular limb or portion of the subject's body, or as general as overall movement of the subject's body as a whole. In other embodiments, the signal of the at least one sensor may be related to a subject's balance or stability. The signal of the at least one sensor may depend on the particular sensors used (e.g., accelerometer and gyroscope as opposed to EMG electrode), the placement of the sensor(s), or the particular impairment, condition or disorder for which the device is being used to provide therapy, training and/or treatment. Similarly to the at least one sensor, the cueing or stimulus device may also be embedded, integrated or otherwise attached to the portable therapy system or device or may be a separate component in communication with the electronics housing or enclosure. The exact nature of the portable therapy system or device depends on the particular use. By way of non-limiting example, in an embodiment used for monitoring and helping a subject improve his or her balance, the portable therapy system or device may include all components in a single enclosure, including at least one sensor and the cueing or stimulus device, and might be worn inconspicuous about the subject's chest attached to a strap or harness. Such a device may require at least one gyroscope and/or at least one accelerometer, which can be installed into the device enclosure of the therapy device, and the cuing or stimulus device might be a vibrational motor similarly installed into the device enclosure. When the system of this exemplary embodiment detects an imbalance in the subject based on the gyroscope and/or accelerometer measurements and signals, the vibrational motor would activate and provide a cue to the subject by vibrating, thus indicating to the subject that he or she is losing balance so that the subject can focus on his or her balance and correct the potentially dangerous movement. Alternatively, in another non-limiting example, the sensors may include electromyogram electrodes placed on the subject's arms or legs to measure the muscle movement therein, and the device enclosure may be a centralized unit attached to or carried by the subject while in communication with the remote sensors. The cueing device in such example might be an audio signal generator and thus be integrated into the device enclosure. In this example, the remote sensors measure the subject's muscle movement and transmit their signals back to the device enclosure which, upon determining the presence of a movement disorder symptom, for example, triggers the cueing device to emit an audio signal to the subject to focus on the symptomatic body part or movement and correct the issue.

In any such embodiment of the portable therapy system or device must first be provided to the subject. Providing the device to the subject may require a nominal amount of training, instruction or assistance to familiarize the subject with the device and its use. Such training may occur in the clinical setting where a physician, clinician, therapist or technician guides the subject in the donning, doffing and use of the portable therapy system or device and the particular or various embodiments that the particular subject may utilize. Alternatively, or in addition, video, audio or telecommunication instruction may be made available to the subject such that the subject may become acquainted with, or reacquainted with, the instructions for use of the device outside of the clinical setting, and thus not requiring a special, separate clinical appointment for retraining or recollection on the use of the device. Such non-clinical instruction may be provided through video medium (e.g., DVD, video file provided through a smartphone or tablet application) provided with the device, audio recording (e.g., .mp3 format sent to subject for remote access, on the portable device itself, provided through a smartphone or tablet application), or through teleconference or video conference whereby the subject interacts directly with the physician, clinician, therapist or technician and is walked through the use and operation of the device. Such initial and ongoing training, instruction or assistance ensures that the subject is always able to safely, properly and effectively use the system.

Once the portable therapy system or device has been provided to the subject and the subject is comfortable and knowledgeable as to the use of the device, the subject may then utilize the system in the manner best fitting his or her particular needs, preferably as discussed and agreed upon with the physician, clinician, therapist or technician. The subject preferably is able to use the portable therapy system or device, including all physical and electrical parts, including donning and doffing the device and navigating any software, user interface or other interactive and/or virtual components of the system required to effectively and safely measure the subject's movement and provide the particular desired outcome, whether it be treatment, therapy, training, or any other such output the system is able to provide.

Many method embodiments of the present invention include another step of measuring the subject's movement, or some kinematic feature thereof, with the at least one sensor of the portable therapy system or device. This movement measurement step is performed using the various sensors described herein to measure the subject's body motion. As noted, typical sensors may include at least one of, or combinations of, gyroscopes, accelerometers, EMG electrodes, magnetometers, resistive bend sensors, load cells, and the like. The various sensors can be placed on any part of the subject's body such that the sensor can measure the movement of that part of the body and effectively provide movement data that can be used to predict or determine unsafe, undesirable or symptomatic movement of that part of the subject's body. The sensors acquire their respective signals and transmit those signals to the electronic components of the portable therapy system or device. The particular transmission method determines on the format of the particular embodiment. As noted herein, some embodiments may include sensors embedded in, integrated in or attached to the device enclosure of the portable therapy system or device and thus the device enclosure would likely include internal hard-wired communication circuitry between the sensor(s) and the electronics of the device, and other embodiments may include separate, remotely-placed sensors which may utilize wires or cords to connect the sensors to the electronics in the device enclosure or, more preferably, communicate wirelessly with the electronic components. Wireless communication requires at least one electronic component for transmission of the signal from the sensor and at least one electronic component for receiving the signal by the device enclosure. Preferably, such wireless communication components are each capable of two-way communication such that the remotely-placed sensors and the electronics of the portable therapy system or device are each capable of transmitting and receiving signals and data to and from each other. This is preferable for embodiments wherein the cue or stimulus is provided in a specifically targeted manner to a particular body part, and thus allows the device to provide a cue or stimulus directly through one of the remotely-placed sensors.

Preferably, the step of measuring the subject's movement is performed substantially continuously. By substantially continuously, it is meant that preferably, while the subject is wearing the portable therapy system or device, the device and its sensors effectively monitor the subject's movement constantly as opposed to taking intermittent or periodic measurements, and as opposed to only measuring during a particular task or function. This substantially continuous measurement effectively means to support real-time movement measurement while the subject goes about performing activities of daily living rather than being a clinical device for measurement of measurement at predetermined times, during predetermined activities or tasks designed for clinical purposes. Instead, the portable therapy system or device of the present invention is intended to be a therapy, training and improvement tool constantly monitoring the subject's movement to help predict and detect unsafe or undesirable movements or conditions, and ideally prevent them and train the subject to prevent or avoid them. Real-time for purposes of movement measurement is meant to fit within the preferred ranges and constraints defined above. With respect to substantially continuous measurement of the subject's movement, it is meant that preferably the sensor(s) of the portable therapy system or device acquire movement data once every 60 seconds. More preferably the sensor(s) of the portable therapy system or device acquire movement data once every 30 seconds. Still more preferably the sensor(s) of the portable therapy system or device acquire movement data once every 10 seconds. Even more preferably the sensor(s) of the portable therapy system or device acquire movement data once every second. Still yet more preferably the sensor(s) of the portable therapy system or device acquire movement data once every 0.5 seconds. Even still more preferably the sensor(s) of the portable therapy system or device acquire movement data once every 100 milliseconds. Yet even more preferably the sensor(s) of the portable therapy system or device acquire movement data once every 50 milliseconds. Even yet more preferably the sensor(s) of the portable therapy system or device acquire movement data once every millisecond. Most preferably the sensor(s) of the portable therapy system or device acquire movement data at intervals less than 1 nanosecond. Such continuous measurement intervals may, in some embodiments, also include not only acquisition and measurement of movement data but also transmission of the signal from the sensor(s) to the electronics of the portable delivery system.

The present invention measures movement or a kinematic feature of movement in order to recognize in that movement data impaired gait, balance, posture and movement patterns and to trigger cues to correct, prevent or otherwise address the behavior based on the recognized impairment. Such recognition is based upon extracting various kinematic features from the movement data acquired by the sensor(s) of the system. Kinematic features used to characterize movement may include swing and stance phase, hip circumduction, gait asymmetry, trunk orientation, variability of movement or position, disruption of movement patterns, asymmetry between limbs, and the like, and are preferably extracted and analyzed in real-time.

The actual movement or kinematic feature of movement measured depends on the particular embodiment utilized. Some embodiments are aimed at helping a subject address balance or stability issues, perhaps arising from TBI, stroke, or any other injury or disorder. In such embodiments, the measuring step preferably performs a measurement of the subject's stability or balance, for example by the use of the portable therapy system or device and/or at least one sensor being worn about the subject trunk or torso and being used to measure trunk angle and acceleration. The system can then further measure or determine a variability measure indicating how rapidly the subject's trunk measurements are changing. This measurement taken in reference to the movement of the subject's torso might indicate that the subject is experiencing an imbalance or unstable movement or motion. In another example, for a subject who may have suffered a stroke, TBI or has a movement disorder and suffers from foot drop or dragging leg, the measuring step is preferably performed by measuring kinematic features of the subject's gait and leg movement, and may also utilize balance and stability measures as well. The system might measure hip circumduction to determine if the subject is compensating and thus changing his or her gait, asymmetry to determine whether compensation is occurring compared to the unaffected limb, or any other combination of measures. Measurement methods depend on the particular embodiment, and the particular measurements required to treat a subject's individualized needs.

As noted, movement measurement may actually involve the measurement of a specific kinematic feature of the subject's movement. Again, the measured movements, or kinematic feature thereof, depend on the embodiment, but many such features can be described generally and measured for different parts of the subject's body and in combination with any of the other movement or kinematic features. Clearly, various sensors of the present invention render certain aspects of the subject's movement to be automatically measured, for example accelerometers measure acceleration of the particular body part to which they are attached, and gyroscopes measure orientation based on angular momentum. Similarly, EMG sensors measure electrical activity of muscles. However, additional kinematic features may be measured by these or other sensors, or derived from the measurements and data of these or other sensors. These additional kinematic features provide a more detailed picture of exactly what movements and motions the subject's body is performing, and can provide either a very narrow, specific view of a certain body part or muscle, or a broad picture of the subject's body as a whole. The many embodiments of the present invention utilize the measured and derived kinematic features in many different combinations based on the particular needs of a particular subject.

One such kinematic feature that may be measured or derived from movement data acquired by the sensor(s) is stability, or instability. Balance is a similarly related measure, and can be differentiated from stability/instability by the fact that balance is typically a direct measurement or derivation from accelerometer and/or gyroscope data and can be correlated to clinical scales such as the Berg Balance Scale and the Timed Up and Go test. Stability/instability is a derived kinematic feature extracted or derived from the same measured sensor data, but can further be described as a derivation or analysis of the balance feature. Stability/instability will preferably be a determination based on sensor data or another kinematic feature compared against a predetermined threshold determined to be indicative of the threshold between stability and instability. In other words, when a particular kinematic feature or set of kinematic features exceeds a predetermined threshold, or set of thresholds, the system will determine that the subject is experiencing instability. Therefore, for the purposes of the present invention, this kinematic feature will be referred to as instability, given that instability is impairment portion that the system is aiming to detect, prevent and help the subject improve or overcome. Thresholds used to determine instability will depend on the particular features used to provide the measure of instability.

One directly measured or derived kinematic feature that can be used to provide a measure of instability is trunk orientation or trunk angle. Trunk orientation is typically measured by a gyroscope attached to or worn about the subject's trunk and measures just that, orientation of the subject's trunk. Additionally, trunk orientation can be measured by an accelerometer measuring acceleration from vertical, thus indicating a rapid change in trunk orientation. Still further, trunk orientation can be more accurately measured by a combination of accelerometer(s) and gyroscope(s). Trunk orientation measurement allows the system of the present invention to detect the angular position, preferably with respect to the vertical perpendicular axis to the ground, in which the subject's trunk is oriented. As subsequent measurements of trunk orientation are obtained, the system can continuously monitor the position or orientation of the subject's trunk. Trunk orientation is particularly useful for embodiments that are aimed at, at least partially, monitoring and helping the subject to improve balance or stability and for monitoring and/or decreasing fall risk, though can be used in any other embodiment to help any variety of therapy, monitoring or improvement of the subject's movement. In many embodiments, the algorithms compare the measured trunk angle against a predetermined threshold as a step in detecting or measuring instability of the subject, and when the trunk angle exceeds that predetermined threshold, the subject's movement is considered impaired. Preferably, the subject or the subject's movement can be identified as unstable and differentiated from stable movement at measured trunk angles exceeding 45 degrees from vertical. More preferably, the subject or the subject's movement can be identified as unstable and differentiated from stable movement at measured trunk angles exceeding 40 degrees from vertical. Yet more preferably, the subject or the subject's movement can be identified as unstable and differentiated from stable movement at measured trunk angles exceeding 35 degrees from vertical. Still more preferably, the subject or the subject's movement can be identified as unstable and differentiated from stable movement at measured trunk angles exceeding 30 degrees from vertical. Even more preferably, the subject or the subject's movement can be identified as unstable and differentiated from stable movement at measured trunk angles exceeding 25 degrees from vertical. Yet still more preferably, the subject or the subject's movement can be identified as unstable and differentiated from stable movement at measured trunk angles exceeding 20 degrees from vertical. Still even more preferably, the subject or the subject's movement can be identified as unstable and differentiated from stable movement at measured trunk angles exceeding 18 degrees from vertical. Even yet more preferably, the subject or the subject's movement can be identified as unstable and differentiated from stable movement at measured trunk angles exceeding 16 degrees from vertical. Yet even more preferably, the subject or the subject's movement can be identified as unstable and differentiated from stable movement at measured trunk angles exceeding 15 degrees from vertical. Still yet more preferably, the subject or the subject's movement can be identified as unstable and differentiated from stable movement at measured trunk angles exceeding 14 degrees from vertical. Even still more preferably, the subject or the subject's movement can be identified as unstable and differentiated from stable movement at measured trunk angles exceeding 13 degrees from vertical.

Variability is yet another additional measure that is very useful in many embodiments of the present invention. Variability is a measure of how much a particular measure, metric, or kinematic feature changes from one measurement to the next. Depending on the particular kinematic feature of interest, variability of the feature may be derived from subsequent measurements of a single sensor (e.g., amount or rate of change of gyroscope measurements) or a from combinations of sensors (e.g., combining accelerometric and gyroscopic measures to determine the acceleration of orientation change). By way of non-limiting example, variability may be explained in light of the kinematic feature of trunk orientation or angle. In embodiments where trunk orientation or angle is a kinematic feature of interest, the system may measure or derive the variability of trunk orientation in order to determine how rapidly and to what degree the trunk orientation changes between subsequent measurements or derivations. In these embodiments, such variability allows the system to monitor and detect rapid changes in the subject's trunk angle and can help determine if the subject is swaying rapidly, losing balance or is otherwise unstable. Such measurements can be used to provide a cue to the subject in order to focus on posture and stability, and may additionally be used to detect various symptoms of movement disorders or even to detect other unsafe conditions, such as if the subject is suffering a seizure, for example. Variability may be derived from any single sensor measurement or kinematic feature, or combinations thereof. Variation of any such feature or combination of features provides the very important ability to detect rapid and sudden changes in those features, thus providing the ability to detect or potentially even predict the movement impairment, instability, symptoms of movement disorders, or any other variety of unsafe or undesirable movement.

Many kinematic features used in many embodiments of the present invention center around gait measurements or derived measurements. One kinematic feature measured or derived in many embodiments is gait phase. Identification of gait phase allows the system to determine, in real-time, whether the subject is currently in swing phase of the gait cycle (one foot is in the air for limb advancement) or stance phase (the limb is in contact with the ground). Preferably, gait phase identification is preformed individually and simultaneously for each separate leg, thus being able to identify that one leg is in swing phase and one leg is in stance during gait. Gait phase identification allows the system to utilize additional metrics or kinematic features to detect and monitor impairments in the leg based on the gait phase, and to provide cues to the subject based on those metrics or features. For example, when a leg is in stance phase, the system would know to monitor and measure for stability and balance impairments that could cause the subject to fall while that leg is supporting his or her body; and while in swing phase, the system would monitor and measure for abnormal hip circumduction (see below), proper joint flexion (knee, ankle, hip), tremor, rigidity or other movement disorder symptoms in the leg, and the like. These are merely examples of the various kinematic features that can be measured and monitored in each leg during gait to help a subject improve the quality and safety of his or her gait, and which are preferably performed automatically by the system, continuously, and in real-time.

Also related to gait phase is the feature of phase duration. Once a particular leg's gait phase has been identified, the duration of time during which it is in that phase can be measured. Thus, the system would know when the particular gait phase ends for each leg, and automatically switch to measuring the pertinent metrics or kinematic features associated with the opposite gait phase. Additionally, gait phase time is an important metric in and of itself as it can provide an indication of issues with the subject's gait rather than just an indicator of what other kinematic features or metrics to monitor and measure.

Gait phase duration may provide an indication of a disruption in gait pattern. An increased gait phase in one leg may indicate some other impairment in the function and movement of that leg, for example a symptom of a movement disorder (e.g., rigidity in a particular leg may lead to increased swing phase duration). Thus, gait phase duration, and derivations thereof such as ratio of swing to stance duration (see below) and the like, are all important kinematic features that may be measured or derived by the system. Additionally, although the above gait-related kinematic features were discussed in terms of leg movement kinematic features, such kinematic can also be measured for the arms given that the subject's arms also play a role in maintaining gait-related movements. Similarly, hands, feet, trunk, head and other individual parts of the subject's body may provide important and useful kinematic features or metrics that may be useful for gait-related analysis.

Still another kinematic feature related to gait, and particularly to gait phase duration is asymmetry. Kinematic or movement asymmetry refers to a difference in the same movements of kinematic features of movement performed by complementary balancing limbs or extremities, typically differences between the same movement or kinematic feature in each leg (e.g., differences in each leg's duration of swing phase) and can be measured directly or derived from acquired movement data. Asymmetry between limbs, and particularly gait phase asymmetry, much like phase time, is a very valuable kinematic feature or metric that can indicate the existence or occurrence impairments in movement and can help to identify unsafe or undesirable movement or movement conditions of the subject in order to better cue the subject to improve his or her movement. Asymmetry, and more particularly gait phase asymmetry, can be evaluated by performing sequential steps involving several other kinematic feature measurement or derivation steps along the way. A likely first step is to identify phases of the gait cycle, and can be performed using a peak-to-peak analysis of biopotential signals (i.e., EMG signals) or from other sensor data acquisition. Once gait phase has been identified, the gait phase duration can be measured. Stance-to-swing ratio is a value that can be computed or derived from the gait phase duration measurement and provides an indication of the normalcy or level of impairment of the subject's gait or other bilateral movement patterns. A normal or unimpaired subject can expect to exhibit a stance-to-swing ratio of around or about 60:40, whereas some reports have shown that an individual with stroke exhibits an increase in swing phase duration and thus have a stance-to-swing ratio closer to 50:50. More important than an individual limb's stance-to-swing ratio, however, is the symmetry ratio which compares the same phase for each complementary or balancing lime, that is for example, swing duration for each the left and right leg. The symmetry ratio (SR) is preferably measured by the ratio presented in EQ. 1:

$$\text{Symmetry Ratio}(SR) = \frac{\text{Swing Time}_{impaired\ Side}}{SwingTime_{Non-impaired\ Side}} \quad \text{EQ. 1}$$

Thus, the symmetry ratio is a measure of the difference between the same phase of opposite limbs or extremities and provides a quantification as to the severity of the impairment in one of the limbs or extremities. When the SR exceeds a predetermined threshold, the subject's movement is considered impaired. Preferably, movement is flagged or identified as being impaired when the SR value is greater than 2. More preferably, movement is flagged or identified as being impaired when the SR value is greater than 1.9. Still more preferably, movement is flagged or identified as being impaired when the SR value is greater than 1.8. Yet more preferably, movement is flagged or identified as being impaired when the SR value is greater than 1.7. Even more preferably, movement is flagged or identified as being impaired when the SR value is greater than 1.6. Still yet more preferably, movement is flagged or identified as being impaired when the SR value is greater than 1.5. Even still more preferably, movement is flagged or identified as being impaired when the SR value is greater than 1.4. Yet still more preferably, movement is flagged or identified as being impaired when the SR value is greater than 1.3. Even yet more preferably, movement is flagged or identified as being impaired when the SR value is greater than 1.2. Yet even more preferably, movement is flagged or identified as being impaired when the SR value is greater than 1.1. Still even more preferably, movement is flagged or identified as being impaired when the SR value is greater than 1.05.

Circumduction is the conical movement of a particular body part, and is a particularly useful kinetic feature of movement utilized in many embodiments of the present invention, generally regarding circumduction of the limbs or extremities. Circumduction involves a combination of all axial movements (flexion, extension, adduction and abduction) in coordination to perform a preferably smooth, fluid conical motion. Measurement of circumduction, or more accurately and specifically the measurement of any circumduction compensation strategy the subject employs, allows the system to determine if there are impairments or disturbances in such circumduction motion that can lead to instability, imbalance, generally unsafe or undesirable movement or motion, or may be indicative of a movement disorder or other disease or disorder. Normal, unimpaired movement in the average subject exhibits an average hip abduction angle of approximately 3.9 degrees during both unimpaired gait and swing of the non-affected limb. Conversely, subjects with stroke have been observed to exhibit hip abduction angles that are significantly increased—averaging about a 9.8 degree hip abduction angle in the movement of the affected limb. Circumduction, or hip circumduction, compensation strategies utilized by the subject can be identified by measuring the magnitude of coronal plane hip abduction angular velocity during the swing phase of the subject's gait. Integrating angular velocity into the basic hip abduction angle measurement allows the present invention to provide a measure for the hip circumduction compensation strategy which can better help the system detect or predict impairments or disorders in movement and provide appropriate cues to address the abnormalities. Hip circumduction strategy can be identified when the measured or calculated magnitude of coronal plane hip abduction angular velocity during swing phase exceeds a predetermined threshold value. Preferably, circumduction compensation strategy is identified by an abduction angle greater than 10 degrees. More preferably, circumduction compensation strategy is identified by an abduction angle greater than 9 degrees. Yet more preferably, circumduction compensation strategy is identified by an abduction angle greater than 8 degrees. Still more preferably, circumduction compensation strategy is identified by an abduction angle greater than 7 degrees. Even more preferably, circumduction compensation strategy is identified by an abduction angle greater than 6 degrees. Yet still more preferably, circumduction compensation strategy is identified by an abduction angle greater than 5.8 degrees. Still yet more preferably, circumduction compensation strategy is identified by an abduction angle greater than 5.6 degrees. Even still more preferably, circumduction compensation strategy is identified by an abduction angle greater than 5.4 degrees. Yet even more preferably, circumduction compensation strategy is identified by an abduction angle greater than 5.2 degrees. Still even more preferably, circumduction compensation strategy is identified by an abduction angle greater than 5 degrees. Even yet more preferably, circumduction compensation strategy is identified by an abduction angle greater than 4.5 degrees.

Measurement or acquisition of data corresponding coordination of movement in joints is another important capability and measure or kinematic feature of the present invention. Clearly, even on a scaled-back view (i.e., ignoring inner workings and complex biomechanical and anatomical details) most of the human body's movements require complex coordination of numerous body parts, muscles and joints to act in concert to achieve a fluid, normal motion. Measurement of movement, if taken on too small of a scale, for example focused on merely a single body part without concern for what the coordinating body parts are doing, may not paint the entire picture and may lead to inaccurate detection and monitoring of impairments and thus improper cueing. Instead, many embodiments of the present invention attempt to measure and monitor the movement of multiple, coordinated parts of the body, and/or coordination of joint movement in order to provide that complete picture. Particularly when it comes to measuring movement that is part of a therapy or treatment plan, such measurement and monitoring is important to avoid compensation strategies from being utilized or from tricking, and also to help prevent hyperextension or other injuries of movement from the therapy or stretching. For example, if a subject is rehabilitating an elbow injury, and the system embodiment uses only a handheld or hand mounted sensor(s), the subject can merely rotate his or her hand to trick the system into believing that the subject performed full range of motion rehabilitation exercise for the elbow. Measuring and monitoring joint coordination allows the system to detect that the subject is perform a full motion with the entire affected or prescribed part of the body and is thus receiving the proper therapy. Though that example focuses on therapeutic or treatment embodiments, the same principles apply to detection and monitoring embodiments. Joint coordination provides a larger picture that ensures the full and proper movement of the subject thereby leading to increased safety and efficiency of movement, as well as maximizing the therapeutic and treatment effect of movement-related activities.

Some embodiments of the present invention further are capable of measuring, detecting and/or monitoring abnormal muscle synergies as well. Muscle synergy is related to joint coordination in the sense that it describes or is a measure of the coordination between attached or complementary muscles and the way they work together to carry out more complex movements. Abnormal muscle synergies can arise as a result of movement impairment, compensation to overcome impairment, injury, disorders, or any other condition or event that causes muscles to exhibit abnormal synergy or coordination with their partners or counterparts. Embodiments of the present invention that are able to detect, measure and monitor abnormal muscle synergies do so in an effort to provide a subject with a cue or stimulus to correct or overcome the abnormal synergy and to focus on rehabilitation, training or therapy to help restore normal muscle synergy and thus normal movement or motion of those muscles and joints and the corresponding body parts. Thus, muscle synergy, with a focus on detecting abnormalities therein, is yet another kinematic feature, or combination of other separate kinematic features, that some embodiments of the invention may measure, derive and monitor in order to provide cues or stimuli to help the subject improve the quality and safety of his or her movement or motion.

By virtue of measurement of the many and various kinematic features and metrics described herein as well as others that would be obvious to one of skill in the art, many embodiments of the present invention further monitor, measure and/or detect when the subject is using compensation strategies to avoid impaired movement or symptoms of movement or other disorders. More specifically, such embodiments measure and monitor the kinematic properties of the subject's movement in order to detect when compensation strategies are being used. Compensation strategies are the movements that a subject performs to replace the full or normal movement that a person not suffering from an impairment would perform. For example, if a subject's shoulder movement is impaired and he or she needs to extend an arm to reach an item, the subject might tilt his or her body toward the item, thus reducing the amount of arm and shoulder movement necessary to reach the item in question. Some embodiments of the present invention are able to detect and determine when such compensation strategies are being utilized. This allows the system to provide appropriate cues or stimuli in order to make the subject aware that he or she is using a compensation strategy, and therefore the subject can focus his or her attention on proper therapy, treatment or attention to the movement to correct the impairment and return to normal motion without requiring compensation. Compensation strategy detection and monitoring further helps track the subject's improvement over time to ensure that the use of compensation is decreasing safely and the subject is working towards normal movement without further injuring the impaired body part. Compensation strategy detection and monitoring typically requires monitoring of numerous kinematic features of multiple parts of the body, and often requires ongoing monitoring and storage of movement data and cueing data.

Still another step of many method embodiments of the present invention includes that of analyzing the movement data with a processor and algorithm to predict or determine gait, balance or posture impairment, instability or imbalance, at least one symptom of a movement disorder, or other such impairments or unsafe or undesirable movements. The processor preferably comprises and algorithm adapted and trained, or trainable, to perform the necessary calculations, for making the desired detections, predictions or determinations. Preferably, the algorithm is at least partially preprogrammed to receive movement data from the at least one sensors included with the particular embodiment, and analyze that data to extract the required kinematic features. Once the kinematic features are parsed out from the acquired movement data, the algorithm compares the measured value against a predetermined threshold in order to determine whether the measured movement exhibits any gait, balance or posture impairment, instability or imbalance, at least one symptom of a movement disorder, or other such impairments or unsafe or undesirable movements. The thresholds for each individual kinematic feature or movement metric can be determined in several ways. Initially, thresholds are preferably predetermined and programmed into the algorithm. In some embodiments, the algorithm may be a single-programming model wherein the values as initially set and programmed into the algorithm are permanent or semi-permanent such that the system and algorithm will operate under those programmed conditions and thresholds perpetually, or until the individual portable therapy system or device and system are reprogrammed to comprise different values. Alternatively, and preferably, the algorithms can either be reprogrammable through direct intervention, or can be learning, trainable algorithms that are designed to change over time based on ongoing or subsequent measurements and acquired movement data. For direct intervention programming or training of the algorithms, the portable therapy system or device may be returned to the clinician, physician, therapist or technician to be reprogrammed or trained, or, more preferably, the reprogramming or training takes place remotely. Remote reprogramming or training may involve electronic communication between the programmer or trainer (i.e., clinician, physician, therapist, technician, or other qualified user) whereby the programmer or trainer may receive movement data and cueing data from the subject's portable therapy system or device or retrieve such data from a database, and/or transmits commands or data to the subject's portable therapy system or device comprising operating controls, algorithm parameters, and the like such that the portable therapy system or device would operating according to the updated controls, commands and parameters after programming or training Such programming or training may be performed as part of a routine checkup process, or as a result of new data or results, and may initiated by the user or the programmer or trainer may remotely interrogate the device and initiate the programming or training. Alternatively, no direct communication may be required between a programmer or trainer and the subject's portable therapy system or device, but rather updates, programming and training may be performed by automated or semi-automated software update. For example, in embodiments where the portable therapy system or device is a subject's smartphone with an associated application for monitoring, analysis and cuing, updates, programming or training of the device (the application) can be performed through automated update of the application, by the subject checking for updates and initiating the update process (either randomly or in response to a clinician's, physician's, therapist's or technician's notification that an update is available), or the programmer or trainer may program an update that can be automatically pushed to the subject's device at a convenient time, for example while the subject is asleep and not utilizing the portable therapy system or device. Further, for any programming, training or updating method, the reprogramming, retraining or updating may be based upon the subject's own personal movement data and/or cuing data, or on a database comprising data from many subjects. Updating the portable therapy system or device and programming or training can operate by the same methods described below in relation to programming therapy or treatment devices such as deep brain stimulation devices. In most embodiments, the system and algorithm operate under the presently programmed parameters and controls while in use, and the algorithm processes the measures movement data according to those parameters to provide an output, said output depending on the particular embodiment.

Another step in many embodiments of the present invention includes transmitting the output of the algorithm to a cuing or stimulus device. The preferred transmission method depends on the particular embodiment of the portable therapy system or device, and may be wired or wireless. In many embodiments, the processor comprising the algorithm and the cuing device are merely different electronic components within the same enclosure or case. For example, in embodiments where the preferred cue is an audible signal, the portable therapy system or device preferably comprises an enclosure, for example a smartphone, with a processor and an algorithm for performing the required calculations, and electronic components for generating an audio signal. In this example, the processor and audio cue generating components are preferably hardwired to each other, or at least to the same or connected boards within the smartphone, and the transmission of the output from the algorithm to the cueing device is through hardwired electrical connections within and between the electronic components of the portable therapy system or device's enclosure. The cueing device, or audio signal generating component, would then generate and provide the cue according to the output of the algorithm. Alternatively, an audio cue may be provided through headphones or the like, in which case the speaker component would deliver the cue directly into the subject's ear(s) preferably. Such communication could be wired or wireless depending on the nature of the headphone or speaker device. In other embodiments, particularly those utilize tactile or physical cueing directed to a particular body part, transmission of the output of the algorithm may need to travel over greater distances than those internal to the enclosure of the portable therapy system or device. In some embodiments this may be through wired communication whereby wires, cables or other physical connections extend from the enclosure to the cueing devices located remotely from the enclosure on the subject's body. In other embodiments, and preferably given the desire for inconspicuous operation of the system, remote cueing devices may be in wireless communication with the electronic components of the enclosure whereby the enclosure comprises at least one electronic component for wirelessly transmitting the output of the algorithm to the remote cueing device(s). The output of the algorithm may thus control one or more cueing devices of any variety to provide any variety of cue to the subject based on the measured or acquired movement data.

Another step in many method embodiments of the present invention includes providing with a cueing or stimulus device a cue or stimulus to the subject based on the output of the algorithm which preferably comprises a prediction or detection of gait, balance or posture impairment, symptom(s) of movement disorder(s) or some other impairment of movement. By this, it is meant that preferably a cue or stimulus is only provided to the subject when such impairment is actually detected or predicted. Cues or stimuli themselves may take on many forms, including audio, visual, physical, instructional or even automated treatment, therapy or assistance methods. Various differentiable cues can indicate different conditions, impairments, predictions, detections, or any other metric or feature the system is designed to detect or output—all in the same embodiment. That is to say that, for example with audio cues, a long high pitch can mean that the system has detected an occurring imbalance in the subject while two short pitches may indicate that the subject is exhibiting a minor gait disturbance. Given that the cues may take on many different forms, some embodiments may require an additional training step or phase prior to actual use of the portable therapy system or device and system whereby the subject is trained to recognize and understand the various types of cues or stimuli, and to be aware of their meanings in order to react to each different cue appropriately with little or no thought or analysis. In other words, in some embodiments the subject preferably is trained to know what many cues mean and to substantially automatically react to prevent, counter or address the issue or impairment that has been predicted or detected giving rise to the cue or stimuli in real-time.

The cues or stimuli are also preferably adaptive. Ideally, if the system detects or predicts an unsafe condition or impairment and provides a cue or stimulus, the subject notices the cue or stimulus, comprehends the meaning, and reacts accordingly to the prediction or determination that that cue or stimulus represents in order to prevent or correct the predicted or determined impairment, unsafe or undesirable movement or condition, symptom, or other such impairment. However, it is conceivable that the subject may not initially notice or immediately comprehend the initial cue or stimulus. The subject may be focused intently on whatever task or activity of daily living her or she is performing, or may not remember what the particular cue or stimulus means. In the event of an ignored or missed cue, the system preferably recognizes that the subject has not reacted to the stimulus or cue (likely by measuring a persistence or worsening of the impairment, condition, symptom, etc.) and repeats the appropriate cue or stimulus. Depending on the urgency of the circumstances, the system can increase the urgency of the cue or stimulus. This can be accomplished by increasing the intensity, duration, frequency or any other such aspect of the cue or stimulus. Additionally, the system may alter or change the method or type of cue or stimulus—such as switching from audio tone to audio message comprising spoken words providing an exact indication of what has been predicted or detected and the proposed instruction to prevent or address the prediction or detection. Many iterations of adaptive cues or stimuli may be imagined by those skilled in the art with the intent that the system adapts the cue or stimulus to ensure that the subject is aware of the predicted or determined impairment, symptom or unsafe or undesirable condition, understands the cue or stimulus, and reacts accordingly to address the issue.

Audio cues or stimuli may take different forms depending on the embodiment, the needs of the subject, or the subject's current environment. Audio cues or stimuli may take the form of a pitch or tone, a series of pitches or tones, a musical progression or series of notes, a chime, a spoken message conveying information, or any other similar form or variety of notifying the subject by sound that the system has detected or predicted impaired movement as described herein. Given that the systems and methods of the present invention are able and preferred to be used during activities of daily living, that is while the subject goes about performing normal daily activities of life, discretion is an important goal of the present invention to help the subject avoid embarrassing reactions and social stigma resulting from noticeable devices or cues being administered. Therefore, preferably audio cues or stimuli are delivered discreetly to the subject and the subject alone such as through personal headphones or similar personal speaker devices. This allows the subject to receive an audio cue without notifying others in the subject's vicinity that the system has detected or predicted impaired movement or that the subject is even utilizing such a system. Sometimes, however, urgency or emergency may override the need for discretion and the system may adapt the cue or stimulus accordingly if the subject is in such urgent need to be notified of a predicted or determined impairment. Some embodiments may change the type or method of audio cueing or stimulation based on the subject's environment, either automatically or by allowing the subject or other user to manually change the settings or parameters. If a subject is not out in public, and thus is not concerned about discreet audio cues or stimuli, for example if the subject is at home or in a vehicle, does not have headphones or personal speakers, or is otherwise not concerned with discretion, the system can preferably output an audible signal through an internal or integrated speaker or audio output device or component. The system may allow the subject or another user (e.g., clinician, physician, therapist, technician, family member, caregiver, etc.) to manually change the settings or parameters and instruct the system to output an audible signal even if personal headphones or the like are not attached. Alternatively, the system may automatically detect the subject's location and can override the discreet signal preferences automatically—such as when the subject enters his or her car and may not be wearing headphones, or is at home. Yet another non-discreet audio cue or stimulus embodiment might allow the system to broadcast the audio cue or stimulus to another device, such as a stereo, car stereo, phone, television, computer or the like to increase the chances that the subject notices and comprehends the audio cue or stimulus as quickly as possible.

Visual cues or stimuli may similarly take on various forms or methods based on the embodiments. A visual cue or stimuli may comprise a single or series of blinking or flashing lights, different colors, various symbols, text messages, or any other such visual indicator designed to catch the attention of the subject. Again, depending on the embodiment, the subject is preferably trained to understand what the various alternative cue or stimulus forms might mean, as well as the alternative intensities of those forms of cues or stimuli. Visual cueing preferably involves the wireless transmission, by at least one electronic component of the portable therapy system or device, to a visual display device. Wired tethering or connection to a visual display may be feasible in some embodiments, such as if the visual display is part of a video game system the subject is playing while stationary, worn on the subject such as in the form of eyewear or a heads up display, or perhaps in a vehicle—in other words only embodiments where the subject is substantially stationary and wired connections are not a hindrance or embarrassment to the subject. Even in those circumstances, however, wireless communication is still preferred when possible. In embodiments that provide visual cues or stimuli, the output of the algorithm is used to trigger the cueing or stimulus to provide a cue or stimuli visually to the subject via a visual display device. A visual display device for providing cues or stimuli may include any of televisions, computer or laptop monitors, tablets, eyewear (e.g., eyeglasses, sunglasses, goggles, standalone devices attached to eyewear, and the like), vehicle windshield, heads up displays, projections, or any other such medium where one could reasonably expect to notice a visual cue or stimulus displayed. Visual cues or stimuli of any variety are preferably displayed in a noticeable, conspicuous manner so as to effectively notify the subject, but not in an invasive or distracting manner such that the subject's attention is completely diverted from whatever task or activity of daily living he or she is performing (e.g., driving).

Tactile or physical cues or stimuli similarly may take on various forms depending on the embodiment and the cue or stimulus needed to alert the subject. The preferred type of tactile or physical cueing or stimulation is surface vibration or motion, such as provided by a vibrational motor attached to the subject or a garment or harness worn by the subject, where the vibrational cue or stimulus is similar to that of the vibration function of a cellular phone. One or more such vibrational motors may be mounted, attached or worn on various locations on the subject's body, and the system can be designed, programmed or trained to provide separate, discreet cues to the various parts of the subject's body using the separate vibrational cueing or stimulation motors. Much like other cueing or stimulation devices herein, the tactile or physical cueing or stimulation devices may be in wired or wireless communication with the portable therapy system or device. Wired communication is feasible though less-preferred given the length and multitude of wires, cords or cables that might be required by some embodiments with many cueing devices, as well as the difficulty in maintaining discretion with multiple wired connections extending to various portions of the subject's body. Therefore, wireless communication is again preferable where the individual tactile or physical cueing or stimulation devices each comprises at least one electronic component for receiving a signal from the portable therapy system or device where the signal comprises the instruction or command to provide the tactile or physical cue or stimulus. Also similar to the other cueing or stimulation devices described herein, the cue or stimulus provided by the tactile or physical cueing or stimulation devices can be altered or adapted to ensure the subject notices the cue or stimulus and acts accordingly. The pattern of the cue or stimulus (e.g., vibration) may be altered, the intensity may be increased or decreased, the frequency changed, and the like, all in order to adapt and ensure the subject receives the message indicated by the cue or stimulus. Other forms of tactile or physical stimulus may also be provided other than vibration. A light electrical current may be applied to the surface of the subject's skin with an electrical pulse generator or other similar device, temperature changes may be applied to the subject's skin using thermoelectric materials or devices or other similar temperature changing devices, or even in extreme or urgent cases a noxious stimulation may be applied to activate the subject's pain response such as by applying a sharp object to the subject, all in order to deliver the appropriate cue or stimulus to the subject, or provide an incremental adaptation of the cue or stimulus where the subject fails or is unable to act accordingly.

Some embodiments of the present invention further provide instructional cues. Instructional cues, for purposes of the present invention, include suggested exercises, stretches, movements, motions, therapy or other tasks for the subject to perform in order to address the impaired or unsafe or undesirable movement. Instructional cues are preferably delivered as either audio or visual cues that provide the subject with sufficiently detailed instruction on the particular exercise, movement, task, etc. to perform. The system may present instructional cues in the form of generated reports that can be displayed on a visual display device, or can be transmitted to the subject in a document format for printing and record keeping. Some embodiments may allow a clinician, physician, therapist, or technician to access the subject's movement and cueing data (e.g., remote interrogation of the subject's portable therapy system or device, transmission of the data to the clinician, or access to a database where the data is transmitted and stored) and can provide instructional cues for the subject to follow. Instructional cuing may be as terse as suggesting the subject corrects his or her posture, or as detailed as providing an exercise regimen and plan tailored to the particular measured, predicted or detected impairments, symptoms or unsafe or undesirable conditions the system recognizes the subject as experiencing. Many embodiments further allow clinician intervention to review the data and alter system-generated instructional cues, in addition to creating an entire instructional cue regimen, thus combining both automated instructional cueing and clinician intervention.

Figure 1B:
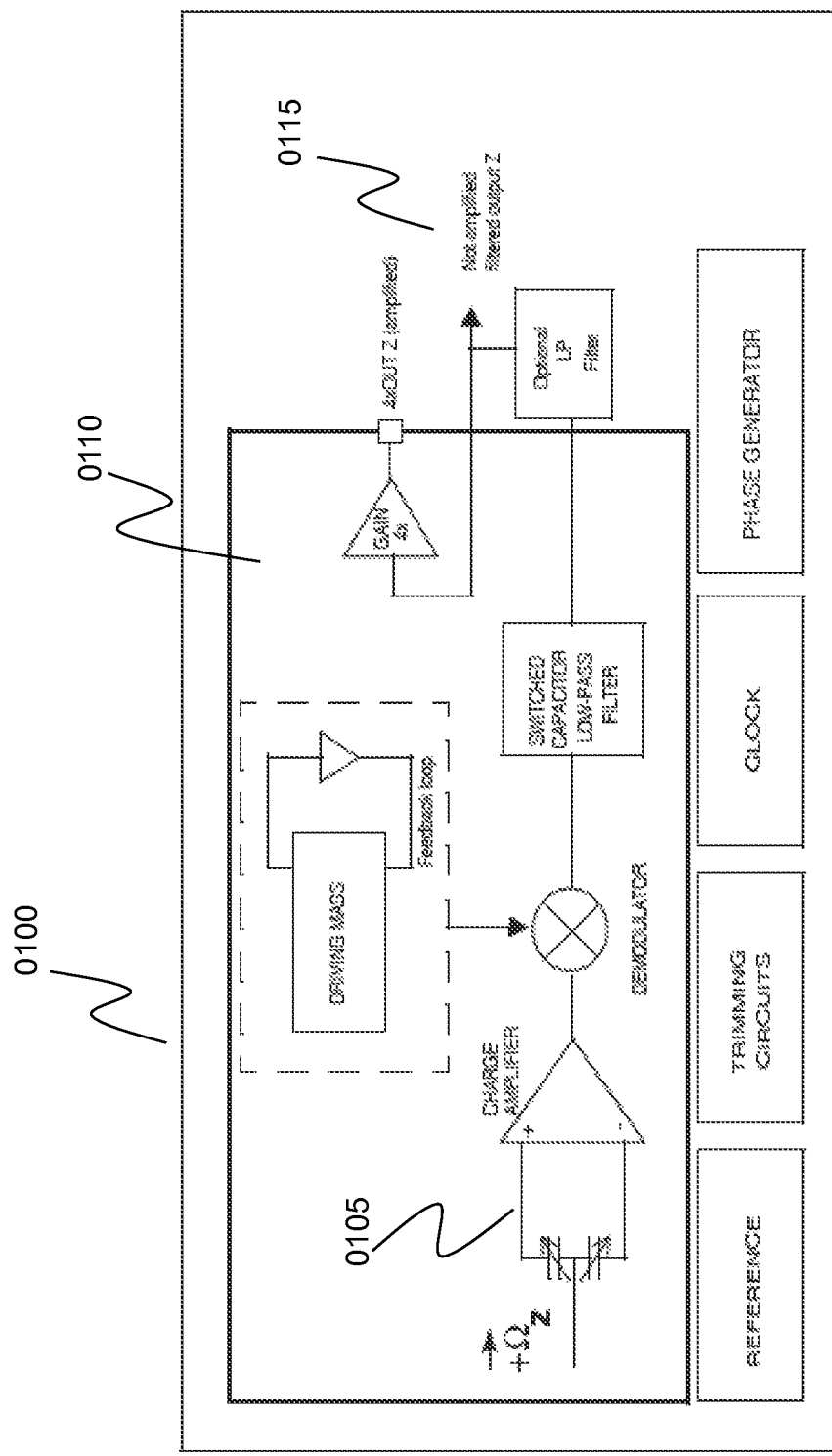
Figure 1C:
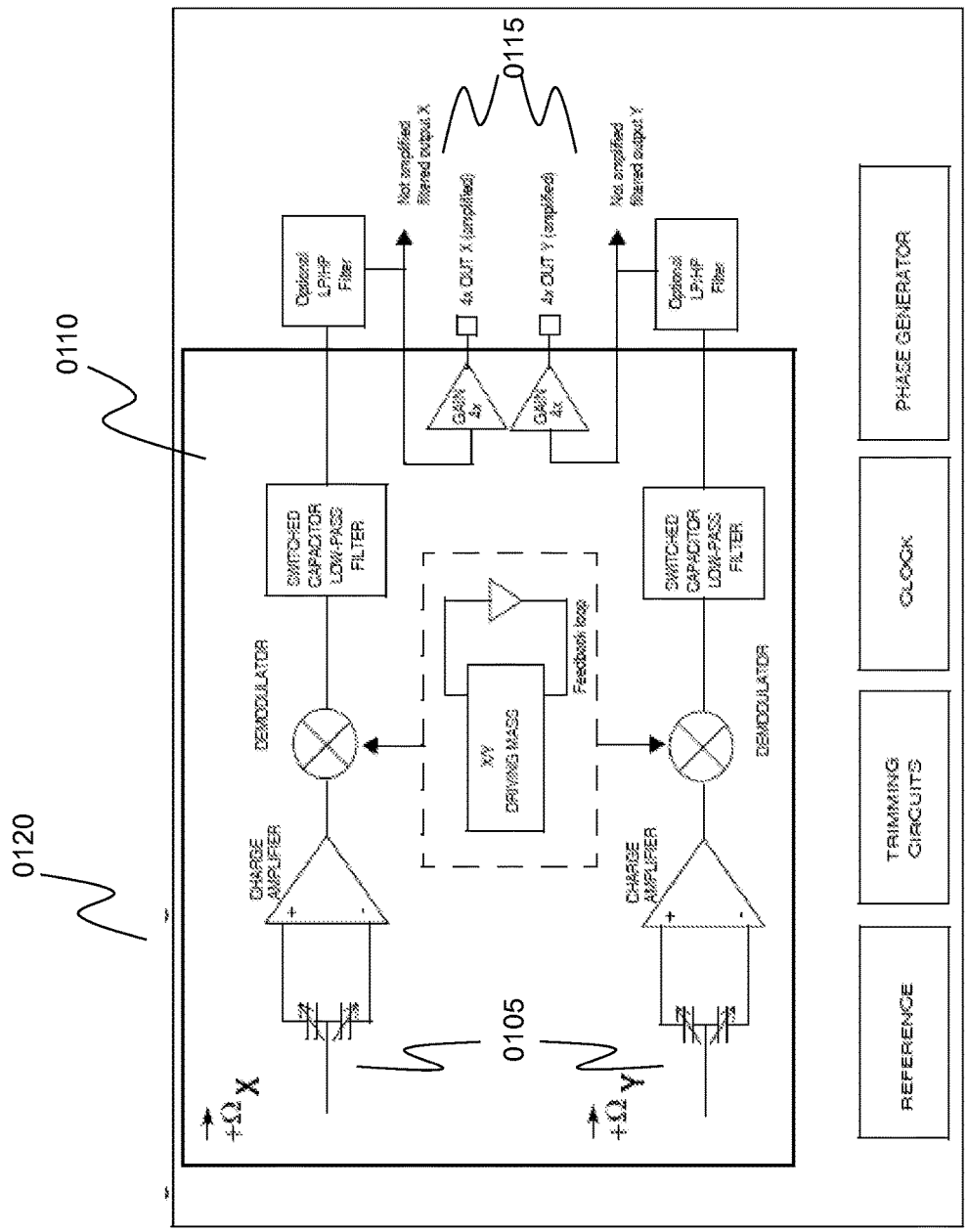

Now referring specifically to the drawings accompanying this specification, FIGS. 1A-1C depict electrical schematics for various optional gyroscope sensors that may be used with the present invention. FIGS. 1A and 1B are electrical schematic diagrams for two embodiments of a single-axis gyroscope 0100 optionally used as a sensor or in a sensor of the present invention. The sensor element 0105 functions on the principle of the Coriolis Effect and a capacitive-based sensing system. Rotation of the sensor 0105 causes a shift in response of an oscillating silicon structure resulting in a change in capacitance. An application specific integrated circuit (ASIC) 0110, using a standard complementary metal oxide semiconductor (CMOS) manufacturing process, detects and transforms changes in capacitance into an analog output voltage 0115, which is proportional to angular rate. The sensor element design utilizes differential capacitors and symmetry to significantly reduce errors from acceleration and off-axis rotations.

FIG. 1C is an electrical schematic for one embodiment of a dual axis gyroscope 0120 also based on the Coriolis Effect as described for FIGS. 1A and 1B. Preferably, the gyroscope used with the present invention is a three-axis gyroscope. The preferred three-axis combination can be achieved by any combination and orientation of three single-axis sensors, a single-axis and dual-axis sensor, most preferably a single three-axis sensor (not shown for a gyroscope), two dual-axis sensors where the repeated axis is averaged, or other combinations and orientations known to those skilled in the art which produce orthogonal yaw, pitch, and roll measurements.

Figure 2A:
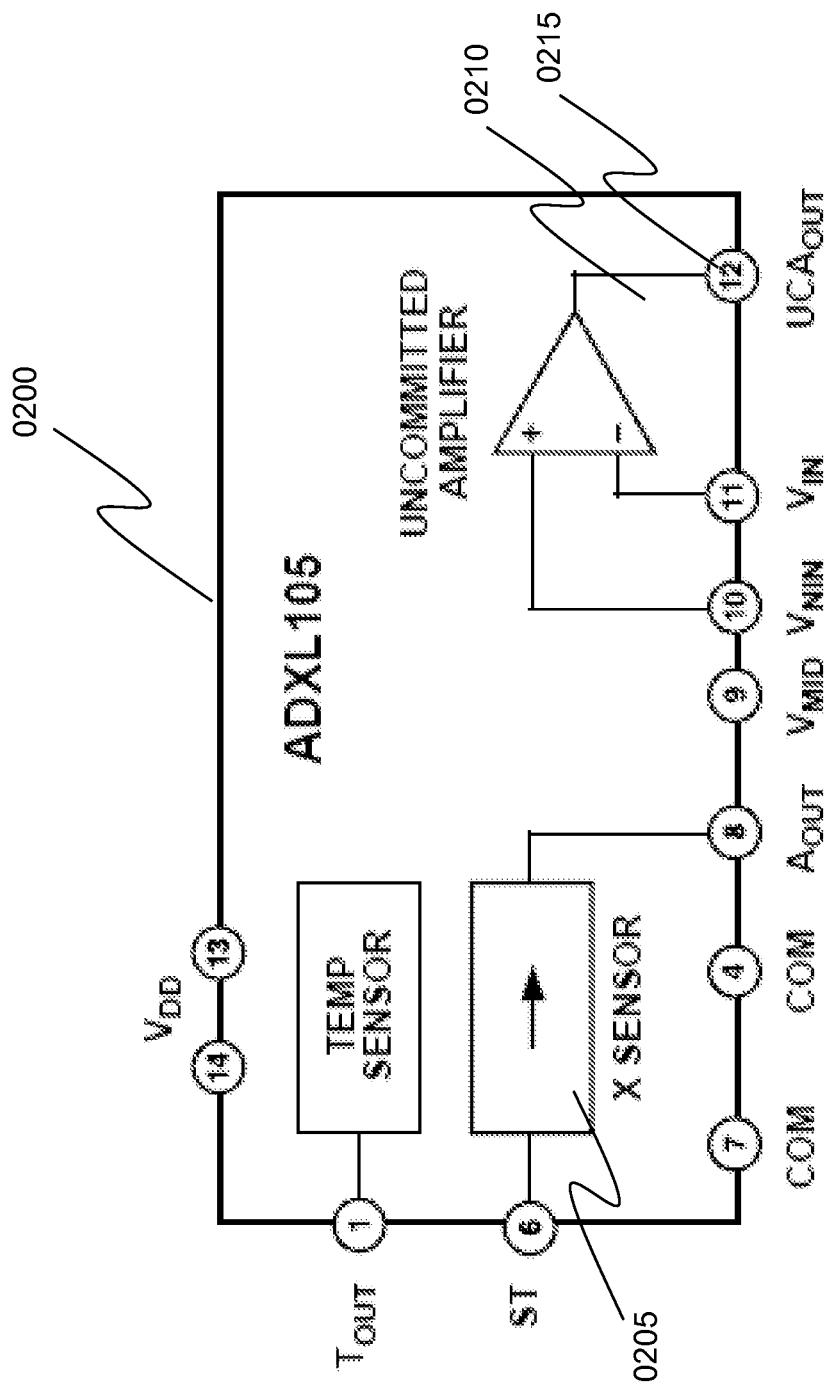
FIGS. 2A-2C. Electrical schematic of a three-axis accelerometer.
Figure 2B:
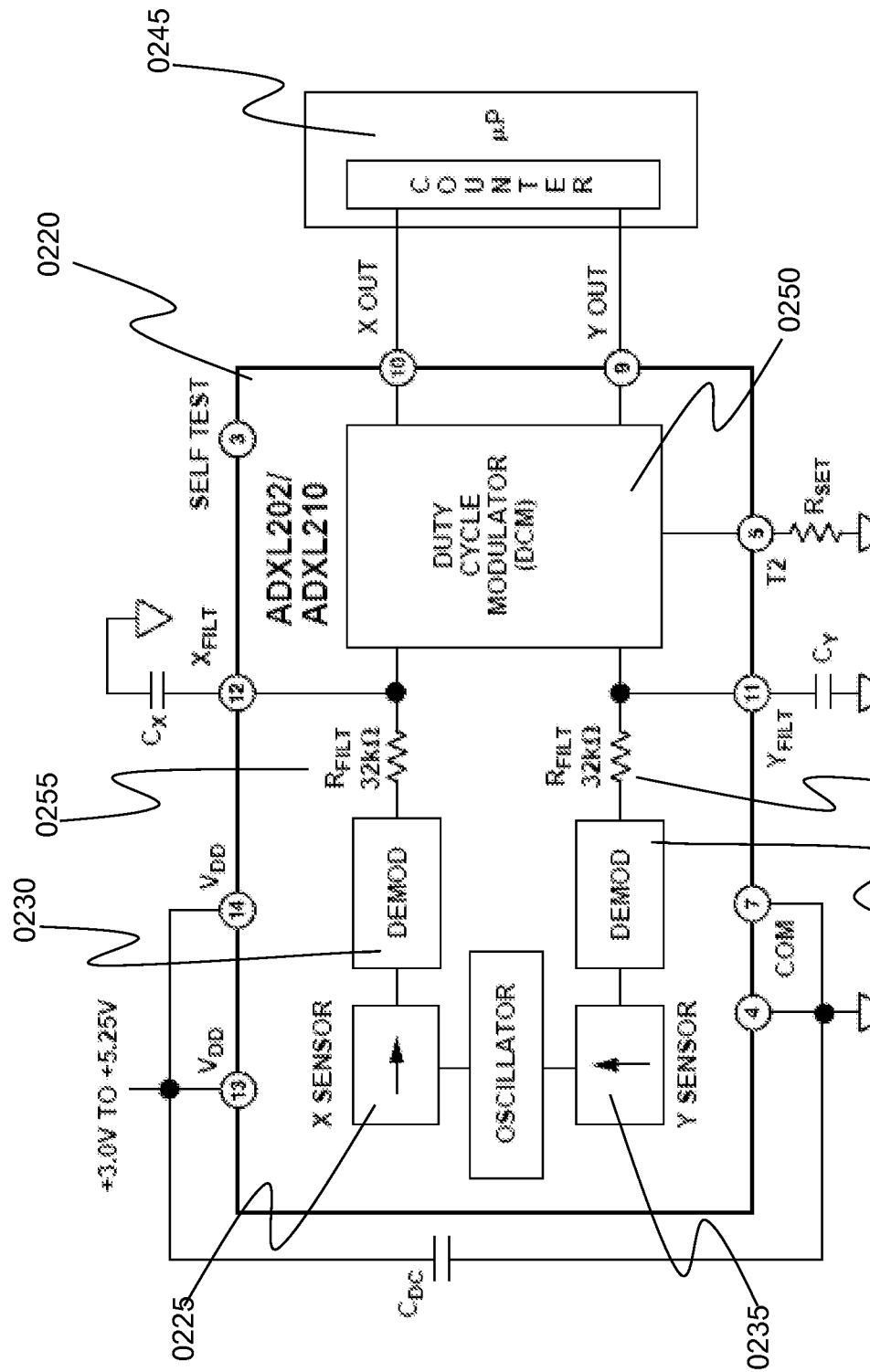
Figure 2C:
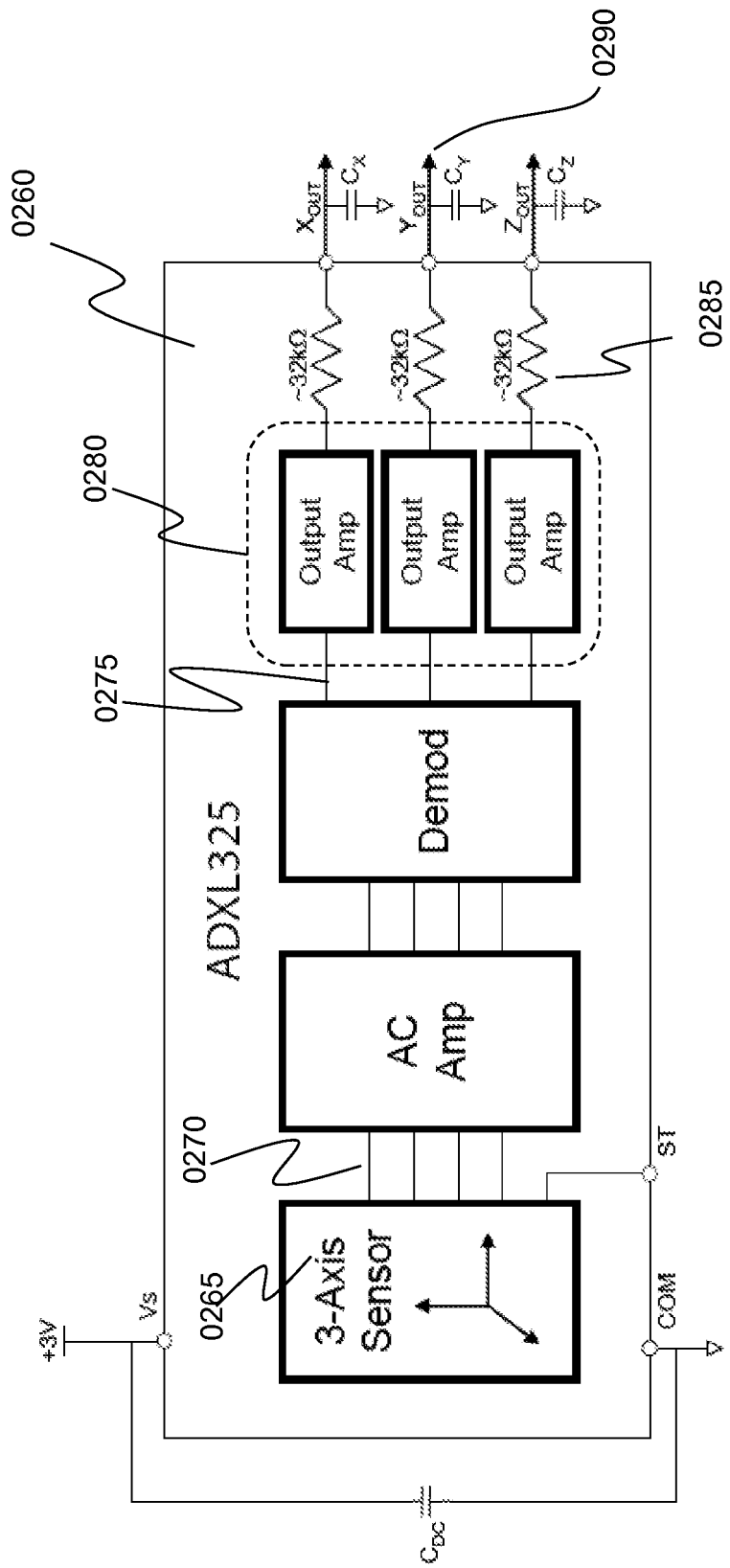

FIG. 2 is an electrical schematic diagram for one embodiment of a preferred three-axis accelerometer of the present invention. The three-axis accelerometer system 0260 contains a to polysilicon surface micromachined sensor 0265 and signal conditioning circuitry to implement an open-loop acceleration measurement architecture. For each axis an output circuit converts the analog signal to a duty cycle modulated (DCM) digital signal that can be decoded with a counter/timer port on a microprocessor. The dual axis accelerometer is capable of measuring both positive and negative accelerations. The sensor is a polysilicon surface micromachined structure built on top of a silicon wafer. Polysilicon springs suspend the structure over the surface of the wafer and provide a resistance against acceleration forces. Deflection of the structure is measured using a differential capacitor that consists of independent fixed plates and plates attached to the moving mass. The fixed plates are driven by 180° out-of-phase square waves. Acceleration deflects the moving mass and unbalances the differential capacitor resulting in an analog sensor output 0270 whose amplitude voltage is proportional to acceleration. Phase-sensitive demodulation techniques are then used to determine the magnitude and direction of the acceleration. The demodulator output 0275 is amplified 0280 and brought off-chip through a 32 kΩ resistor 0285. At this point a pin is available on each channel to allow the user to set the signal bandwidth of the device by adding a capacitor 0290. This filtering improves measurement resolution and helps prevent aliasing. After being low-pass filtered, the analog signal is converted to a duty cycle modulated signal by the DCM stage. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller. As described for gyroscopes, any combinations and orientations of single- (not shown), dual- (not shown), and three-axis accelerometers may be used known to those skilled in the art in order to obtain accelerometric data in three orthogonal directions.

Figure 3A:
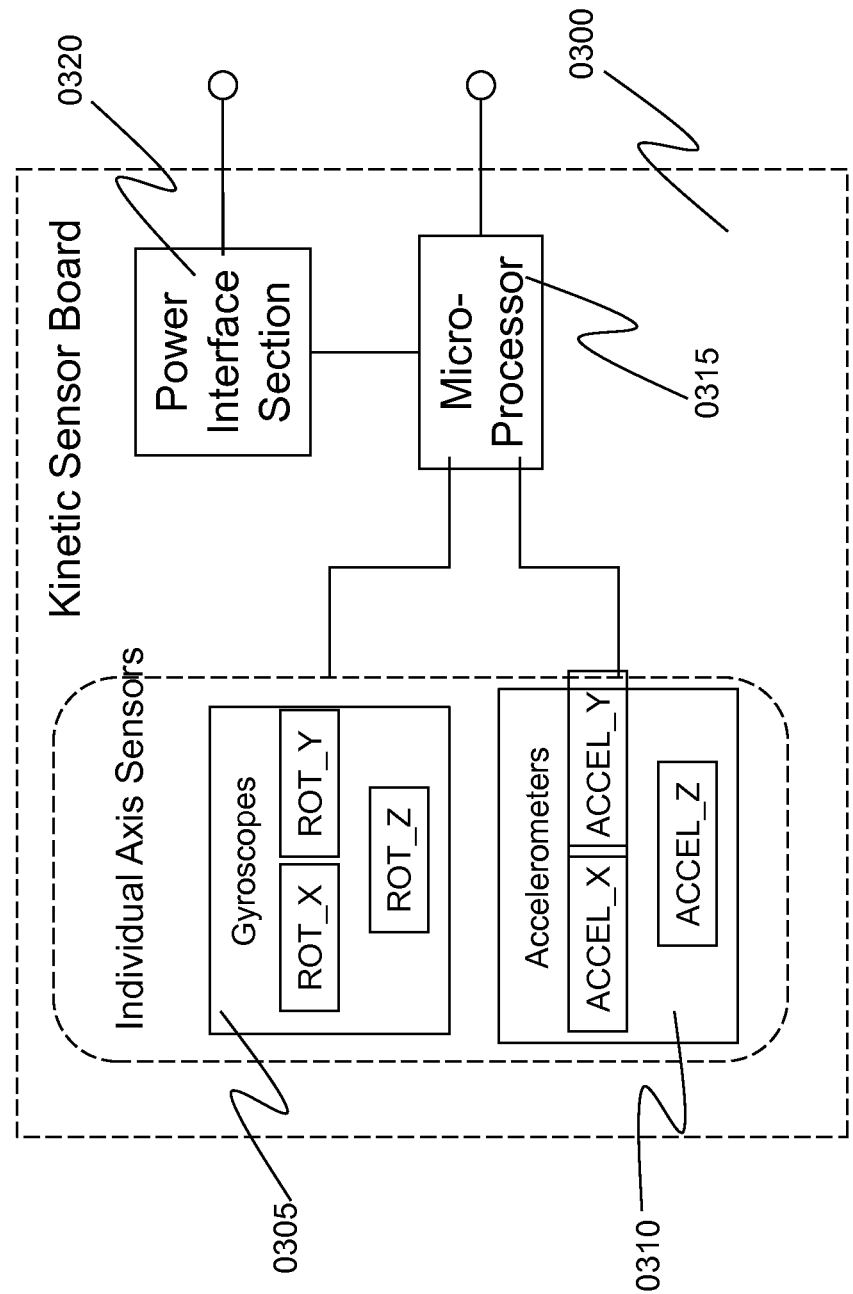
FIGS. 3A-3B Schematic showing various system components of the movement disorder recovery device as applied to a subject: 3A) depicts the subject-worn sensor unit, and 3B) depicts transceiver schematics.
Figure 3B:
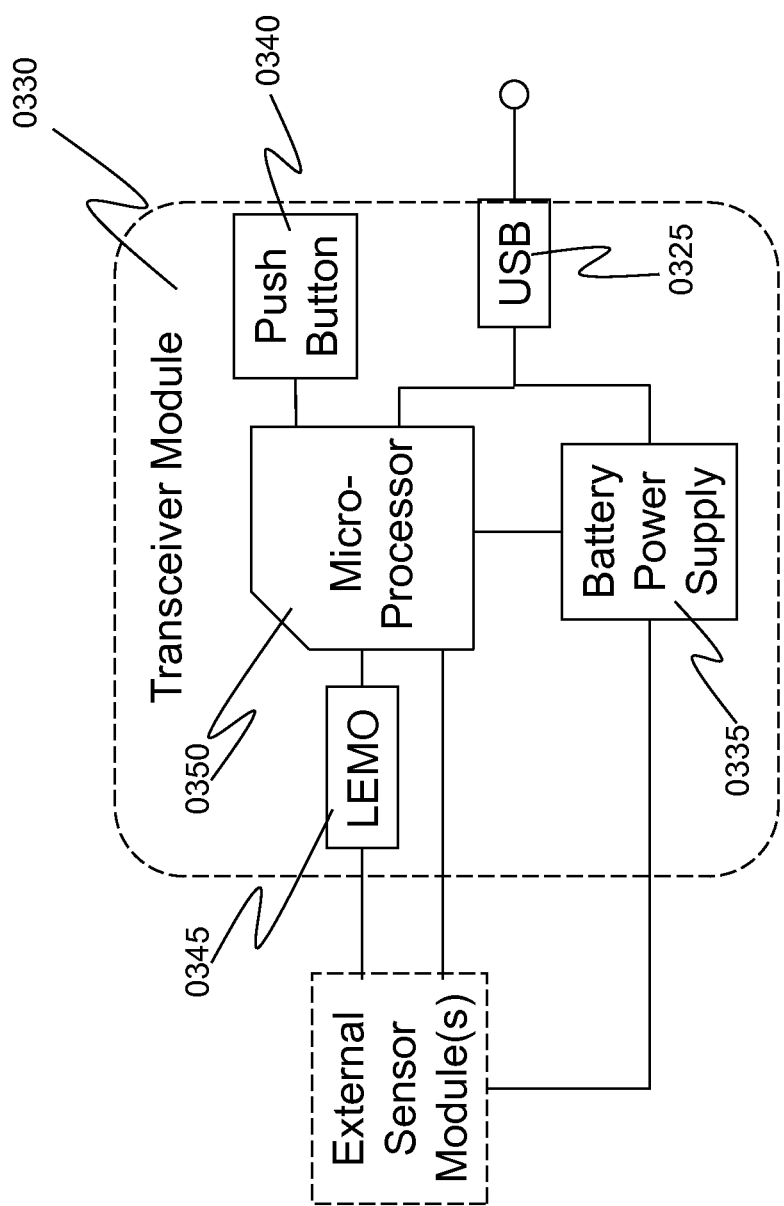

FIGS. 3A and 3B depict block diagrams for embodiments of various components of the portable therapy system or device of the present invention. FIG. 3A is a block diagram for one embodiment of the subject worn sensor unit. FIG. 3A shows a kinetic sensor board 0300 (or subject worn external sensor) of the present invention. The kinetic sensor board 0300 is preferably configured with both an accelerometer and a gyroscope for quantifying the subject's motion. In this particular embodiment, the kinetic sensor board 0300 consists of three gyroscopes 0305 and three orthogonal accelerometers 0310. The kinetic sensor board 0300 also includes a microprocessor 0315 and a power interface section 0320.

FIG. 3B is a block diagram for one embodiment of an optional, separate subject worn transceiver module 0330. The transceiver module includes a blue tooth radio (not shown, but for example, EB100 A7 Engineering) to provide wireless communications with the subject PC, EMG amplifier and data acquisition circuitry (not shown), on board memory (not shown), a microprocessor 0350, and a battery power supply (lithium powered) 0335 that supplies power to both the transceiver module 0330 and one or more external sensor modules (see FIG. 3A, ref 0300) or sensors of the portable therapy system or device. The transceiver module 0330 also includes a USB port 0325 to provide battery recharging and serial communications with the subject PC. The transceiver module also includes a push button input 0340. The transceiver module also includes a LEMO connector 0345 to attached EMG electrode leads to the module.

Figure 4:
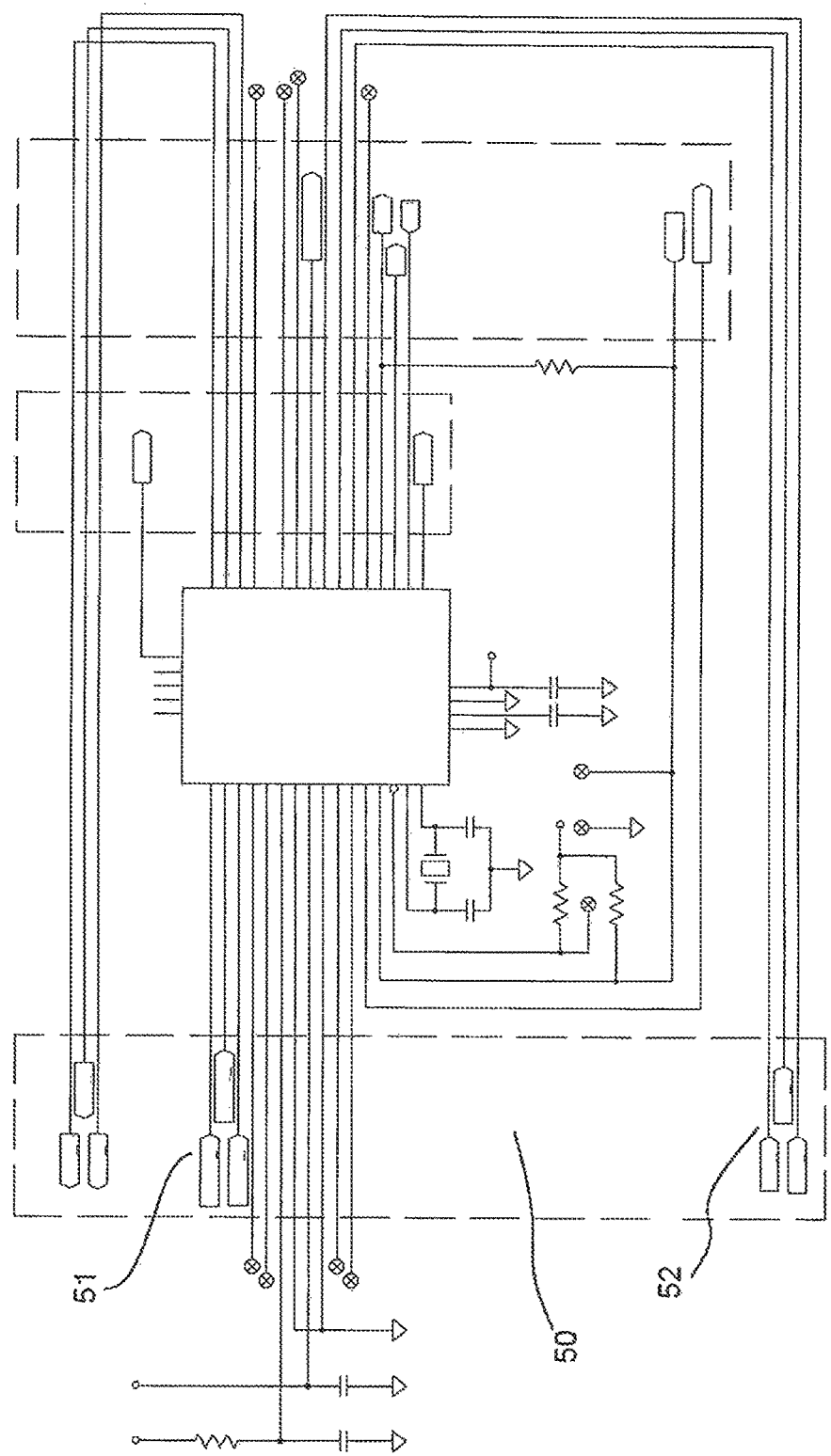
FIGS. 4, 4A-4C. Schematic depicting an alternative embodiment of the subject-worn sensor unit as a whole, and broken down into sections in FIGS. 4A-4C for clarity and detail.
Figure 4A:
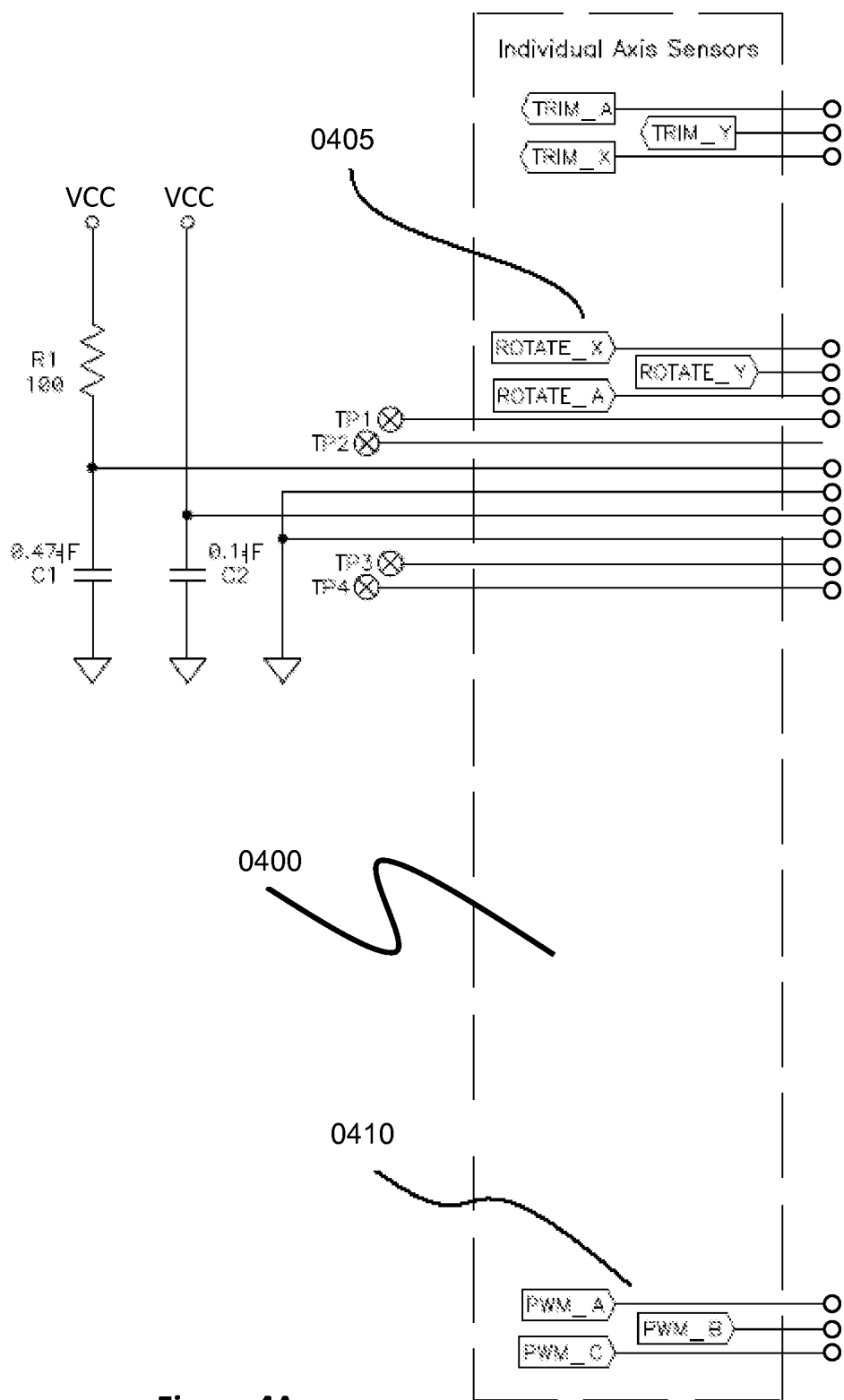
Figure 4B:
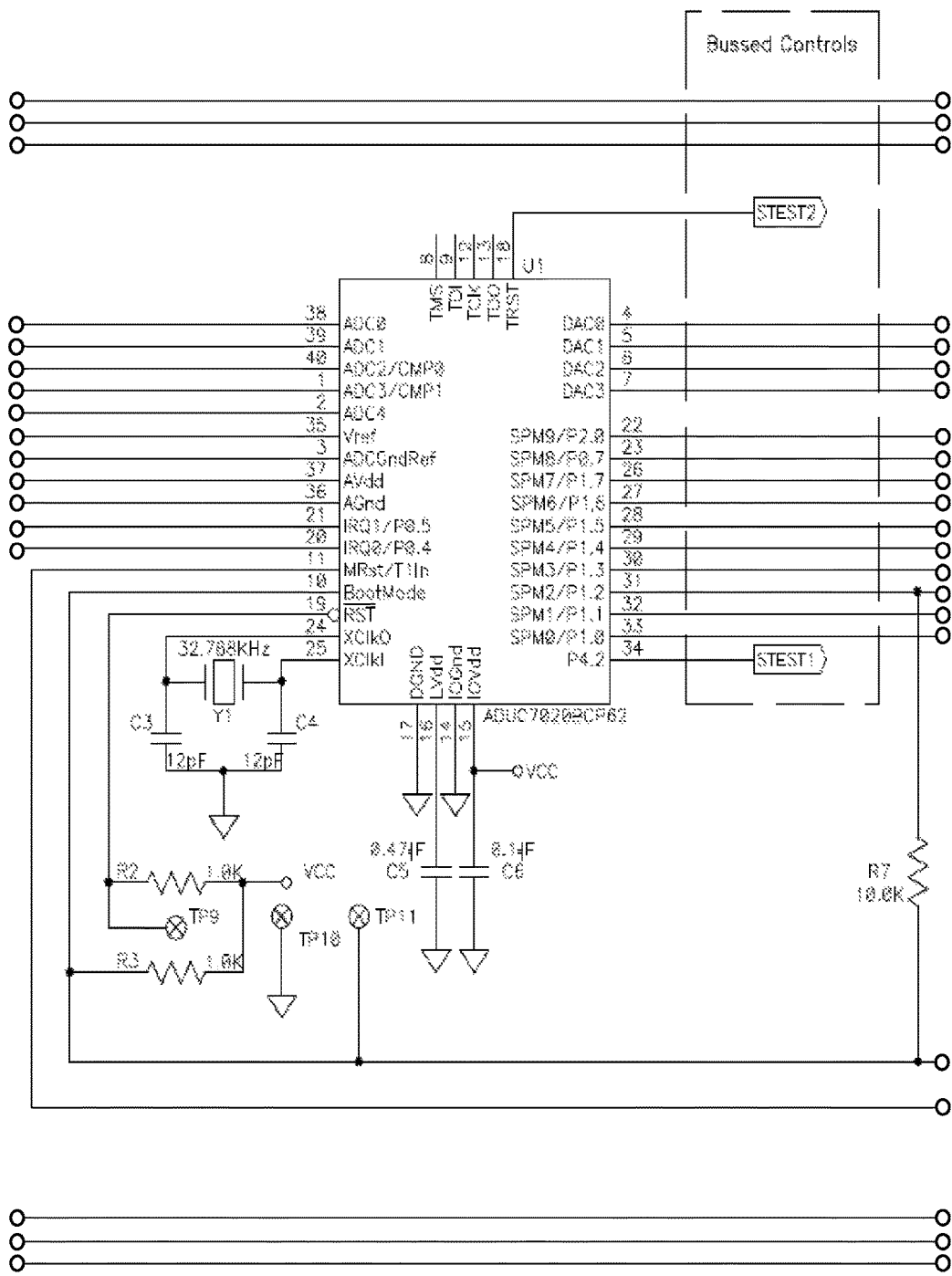
Figure 4C:
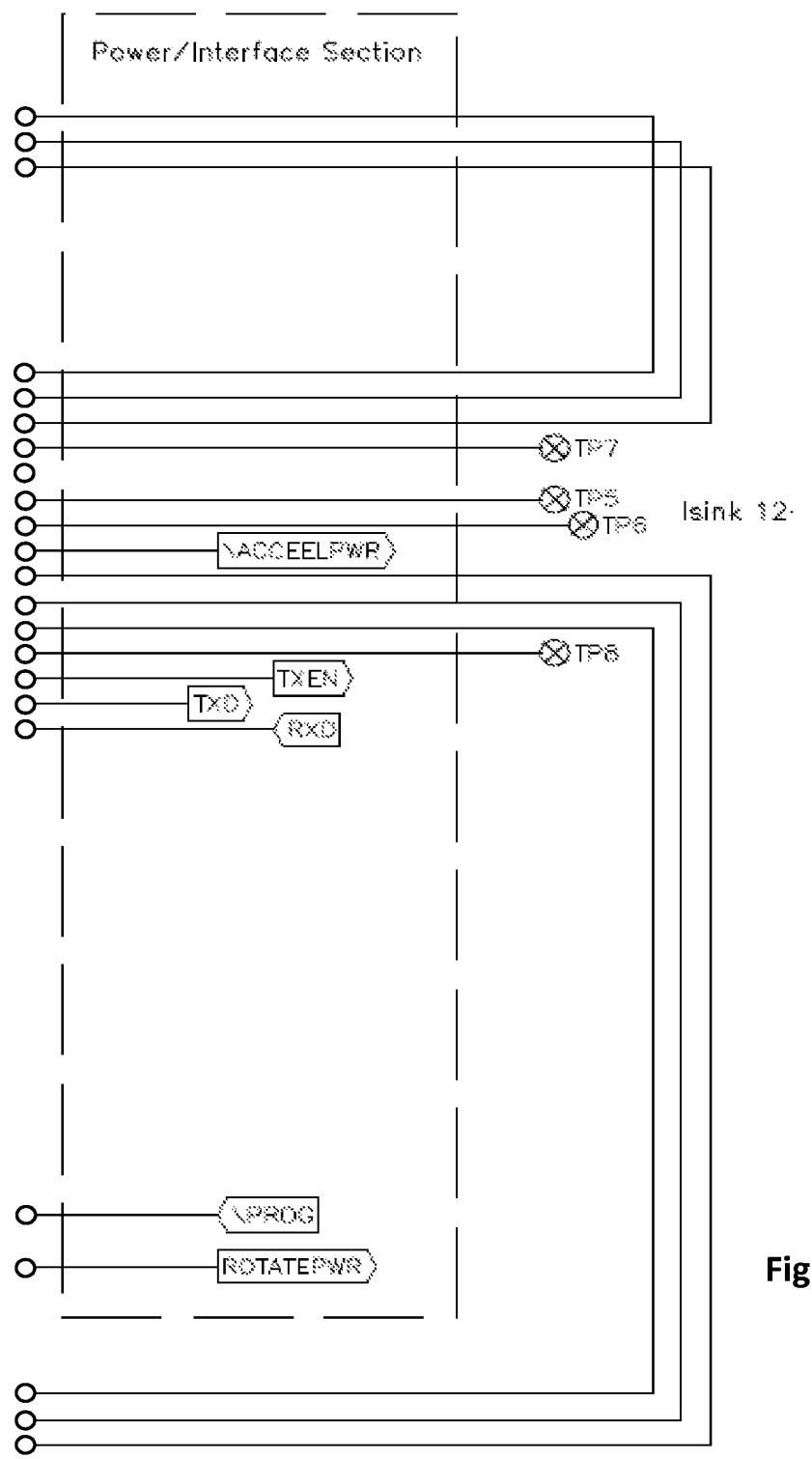

FIG. 4 is an overview electrical schematic diagram for one embodiment of the subject worn sensor unit that is subsequently broken down into constituent parts in FIGS. 4A-4C for better clarity. FIG. 4A shows a kinetic sensor board 0400 (or subject worn external sensor) of the present invention. The kinetic sensor board 0400 is preferably configured with both an accelerometer and a gyroscope for quantifying the subject's motion. In this particular embodiment, the kinetic sensor board 0400 consists of three gyroscopes 0405 and three orthogonal accelerometers 0410. The kinetic sensor board also includes a microprocessor and a power interface section.

Figure 5:
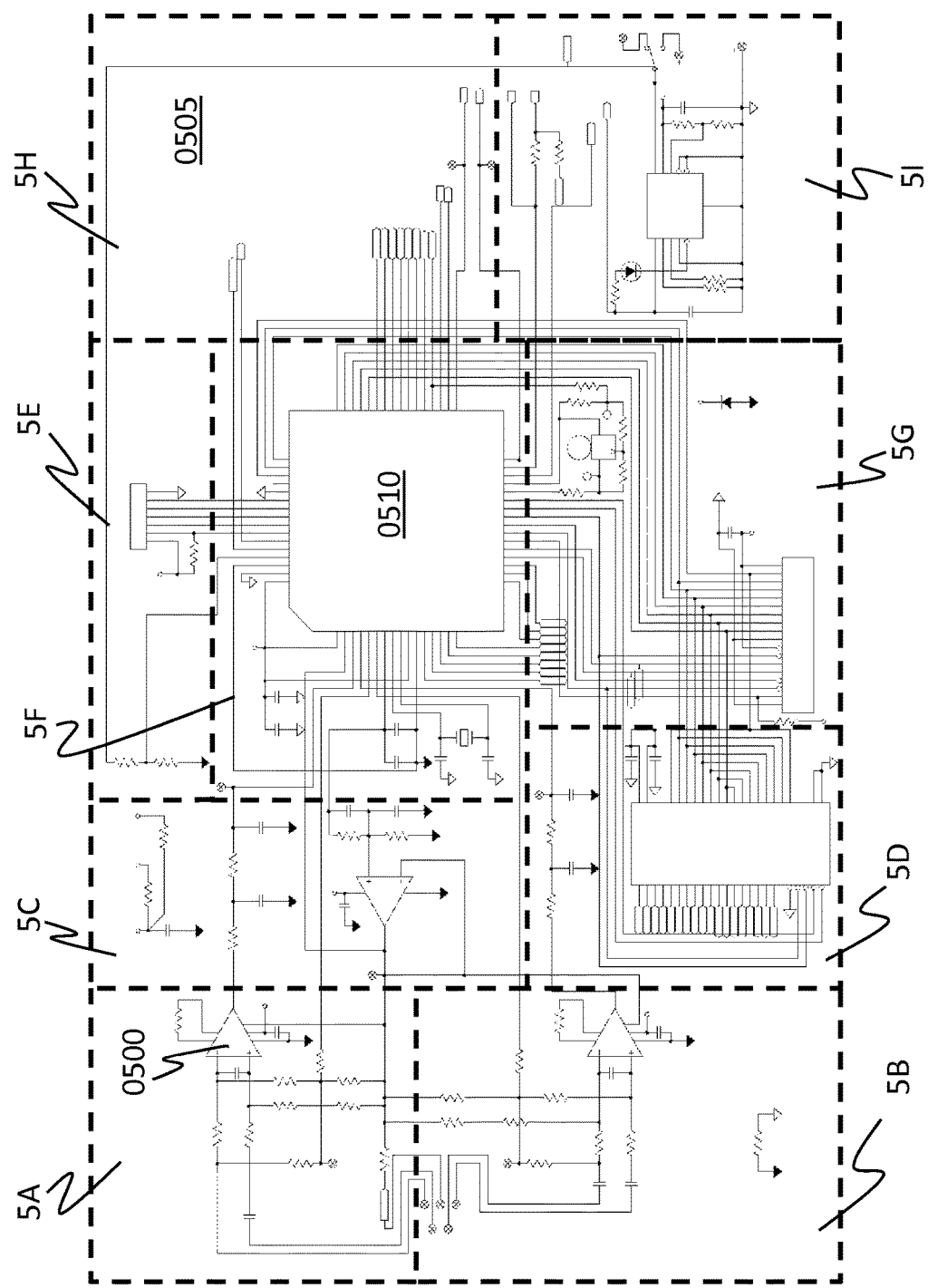
FIGS. 5, 5A-5I. Schematic depicting an alternative embodiment of a transceiver unit or component as a whole, and broken down into sections in FIGS. 5A-5I for clarity and detail.
Figure 5A:
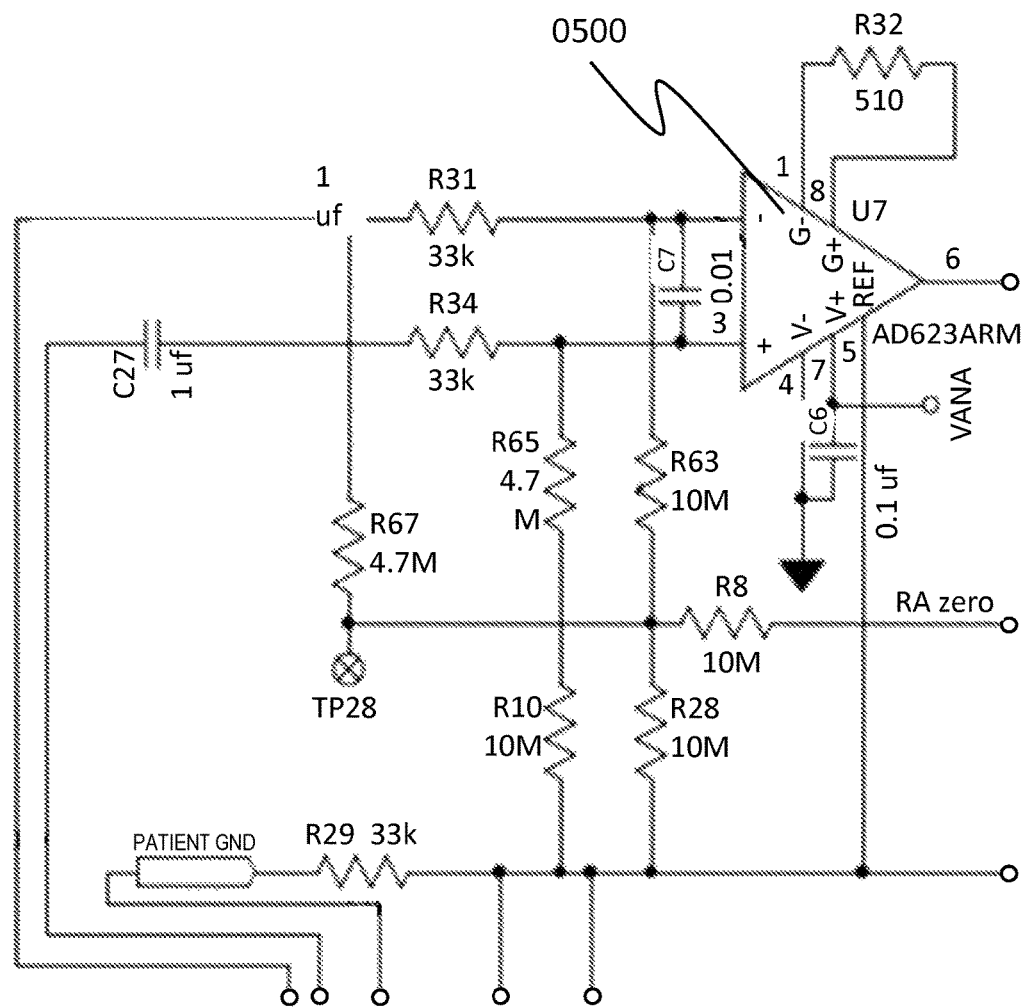
Figure 5B:
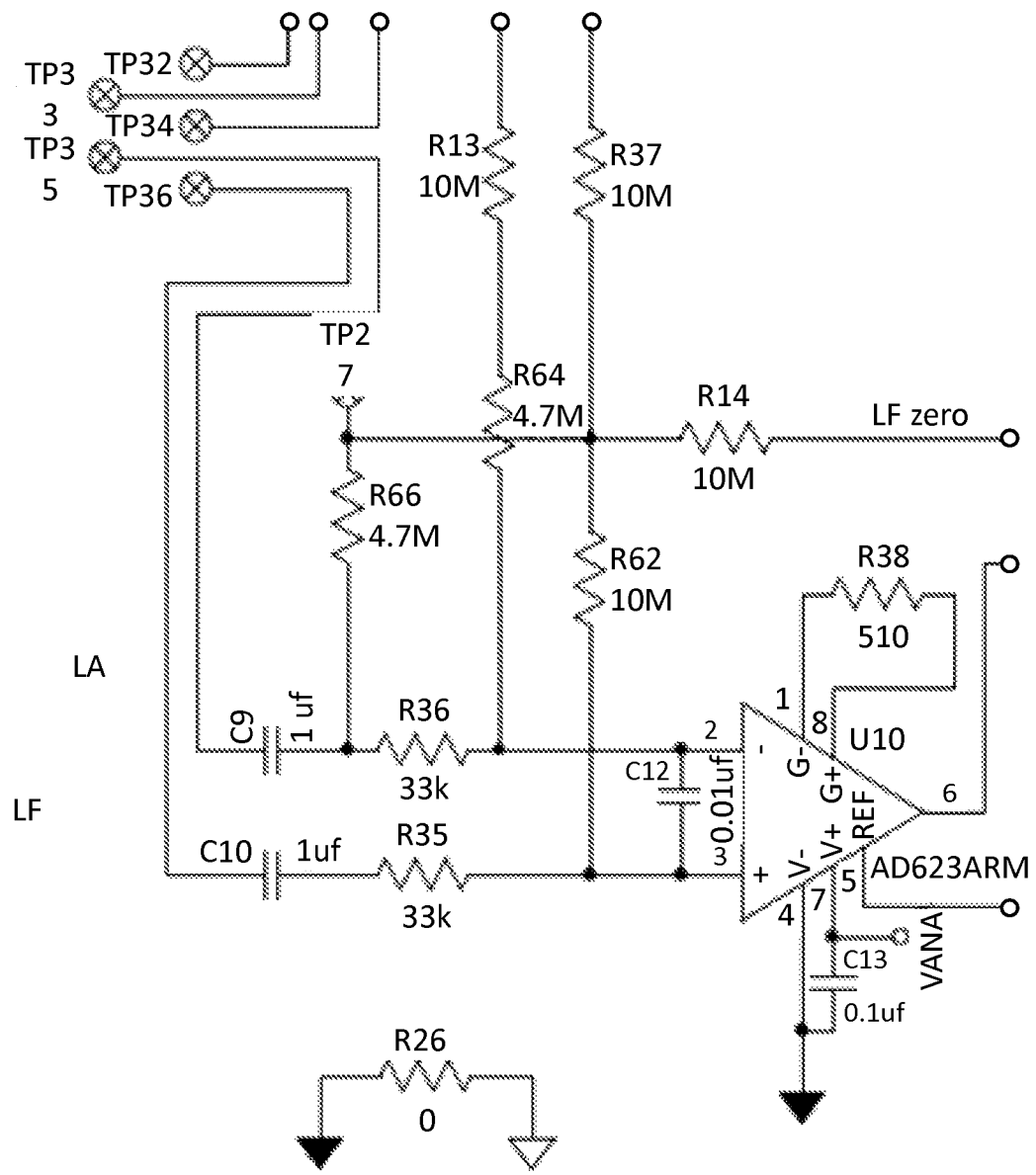
Figure 5C:
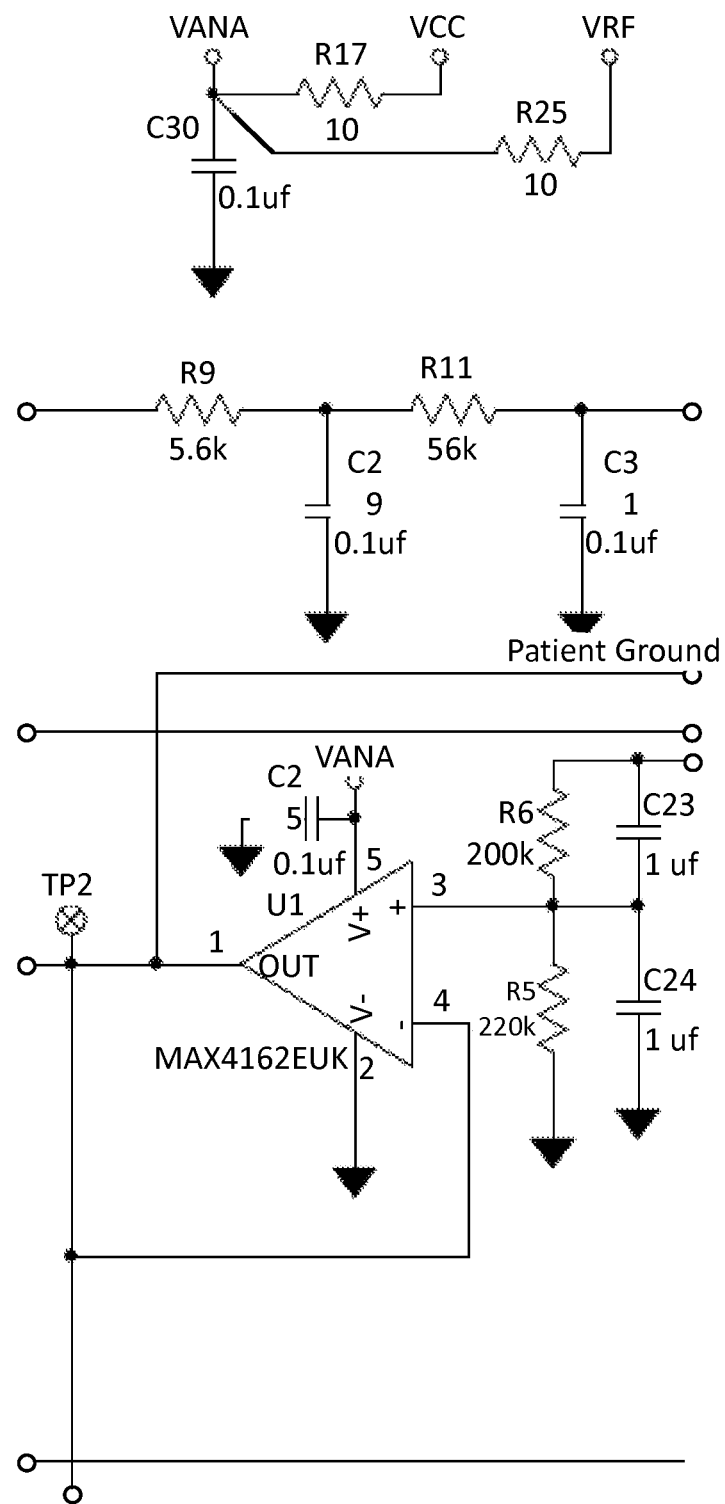
Figure 5D:
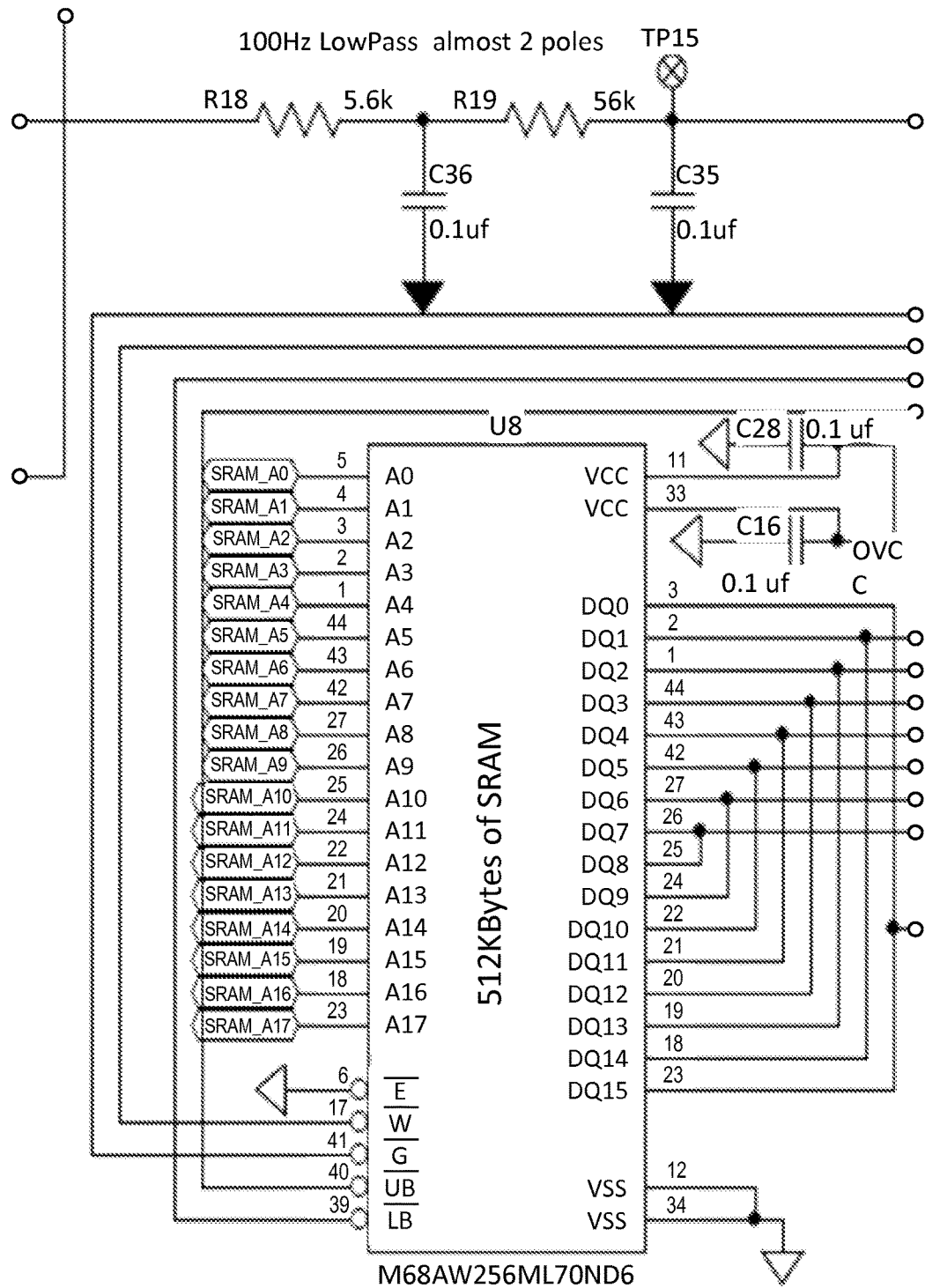
Figure 5E:
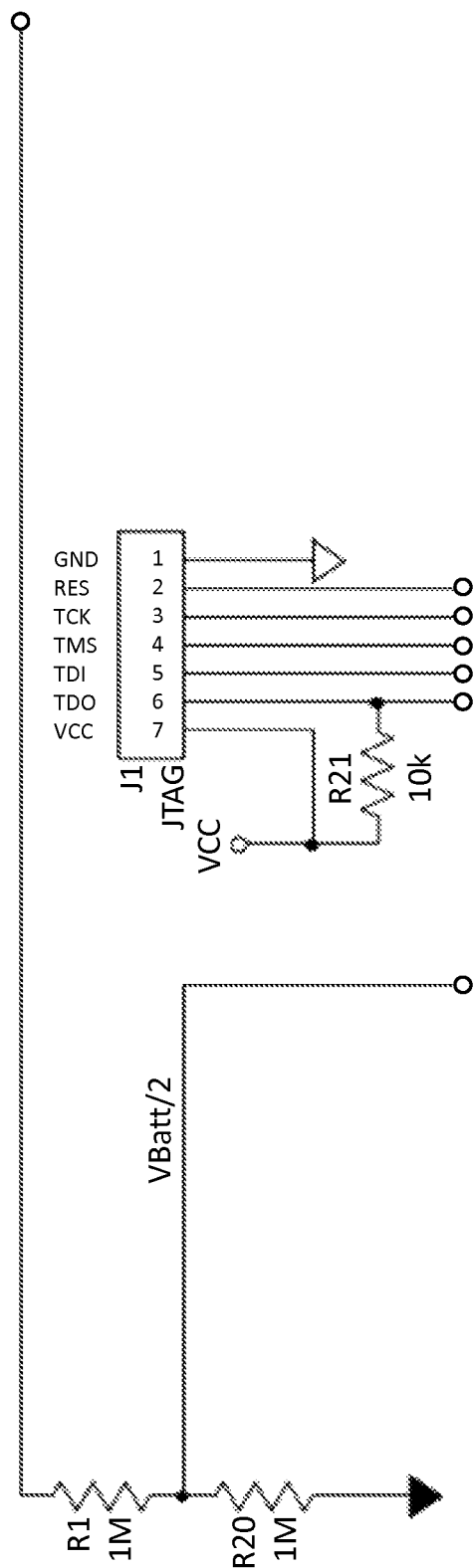
Figure 5F:
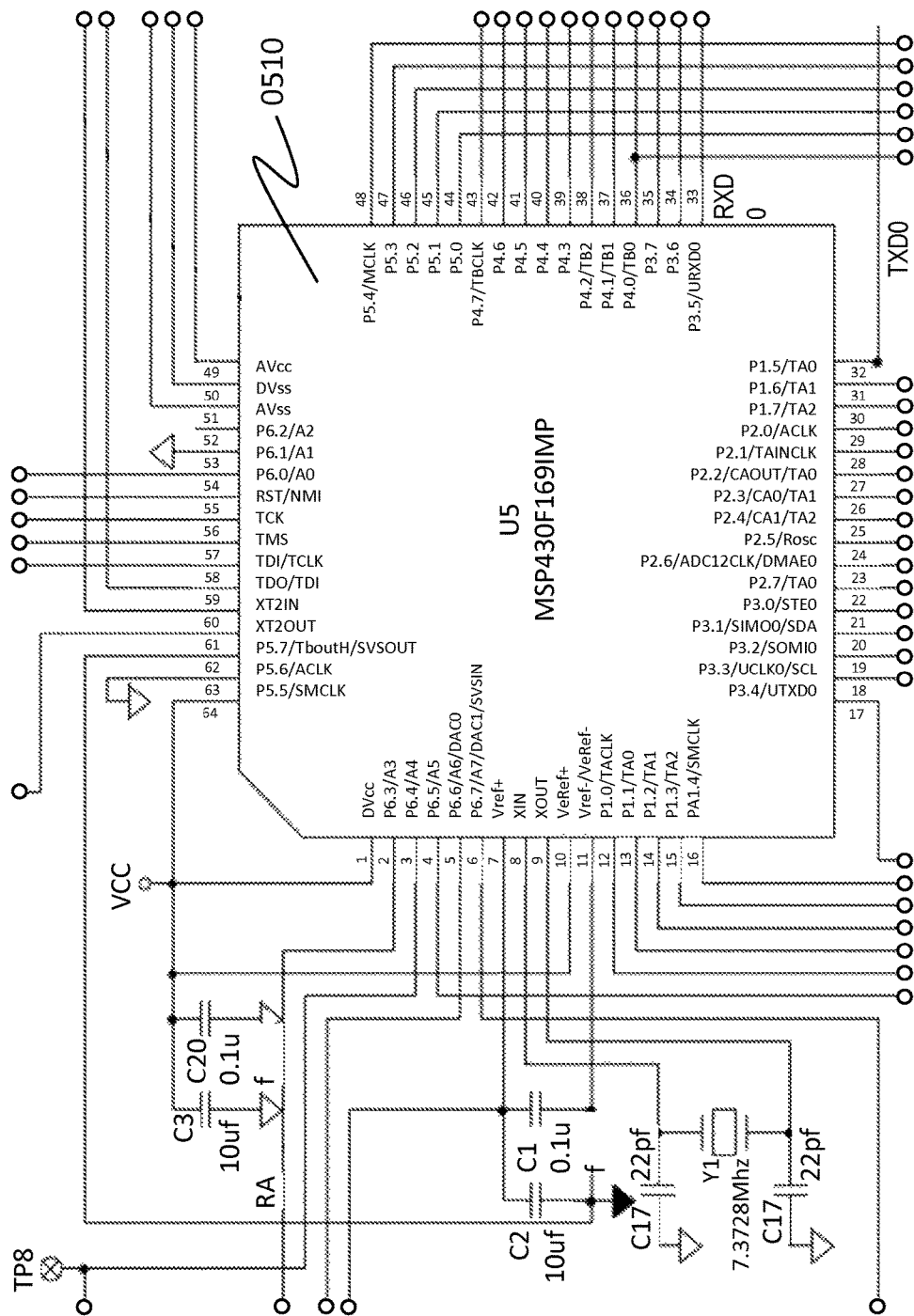
Figure 5G:
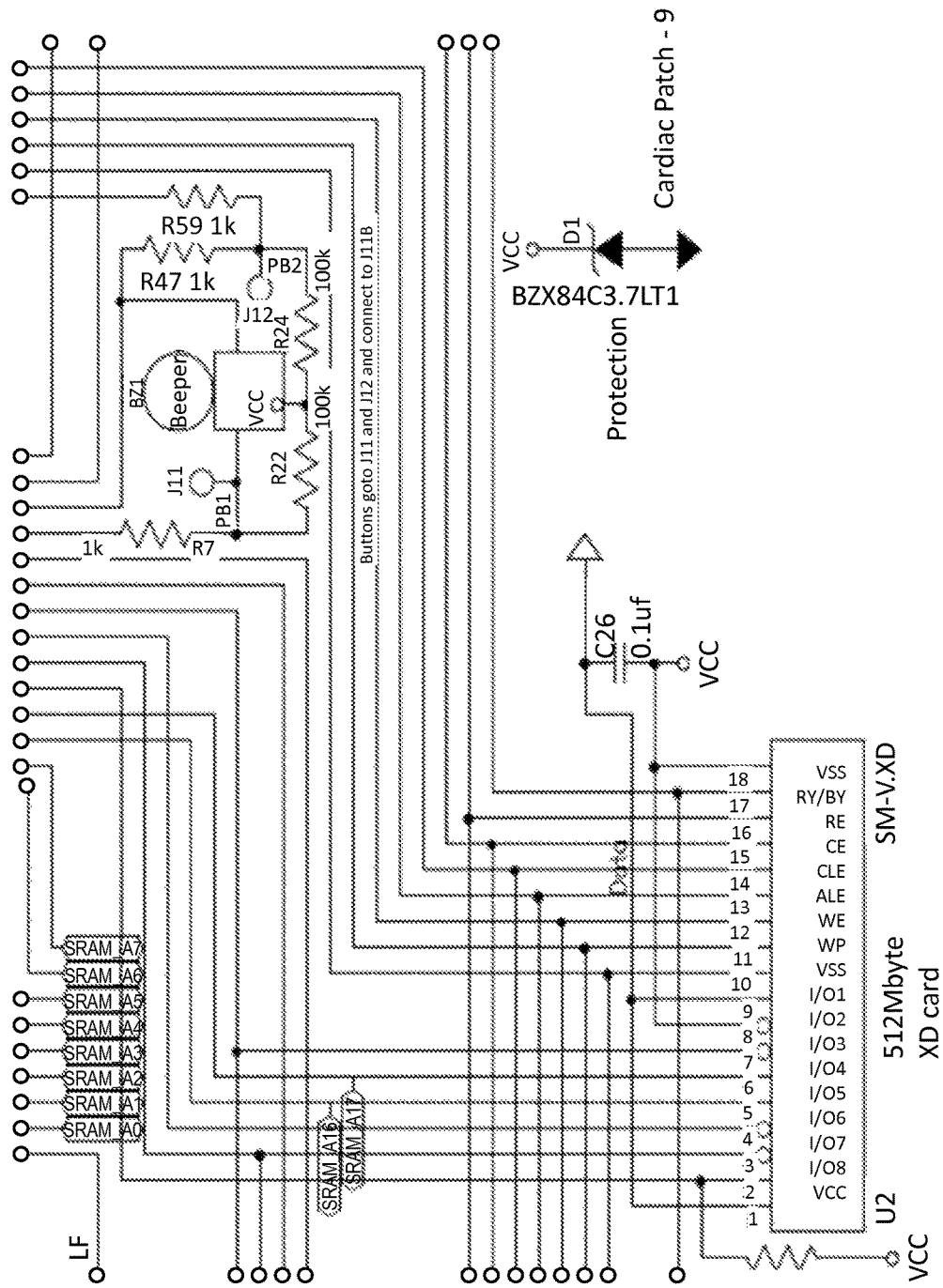
Figure 5H:
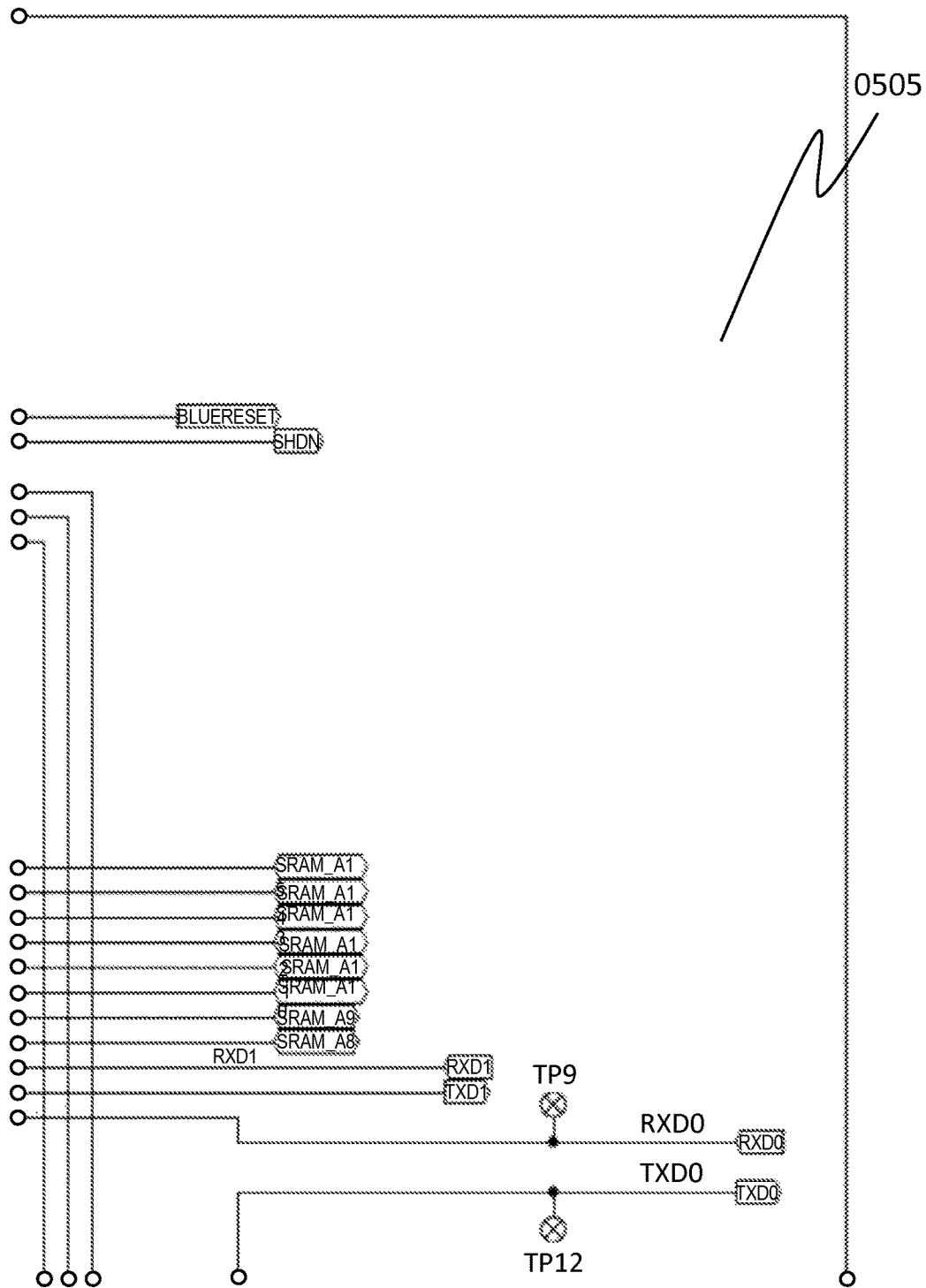
Figure 5I:
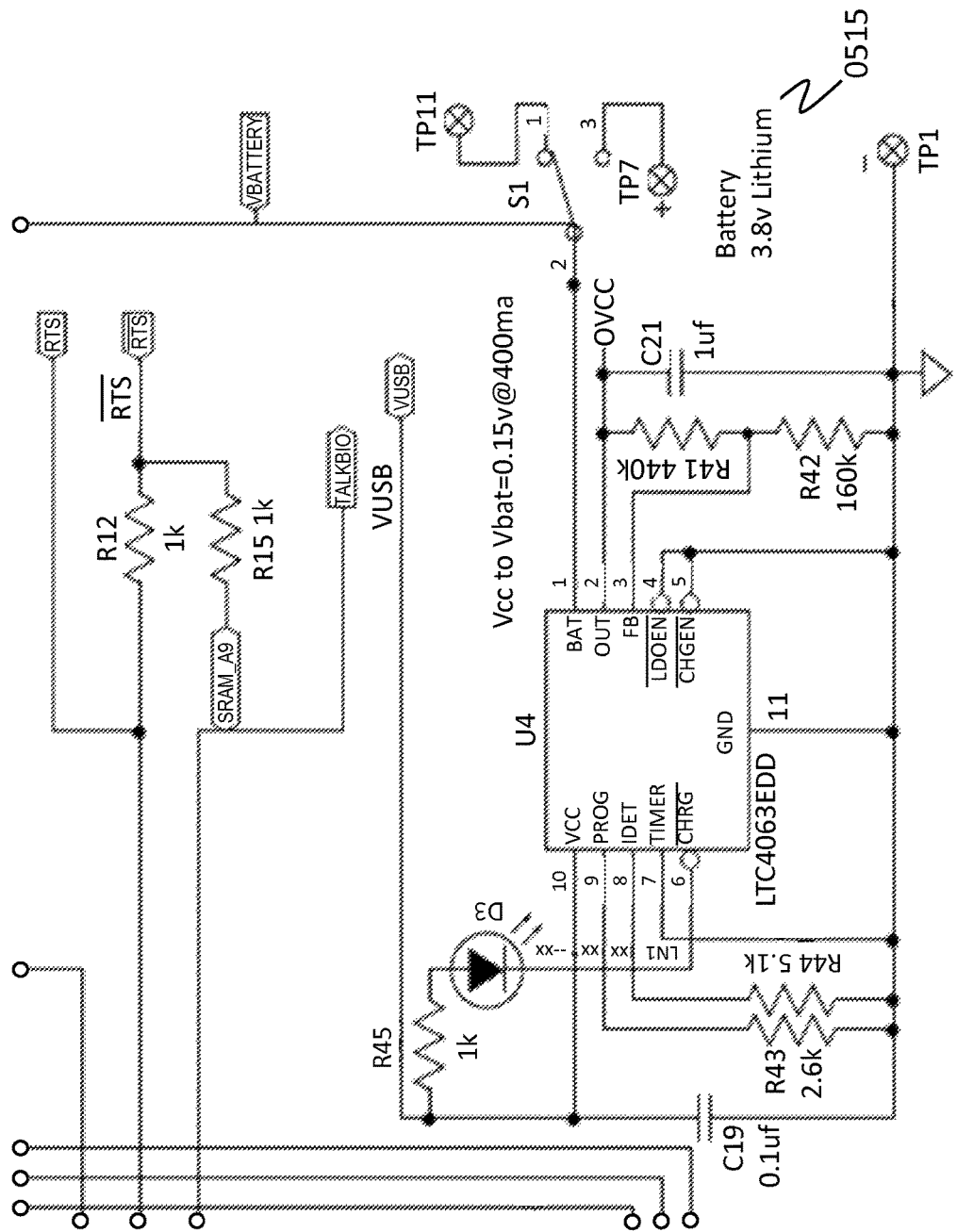

FIG. 5 is an overview electrical schematic diagram for one embodiment of a subject worn transceiver module 0505 that is subsequently broken down into constituent parts in exploded views in FIGS. 5A-5I for better clarity. The transceiver module includes a Bluetooth® radio to provide wireless communications with a subject PC, EMG amplifier and data acquisition circuitry, on board memory, a microprocessor 0510, FIGS. 5 and 5F, and a battery power supply (lithium powered) 0515, FIG. 5I that supplies power to both the transceiver module 0505 and one or more external sensor modules (see FIG. 4, ref. 0400) or sensors of the portable therapy system. The transceiver module also includes a USB port to provide battery recharging and serial communications with the subject PC. The transceiver module also includes a push button input. The transceiver module also includes a limo connector to attached EMG electrode leads to the module.

Figure 6:
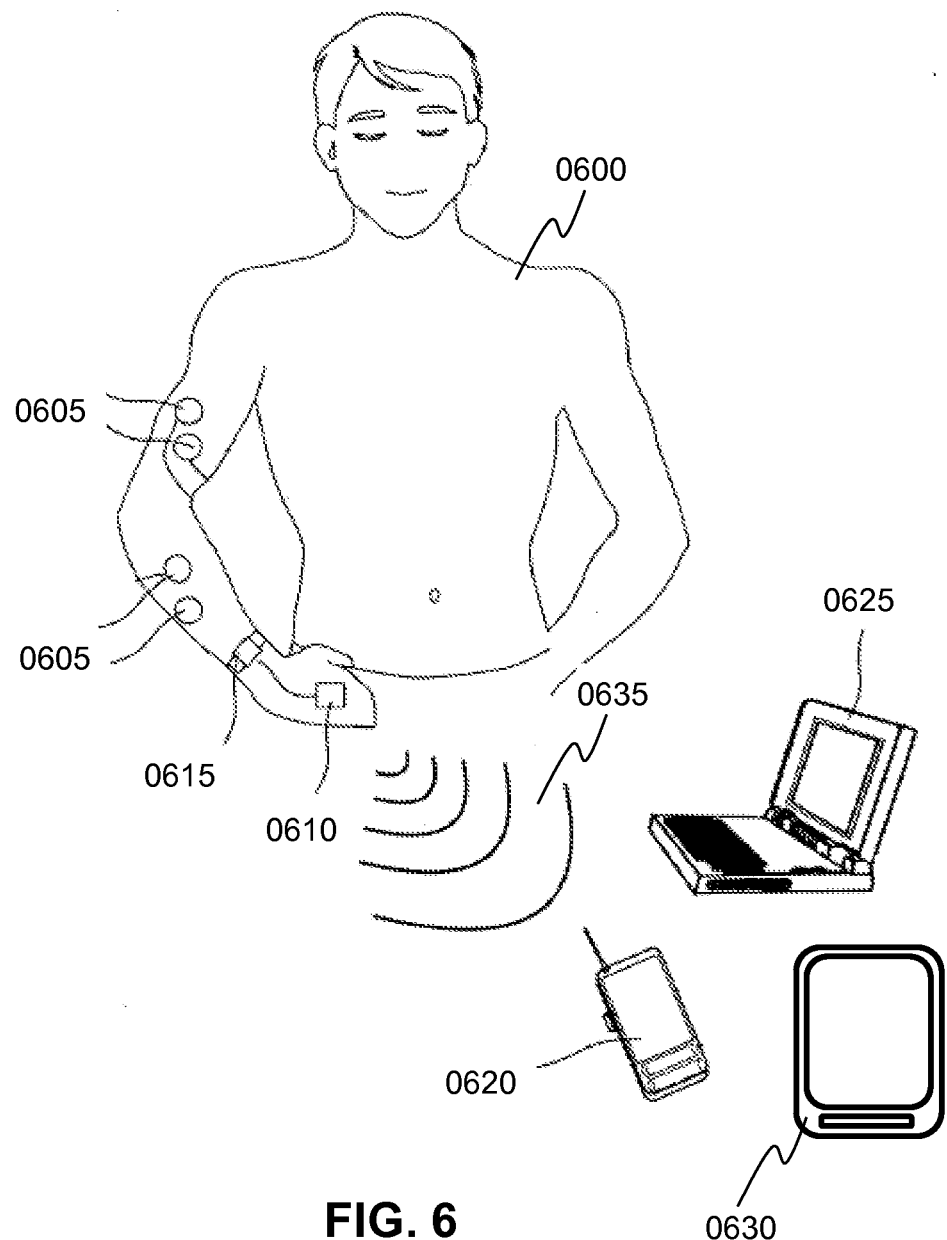
FIG. 6. Schematic showing various system components of the movement disorder device in use with a particular embodiment of the present invention aimed at measuring movement of the subject's arm.

FIG. 6 illustrates one embodiment of the system components of the wireless movement disorder monitor and employed upon a subject 0600. The optional external sensor module 0610 in this embodiment contains three orthogonal accelerometers (not shown) and three orthogonal gyroscopes (not shown). This input to the optional external sensor module 0610 consists of the kinetic forces applied by the user and measured by the accelerometers and gyroscopes. The output from the board is linear acceleration and angular velocity data in the form of output voltages. These output voltages are input to an optional separate transceiver module 0615. These voltages undergo signal conditioning and filtering before sampling by an analog to digital converter. This digital data is then stored in on board memory and/or transmitted as a packet in RF transmission by a blue tooth transceiver. Additionally, EMG electrodes or other sensors 0605 worn by the subject may be input to the optional separate transceiver module 0615. An amplifier on the optional separate transceiver module 0615 amplifies the EMG signal(s) before signal conditioning, filtering, and sampling by the analog to digital converter. The EMG data is also stored in the on board memory and/or contained in the packet for RF transmission. A microprocessor (not shown) in the optional separate transceiver module 0615 controls the entire process. Kinetic and EMG data packets may be transmitted 0635 to a nearby portable therapy system or device 0620, 0625, 0630 of some variety which receives the data using an embedded blue tooth radio. Alternatively and preferably, the optional separate transceiver module 0615 may be excluded, and the sensors may transmit their measured kinematic data directly to the portable therapy system or device 0620, 0625, 0630 which performs all steps and storage described above. Kinetic and EMG data may also be stored on the on board memory and downloaded to a computer or database (not shown) at a later time. The portable therapy system or device 0620, 0625, 0630 then processes, analyzes, and stores the data. The kinetic sensor board 0610 measures accelerations along and angular velocities about each of three orthogonal axes. The signals from the accelerometers and gyroscopes of the kinetic sensor board 0610 are preferably input into a processor for signal conditioning and filtering. Preferably, three Analog Devices gyroscopes were utilized on the kinetic sensor board with an input range up to 1200 degrees/second. Additionally, a MEMS technology dual axis accelerometer, from Analog Devices, may be employed to record accelerations along the x and y-axes. The sensors provide preferably at least 80 dB dynamic range, low noise (1 mg/sqrt (Hz)), and low power (<2 mA per axis) in a surface mount package. Other combinations of accelerometers and gyroscopes known to those skilled in the art could also be used. A lightweight plastic housing was then used to house the sensor for measuring the subject's external body motion. The external body motion sensor(s) can be worn on the subject's finger, hand, wrist, fore arm, upper arm, head, chest, back, legs, feet and/or toes.

Figure 7:
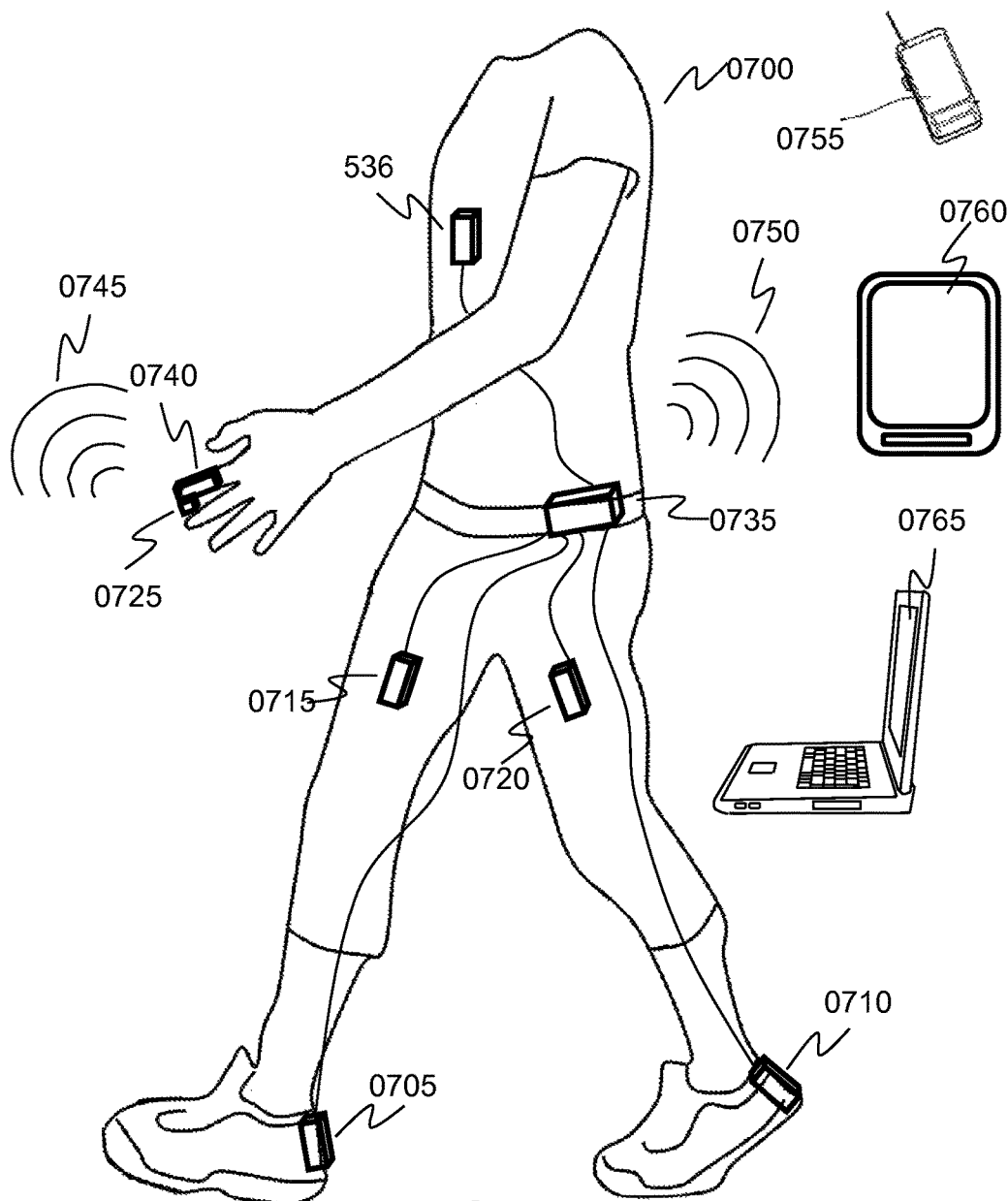
FIG. 7. Graphic depiction of a subject showing possible movement disorder device unit placement options on multiple, separate parts of the subject's body either individually or simultaneously in multiple, separate locations.

FIG. 7 illustrates possible sensor or sensor unit locations of a movement measuring or portable therapy system or device or system for different embodiments of the present invention measuring or monitoring full body motion, or body motion from multiple, discrete body parts. The subject 0700 in this particular embodiment is wearing six sensor units 0705, 0710, 0715, 0720, 0725, 0730 comprising accelerometers and gyroscopes (both not shown, but described in more detail herein) for recording movement data. The subject 0700, in this embodiment, is depicted to be wearing at least one sensor unit on each foot 0705, 0710, thigh 0715, 0720, on one finger 0725, and on the torso or trunk 0730, though more sensors or sensor units may be placed in each, and/or other locations. Additionally, an optional, separate transceiver unit 0735 for preprocessing and transmitting the movement data may be in wired (see connection to sensors/units on subject's heels, thighs and torso) or wireless communication 0745 with the wireless transmission components 0740 of the wireless finger sensor 0725. The optional, separate transceiver unit 0735 may further be in wired (not shown) or wireless 0750 communication with the portable therapy system or device which may be a smartphone 0755, tablet computer 0760, laptop or other computer 0765, or any other such device capable to be used as the portable therapy system or device. The movement data from the optional, separate transceiver unit 0735 is either stored for transfer at a later time or for immediate transmission to receiving circuitry or electronic components (not shown) on the portable therapy system or device via various mediums and any transmission protocols, for example, radio link, or by Bluetooth, WIFI, or even USB, or the like. The processor (not shown) of the portable therapy system or device 0755, 0760, or 0765 feeds the data into a trained algorithm preferably loaded into the processor. The trained algorithm then uses the measured movement data to determine, detect or predict some movement impairment, unsafe or undesirable movement, unsafe or undesirable condition, or symptom of a movement disorder and outputs a signal corresponding to a cue or stimulus, and optionally to a treatment or therapy command and/or subject customized treatment which may then be displayed on the portable therapy system or device or some other display device, or as input to control a treatment device such as an electric stimulator, automated medicine delivery or titration device, or the like.

Figure 8A:
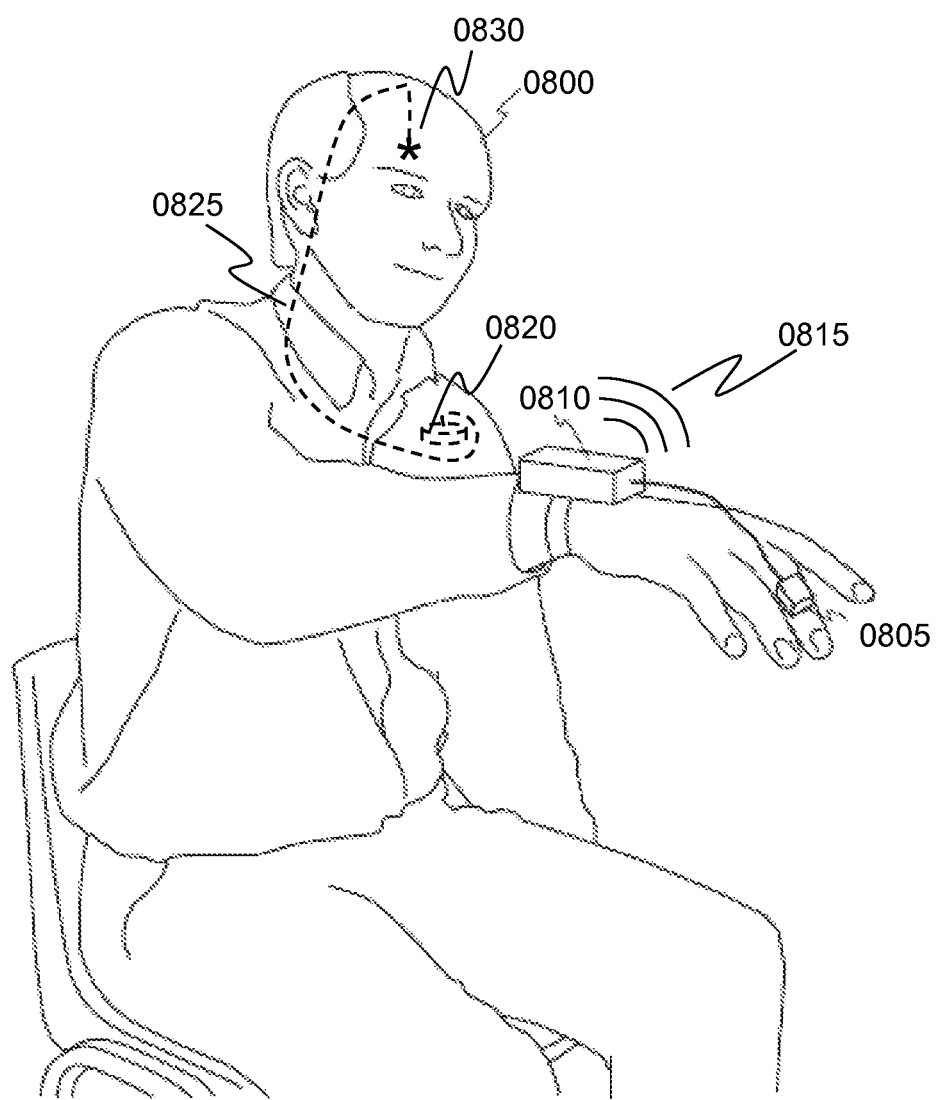
FIGS. 8A-8B. Depiction of two optional treatment or therapy assistance mechanisms optionally used with the present invention: 8A) a deep brain stimulation (DBS) system; and 8B) a drug or medication delivery system with either an implanted or external pump device.

FIG. 8 depicts various embodiments of treatment or therapy devices that may be included in some embodiments of the present invention to provide assistive treatment or therapy on an automated or semi-automated basis, above and beyond cueing. FIG. 8A is a schematic showing a closed-loop deep brain stimulation (DBS) system. A movement measuring device, such as the portable therapy system or device of the present invention, worn by a subject 0800, and comprising a sensor module 0805 and an optional, separate transceiver unit 0810 continually measures the subject's movement data during while at home during activities of daily living and optional clinically directed tasks. The optional, separate transceiver unit 0810, or transceiver circuitry of the portable therapy system or device, is capable of optionally correlating with a central database (not shown) or database system through wired (not shown) or wireless 0815 communication, such as the internet, Bluetooth, or the like, to help determine a therapy or treatment protocol to be provided to the subject. This protocol is then communicated to an implantable pulse generator 0820 either from the portable therapy system or device or from a remote programming unit (not shown) preferably controlled by a clinician. When activated according to the protocol, the implantable pulse generator 0820 sends an electronic pulse through an implanted wire and electrode lead 0825 to generate a stimulus 0830 in the subject's brain.

Figure 8B:
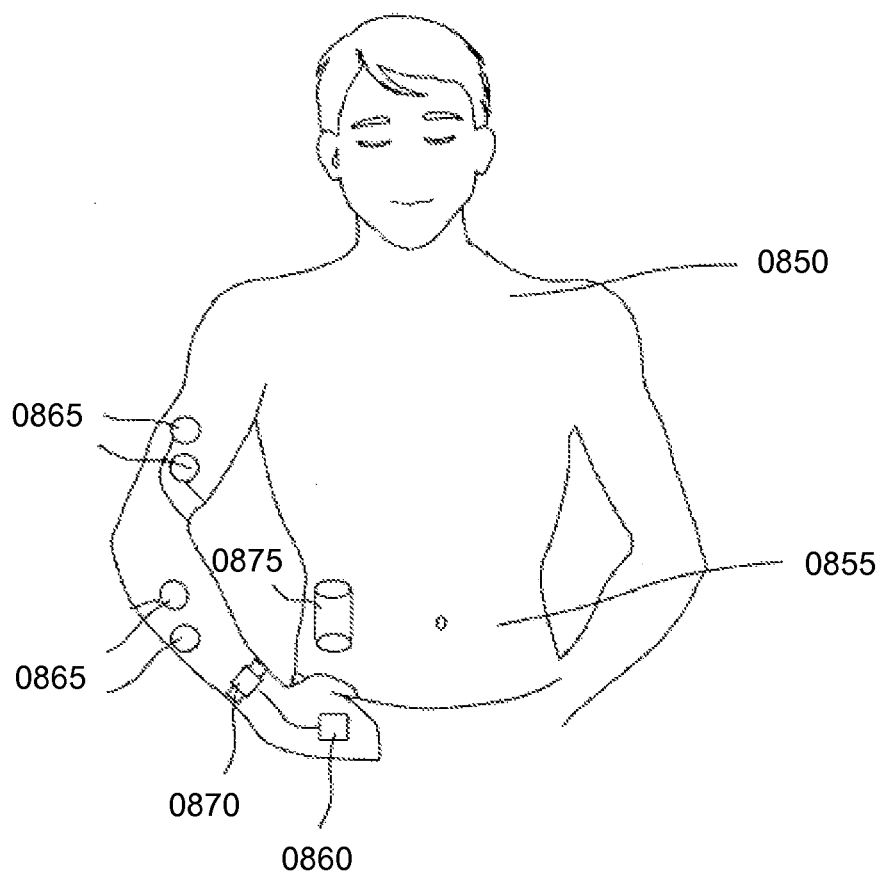

FIG. 8B is a schematic diagram showing placement of various components of closed loop or semi-closed loop drug delivery system with drug or medication reservoir that can be used as a treatment or therapy device beyond the cueing function of the present invention. The system includes all of the components for measuring the subject's body movement, including, but not limited to, an external sensor module 0860 or sensors integrated or otherwise attached to the portable therapy system or device, an optional, separate transceiver module 0870, optional EMG electrodes 0865, and adds the drug delivery system, which includes a reservoir 0875 for holding medication or a drug with an embedded transceiver (not shown) and processor (not shown) and actuator (not shown) for allowing delivery, and a controller (not shown) for activating and deactivating the actuator based in part on the signal from the at least one of the sensor modules 0860. In the depicted embodiment, a reservoir 0875 is shown as implanted into the abdomen 0855 of the subject. Alternatively, the reservoir 0875 may be external and can be worn or attached to the subject by any device or methods known to those of skill in the art. The reservoir 0875 contains a drug or medication, which is released into the subject's body through activation of an actuator (not shown). The respective optional, separate transceiver module 0870 or transceiver circuitry of the portable therapy system or device (not shown) is preferably connected to the EMG electrodes 0865 and optional external sensor modules 0860 via wired or wireless communication as described herein. The transceiver module 0870 or transceiver circuitry of the portable therapy system or device (not shown) is further preferably connected either wirelessly or wires to a controller (not shown), which activates and deactivates an actuator (not shown) to release medication from the implantable reservoir 0875 into the subject's body. Such embodiments can be fully closed-loop wherein control of the drug or medication delivery is controlled solely by the portable therapy system or device and the measured movement data and predicted or detected impairments, or can be semi-closed loop such that intervention, preferably by a clinician who may be located remotely, is either required or allowed in order to trigger the drug or medication delivery based on the output of the system and algorithm.

Figure 9:
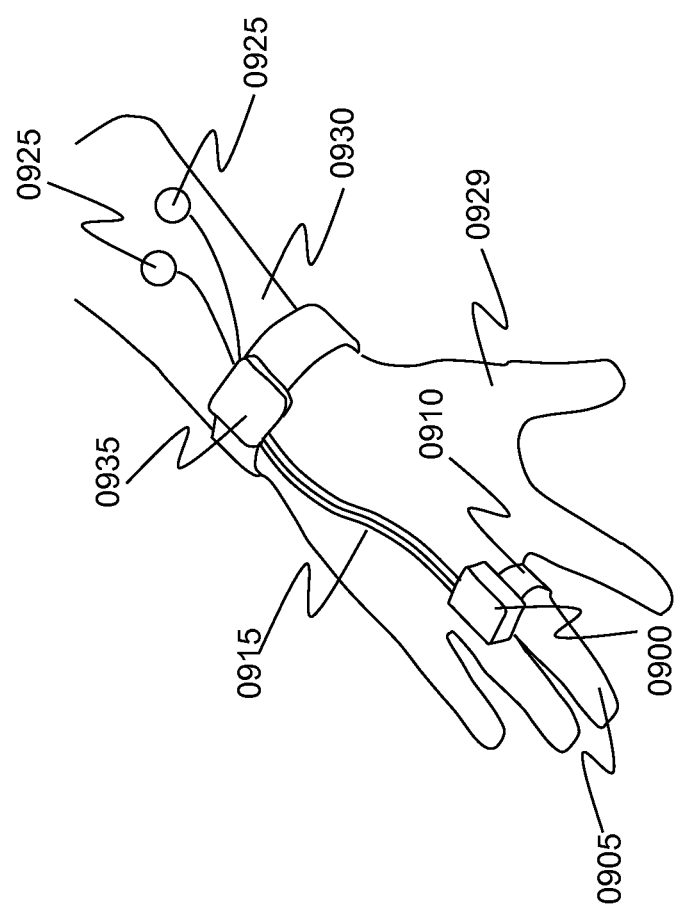
FIG. 9. Schematic showing placement of various components of the movement disorder device with an external sensor module for the hand and electrodes.

FIG. 9 illustrates one possible, hand-specific movement measurement embodiment of the subject 0920 worn components of the system combining the sensor board or unit 0900 and the optional, separate transceiver module 0935. The sensor board 0900 is worn on the subject's 0920 finger 0905 and the separate transceiver module 0935 is worn on the subject's 0920 wrist 0930. The separate transceiver module 0935 and one or more external sensor modules 0900 or sensors of the portable therapy system or device are connected by a thin multi-wire lead 0915. The transceiver module 0935 in this embodiment connects to one or more electrodes 0925 used to measure EMG.

FIG. 10A is a block diagram showing one embodiment of the movement impairment or disorder therapy, training and recovery system of the present invention. The portable therapy rehabilitation system or portable therapy system or device 1000 of the present invention can be viewed as comprising three modules or components: a sensor module 1002, a command module 1004 and a computer or processor module 1006. The sensor module 1002 comprises the sensors in their various configurations and groupings. In the depicted embodiment, the sensor module 1002 preferably comprises at least one gyroscope 1008 or other form of motion sensor, an EMG electrode(s) 1010, and adds an additional therapy or treatment delivery component in the form of a stimulating or functional neuromuscular stimulating device 1012. The command module 1004, with which the sensor module 1002 is in communication 1014 enables the signals from the sensors 1008, 1010 showing the subject's movement to be processed and transmitted to a processor module 1006. The command module 1004 can also be used to either relay or calculate when to apply treatment or therapy, such as functional neuromuscular stimulation, through the stimulating electrode 1012. The command module 1004 preferably comprises a system control and power supply 1016 for those devices worn by the subject, functional neuromuscular hardware 1018 for controlling any administered treatment or therapy, EMG amplifiers 1020, data acquisition electronics 1022 and optionally a radio transceiver 1024. Preferably, the command module 1004 communicates with a computer or processor module 1006 which may be integrated into the same enclosure or portable therapy system or device body and use internal hardwired or direct communication 1025, or may be a separate component thus requiring two way, preferably wireless radio communication 1026 or a tethered, two way serial communication 1025 port on each of the modules 1002, 1004. The processor module 1006, whether integrated into and part of the portable therapy system or device 1000 or a separate computer or processor device, preferably comprises processing software 1028, a video display 1030, auditory stimulus 1032 and a radio transceiver 1034 or serial port (not shown).

FIG. 10B is a block diagram showing another embodiment of the movement impairment or disorder therapy, training and recovery system of the present invention. The portable therapy rehabilitation system or portable therapy system or device 1050 of the present invention can be viewed as comprising three modules or components: a sensor module 1051, a command module 1052 and a computer or processor module 1054 146. The sensor module 1051 comprises the sensors in their various configurations and groupings. In the depicted embodiment, the sensor module 1051 preferably comprises at least one gyroscope 1056, at least one accelerometer 1058, or other form of motion sensor, and an automated treatment device 1060, such as an electrical stimulation device, automatic drug or medication titrator, or automatic drug delivery system. The command module 1052, with which the sensor module 1051 is in communication 1062 enables the signals from the sensors 1056, 1058 showing the subject's movement to be processed and transmitted to a processor module 1054. The command module 1052 can also be used to either relay or determine when and how to program the automated treatment device 1060. The command module 1052 preferably comprises a system control and power supply 1064 for those devices worn by the subject, the automated treatment device hardware 1066, data acquisition electronics 1068 and optionally a radio transceiver 1070. Preferably, the command module 1052 communicates with a computer or processor module 1054 which may be integrated into the same enclosure or portable therapy system or device body and use internal hardwired or direct communication 1071, or may be a separate component thus requiring two way, preferably wireless radio communication 1072 or a tethered, two way serial communication 1071 port on each of the modules 1051, 1052. The processor module 1054, whether integrated into and part of the portable therapy system or device 1050 or a separate computer or processor device, preferably comprises processing software and algorithms 1074, optionally a central database 1076 or communication with a central database, and a radio transceiver 1078 or communication port (not shown).

Figure 11:
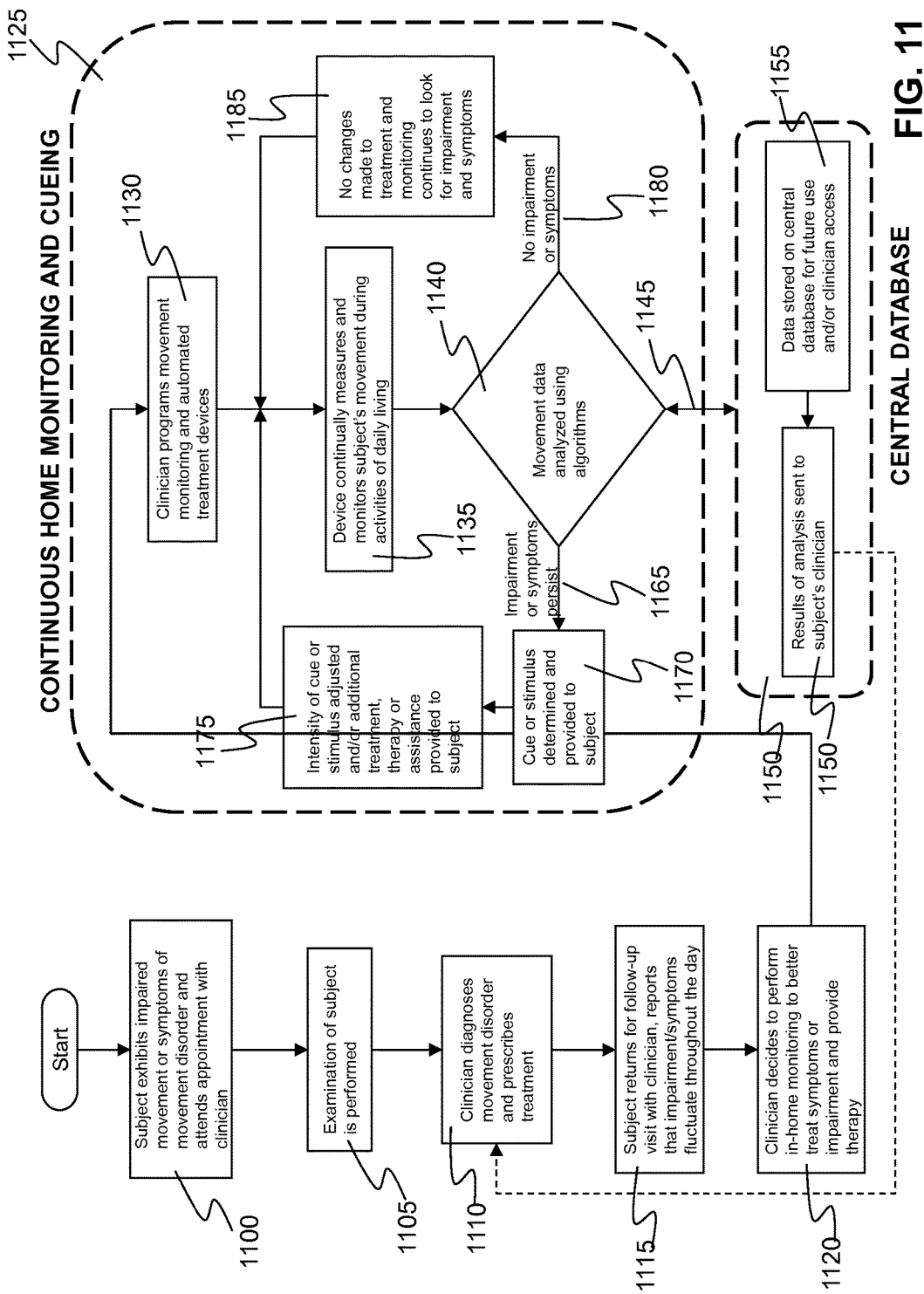
FIG. 11. Flow diagram of an embodiment of the present invention operating in a continuous mode where the subject's movement is continuously monitored outside of a clinical setting, and the system is in communication with a centralized database.

FIG. 11 depicts a flow diagram for large-scale view of use of a continuous monitoring embodiment of the present invention, wherein a subject initially exhibits an injury or impairment, or symptoms of a movement disorder and attends an appointment with a clinician, physician, therapist or technician 1100. At the appointment, the clinician examines the subject 1105, and upon analysis, diagnoses the subject as having suffered an injury or having a condition that leads to impaired movement or unsafe or undesirable movement, or a movement disorder and subsequently orders a treatment 1110. At a follow-up visit, the subject may report that the impairment(s) or symptoms persist, have worsened, or fluctuate greatly throughout the day 1115, even while on a prescribed treatment plan. The clinician then decides to perform in-home continual testing and monitoring 1120 to better determine the severity of the subject's impairment or symptoms, and to provide continuous therapy or treatment of the subject's impairments or symptoms, and thus the overall injury, condition or disorder. Continuous home monitoring 1125 begins with the clinician programming 1130 any portable therapy system or devices, movement monitoring devices or automated treatment delivery devices for the subject, or instructing the subject how to do so. The portable therapy system or device, containing at least one sensor, preferably an accelerometer or gyroscope of at least three axes, but optionally another sensor(s) capable of measuring motion, such as an EMG electrodes, continually records the subject's movement during activities of daily living 1135. In addition, the device can include two or more types of sensors, preferably at least accelerometers and gyroscopes, or any combination of sensors. Activities of daily living may include folding laundry, handwriting, eating, dressing, self-care, and the like. Optionally, the clinician may order the subject to perform clinical tasks such as finger tapping, nose touching, or the like, as defined by standardized scales such as the UPDRS, Fugl-Meyer, and the like, at regularly scheduled periods, depending on the embodiment and needs of the subject. Such movement data would also be continually recorded.

A trained and/or trainable algorithm, preferably incorporated by at least one computer processor, analyzes the recorded movement data in real-time 1140. The algorithm and processor 1140 function to predict or detect impaired movement, movement symptomatic of movement disorders, instability or imbalance, or other impairments or unsafe or undesirable movement conditions, and/or to distinguish voluntary motion of activities of daily living or clinician ordered tasks from movement disorder symptoms. Some embodiments further comprise algorithms designed to and quantify the severity of the predicted or detected impairments, symptoms, or conditions. In some embodiments, the trained algorithm and computer processor 1140 are also in two-way communication 1145 with a central database 1150 or multiple databases made up of previous subject movement data, disorder histories, treatment histories, and the like both from the particular subject being monitoring and/or from other subjects. Such a database 1150 would preferably retain information from the current subject for use with future subjects 1155 and work with the trained algorithm and processor 1140 to predict and detect impairments and symptoms and to determine cueing strategies and recommended treatment(s) for the current subject based on the previous subject data. This database 1150 could optionally be used as a real-time gateway for providing updates to the subject's clinician 1160 regarding the subject's status.

If the trained algorithm and processor 1140 predict or determine that the subject is exhibiting, or about to experience, movement impairment or movement disorder symptoms 1165, determined cue or stimulus is provided to the subject 1170 in order to allow the subject to address the detected or predicted impairment and either prevent it or correct the movement. If the subject has an automated treatment delivery device, such device may be optionally triggered 1175 if the predicted or detected impairment or symptom is too severe or too sudden for a cue to sufficiently aid the subject. Alternatively, or in addition, the system may determine that the same impairments or symptoms persist and/or the subject has missed or ignored the cues, and the next cue provided may be increased in intensity to notify the subject of the impaired or symptomatic movement. In either event, the subject is made aware of impaired or symptomatic movement and given the opportunity to focus his or her attention on addressing the issue, and/or given assistance in doing so. The portable therapy system or device then continues to record new movement data and the process repeats. If the trained algorithm and processor 1140 determine impaired movement or movement disorder symptoms no longer persist 1180 then no cue, treatment, therapy or assistance is needed, none are provided and changes are made 1185 to the system, and the device continues recording movement data.

Figure 12:
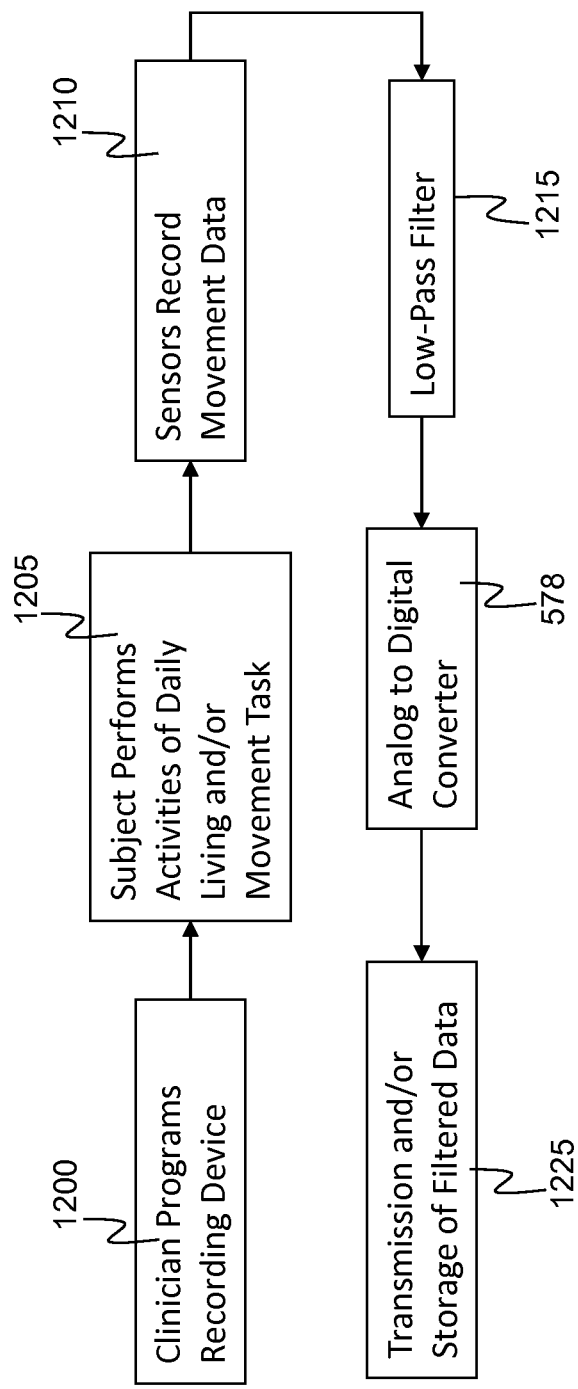
FIG. 12. Flowchart of exemplary and preferable data pre-processing steps.

FIG. 12 depicts preferable steps for preprocessing recorded movement data before extracting kinematic features subject to predict or detect impaired or symptomatic movement and providing a cue to the subject. Preferably this preprocessing is contained within the movement measuring apparatus or portable therapy system or device, such as part of the transceiver unit or circuitry, and consists of one or more electronic components. In various embodiments, a clinician first programs the recording device 1200 to measure only at specific times or from specific sensors, or preferably to measure continuously. Next, the subject performs movement tasks or simply uses the device during activities of daily living 1205 according to the clinician's orders, either during specified tasks at the clinician's office, or at home during activities of daily living. While performing these tasks, the sensors of the movement measuring apparatus or portable therapy system or device, preferably a combination of accelerometers and gyroscopes, record the subject's movement data 1210. Once the movement data is recorded, preferably a low pass filter 1215 is then used to remove artifacts (including movement and electrical interference) or information known to those skilled in the art which would be unrelated to the subject's movement. Preferably the low pass filter 1215 allows only frequencies less than 100 Hz. Even more preferably, the low pass filter allows only frequencies less than 50 Hz. Even more preferably, the low pass filter allows only frequencies less than 30 Hz. Still more preferably, the low pass filter allows only frequencies less than 20 Hz. Next, an analog to digital converter (ADC) 1220 may be used to digitize the data for future processing. Preferably, the ADC samples the recorded movement data at a rate of 128 Hz. Finally, the filtered data is either immediately transmitted or stored on board for later transmission 1225 to a central database or processor for use by a trained cueing and/or treatment customization algorithm.

Figure 13:
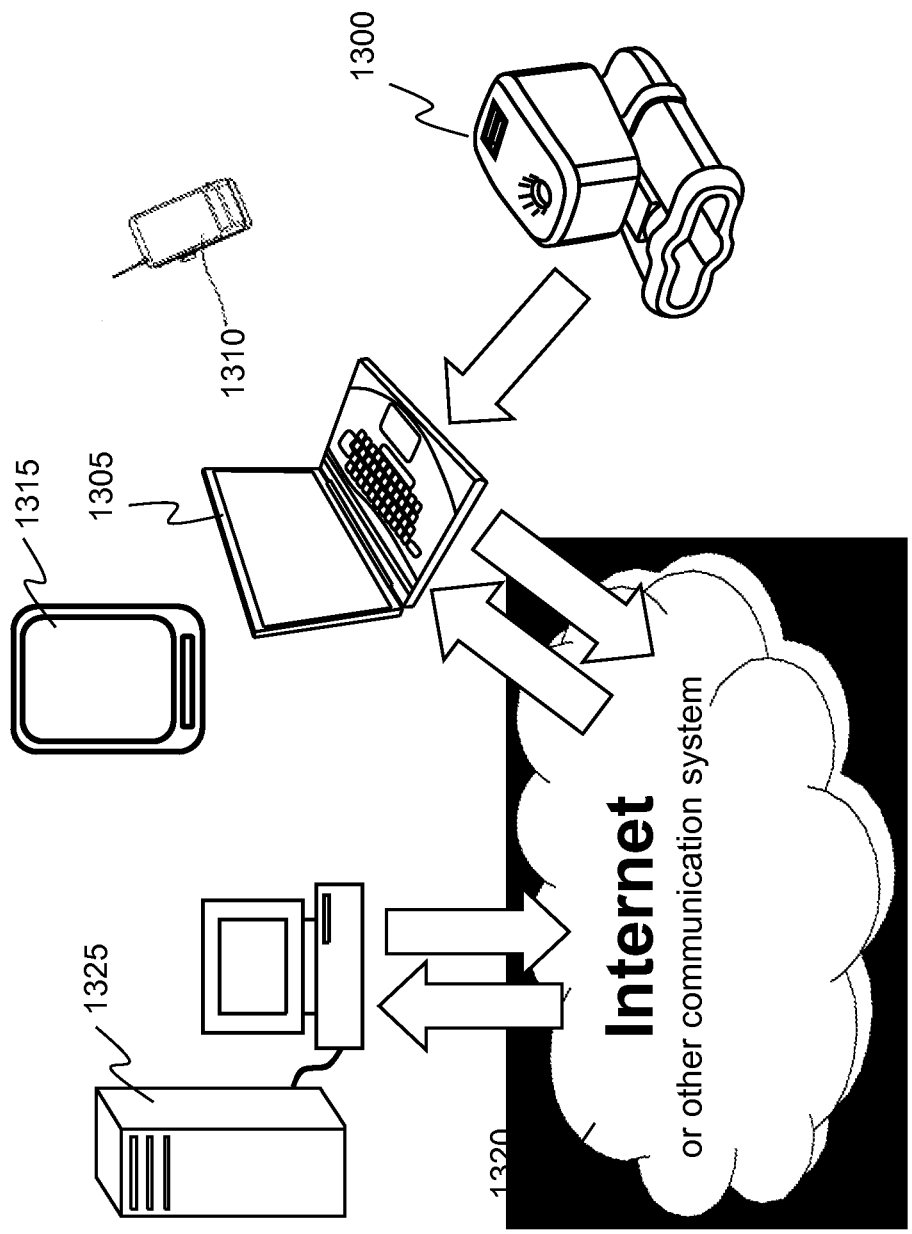
FIG. 13. Exemplary, graphic depiction of data flow between various components of the system of the present invention.

FIG. 13 illustrates one embodiment of a general data relationship between subject worn sensors, a processor, and an adaptive central database. A movement measuring apparatus or portable therapy system or device, comprising at least one sensor 1300, depicted as a finger-worn sensor unit, is worn by a subject (not shown) and records movement data while activated. The at least one sensor 1300 is preferably an accelerometer, a gyroscope, or more preferably, a combination of the two, as previously described in this application, and can be of any such variety described and worn on any part of the subject's body. The recorded movement data is then either preprocessed, perhaps by transceiver module or transceiver circuitry (not shown), or transferred directly to a processor for preprocessing and/or further processing. The processor is preferably comprised in the portable therapy system or device 1305, 1310 or 1315. The processor uses a trained algorithm to predict or detect impaired movement, unsafe or undesirable movement or conditions or symptoms of movement or other disorders, and to generate cues for the subject to notify him or her of the predicted or detected impairment or symptom so that the subject may address and predict or correct the impaired movement. Some embodiments may utilize a central database 1325 to store movement and cueing data, as optionally to coordinate movement data measured from the particular subject with past information from the particular subject or other subjects in order to train the algorithm to better predict or detect impairments and provide cues. Communication with the central database 1325, can be in any form, wired or wireless, as described above or known to those skilled in the art. The present figure illustrates the communication system as the internet 1320 indicating the contemplation of known wireless communication and data transferring systems for communication between the portable therapy system or device and the database, however, this is merely by way of example, and meant to represent wireless communication as whole. As the processor of the portable therapy system or device 1305, 1310, 1315 uses a trained algorithm to predict or detect impairment or symptoms and provide cues or stimuli, correlate data and optimize a custom treatment for the subject, data is continually sent from the portable therapy system or device 1305, 1310, 1315 to the central database 1325 and from the central database 1325 to the portable therapy system or device 1305, 1310, 1315 for the purposes of transmitting and storing the subject's newly recorded movement data and cuing data, retrieving previous subject movement, cueing and treatment data from the database, and determining an optimized and custom cueing and/or treatment protocols for the subject. Once the portable therapy system or device 1305, 1310, 1315 and central database 1325 contain the subject's new customized treatment, the subject or a third party, such as a clinician, can be alerted to retrieve the customized cueing and/or treatment by transmission to the portable therapy system or device 1305, 1310, 1315 or other communication such as a printout, email, direct access to the data and protocol on the database, or the like.

Figure 14:
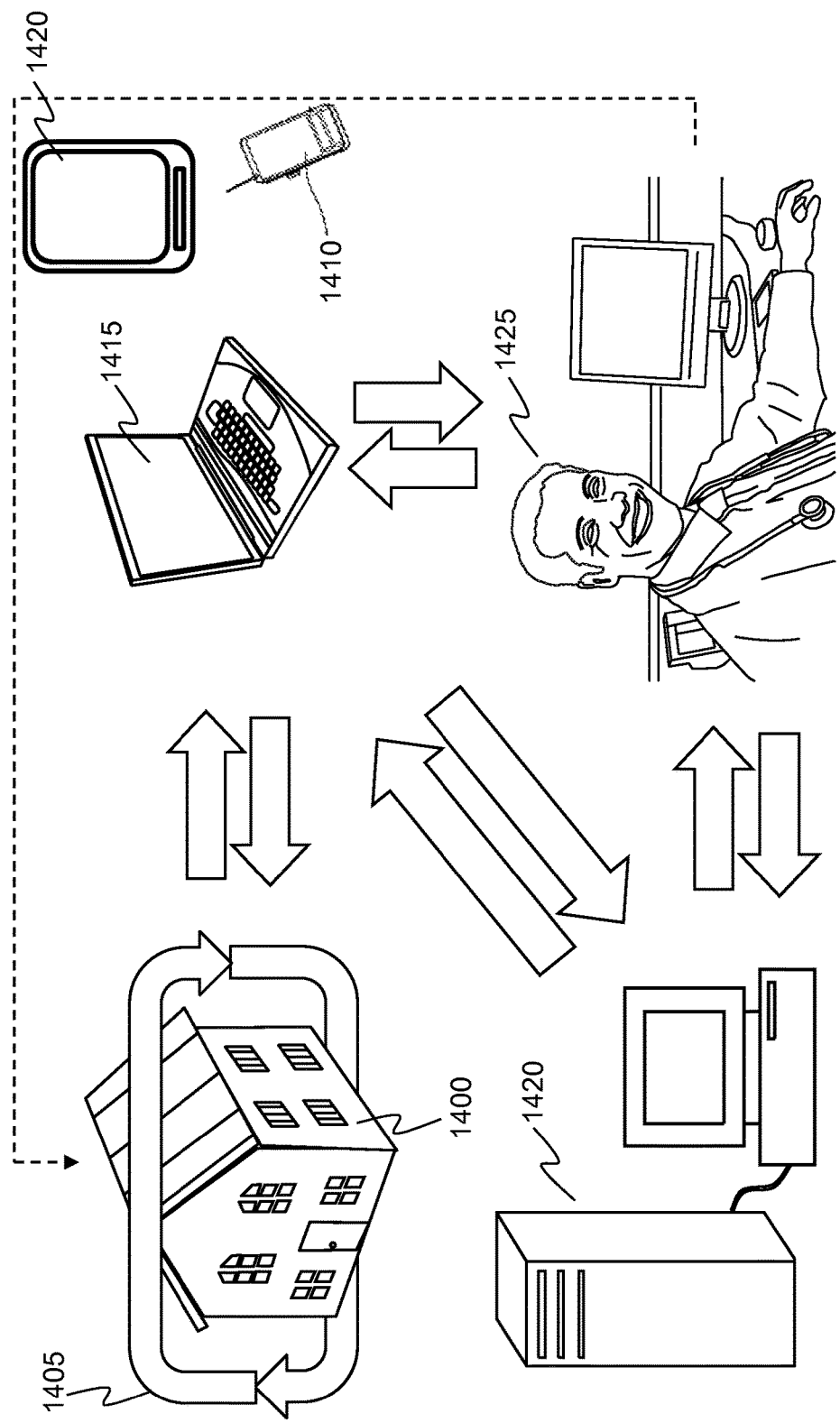
FIG. 14. Exemplary, graphic depiction of data flow in embodiments employing continuous home movement recording, and optionally, treatment, with the ability for remote clinician intervention.
Figure 15:
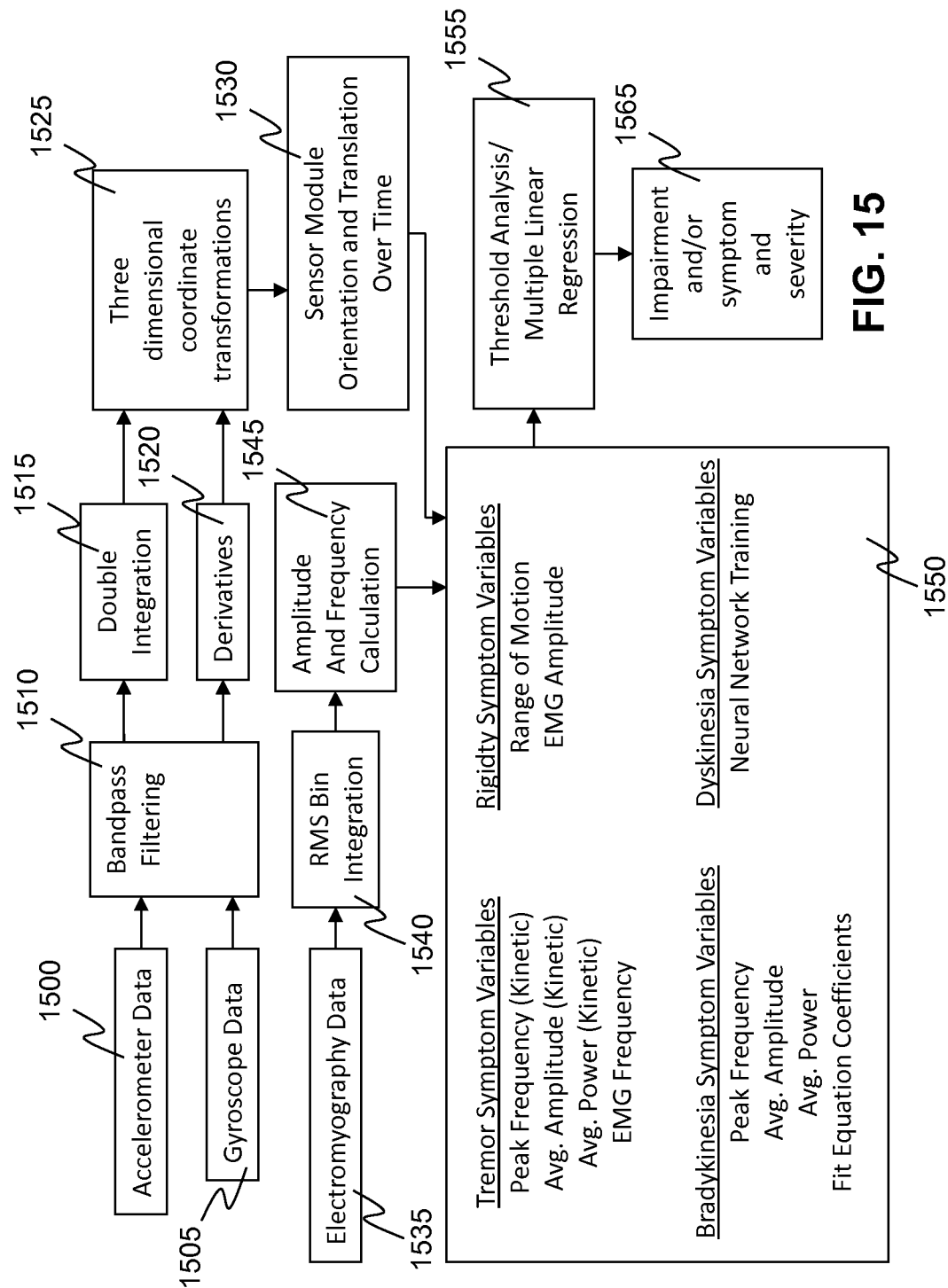
FIG. 15. Flow diagram for one embodiment of the software/algorithm(s) used in the present invention to measure movement disorder symptoms and provide therapy for such symptoms.

FIG. 14 illustrates continuous home movement monitoring and cueing and treatment tuning with the ability for remote clinician intervention. A subject (not shown) inside the home 1400, the home being representative of any non-clinical setting the subject may use the portable therapy system or device to measure movement, wears a movement measuring apparatus or portable therapy system or device 1410, 1415, 1420 while performing activities of daily living. While performing the activities, the movement measuring apparatus or portable therapy system or device 1410, 1415, 1420 continually records 1405 the subject's movement data. The movement measuring apparatus or portable therapy system or device 1410, 1415, 1420 in this embodiment can then using a trained algorithm, predict or detect movement impairment or symptomatic movement based on the measured movement data. Optionally, the portable therapy system or device 1410, 1415, 1420 can also correlate the subject's continuously recorded movement data with a central database 1420 to determine a custom cueing and/or treatment protocol. Once the portable therapy system or device 1410, 1415, 1420, and optionally the central database 1420 contain the subject's new customized cueing and/or treatment protocol, a remote third party, such as a clinician 1425, can be alerted to or retrieve the customized cueing and/or treatment protocol from the portable therapy system or device 1410, 1415, 1420 or the central database 1420 via the internet or other communication system. The clinician 1425 may then intervene and provide a new or additional cue or stimulus to the subject, establish a new cueing protocol, or prescribe a new treatment protocol based on movement data scores from the portable therapy system or device 1410, 1415, 1420 or central database 1420. Additionally, the portable therapy system or device 1410, 1415, 1420 may output the new recommended cueing or treatment protocol on a screen or display for the subject to see, who may then begin the new treatment without clinical intervention, or automatically program the subject's treatment device. Another important feature and capability of the system is that of providing tracking of impairments of movement. As the system continually measures and monitors the subject's movement to detect impaired movement, it can output an indication of the type and degree of impairment, with or without an attendant cue that is aimed at making the user and/or clinician aware of the subject's specifically experienced impairments. This is particularly useful for embodiments that utilize a personal device such as a smartphone and application to provide the user with constant, and instant notification and feedback. In such cases, the impairment indication can be displayed for each instance as it occurs and/or can be displayed on demand by a user and show individual impaired movement instances, or trends over a period of time to track and show how the subject's impairment changes throughout the day and in response to various influences such as therapy, medication, time of day, subject's activity, and the like. Thus, the system keeps track of the impaired movement instances and allows for a robust review of the data in many forms, all of which are aimed at increasing the subject's and/or clinician's awareness of the subject's impairment in order to provide more targeted therapy or treatment. The system may also provide a comparison of the subject's measured impaired movement against preset, predetermined or known goals in order to provide further awareness of the subject's level of impairment and tracking in relation to the set goals. FIG. 15 is a flow diagram for one embodiment of the software used in the present invention that, aside from providing a cue to the subject regarding predicted or detected impairment, also provides a quantification of impairment or symptom severity and bases the cue not only on the impairment or symptom, but the severity as well. Analog outputs from the accelerometer and gyroscope 1500, 1505 are converted to linear acceleration and angular velocity with a scaling factor. The linear accelerations and angular velocity inputs are then bandpass filtered 1510 to prevent biasing and remove DC drift. The linear acceleration is double integrated 1515 to yield linear position. The derivative 1520 of the angular velocity is calculated to determine angle. The three dimensional translation and rotation 1525 of the module is computed from the information from the three orthogonal accelerometers and three orthogonal gyroscopes, or more preferably, the single three-axis accelerometer and single three-axis gyroscope. Sensor module data is continuously checked for orientation and such data translated continuously 1530. The root mean square (RMS) value 1540 of the continuous time EMG signal and data 1535 is calculated over discrete time windows. The amplitude and frequency 1545 of the processed EMG signal is calculated. Specific variables are then computed for each movement impairment or movement disorder symptom based on the processed kinetic and EMG data 1550. Postural sway variables will include peak trunk angular velocity, and magnitude of high velocity trunk orientation changes. Tremor symptom variables may include but are not limited to the peak frequency of the kinetic sensors, the average amplitude of the kinetic sensors, the average power of the kinetic sensors, and the frequency of the EMG signals. Bradykinesia symptom variables may include but are not limited to the peak frequency of EMG or kinetic data, the average amplitude of the kinetic sensors, the average power of the EMG or kinetic sensors, the number of hesitations that occur in a subjects movement, or the linear or exponential fit coefficients used to fit a model to the amplitude of a subject's movement over time. Abnormal muscle tone (e.g. rigidity, spasticity, dystonia) symptom variables may include but are not limited to range of motion and EMG amplitude. The value of each symptom variable for a particular symptom is used in an algorithm that may include but are not limited to models for comparison of measured or derived kinematic feature values against predetermined thresholds, multiple linear regression models or neural network models 1555 to predict or detect movement impairment or symptomatic movement, and to use the impairment and/or symptom variables to calculate algorithmic calculations for determining a quantified value for the severity of the impairment and/or symptom 1560. Finally, a cue or stimulus, and possibly treatment or assistance is provided 1565 to the subject where the cue/stimulus and/or treatment or assistance is based on the predicted or detected impairments or symptoms and the calculated severity of each. The greater the severity or urgency, the more urgent the cue/stimulus and the higher likelihood that treatment or assistance must be provided as well.

Figure 16A:
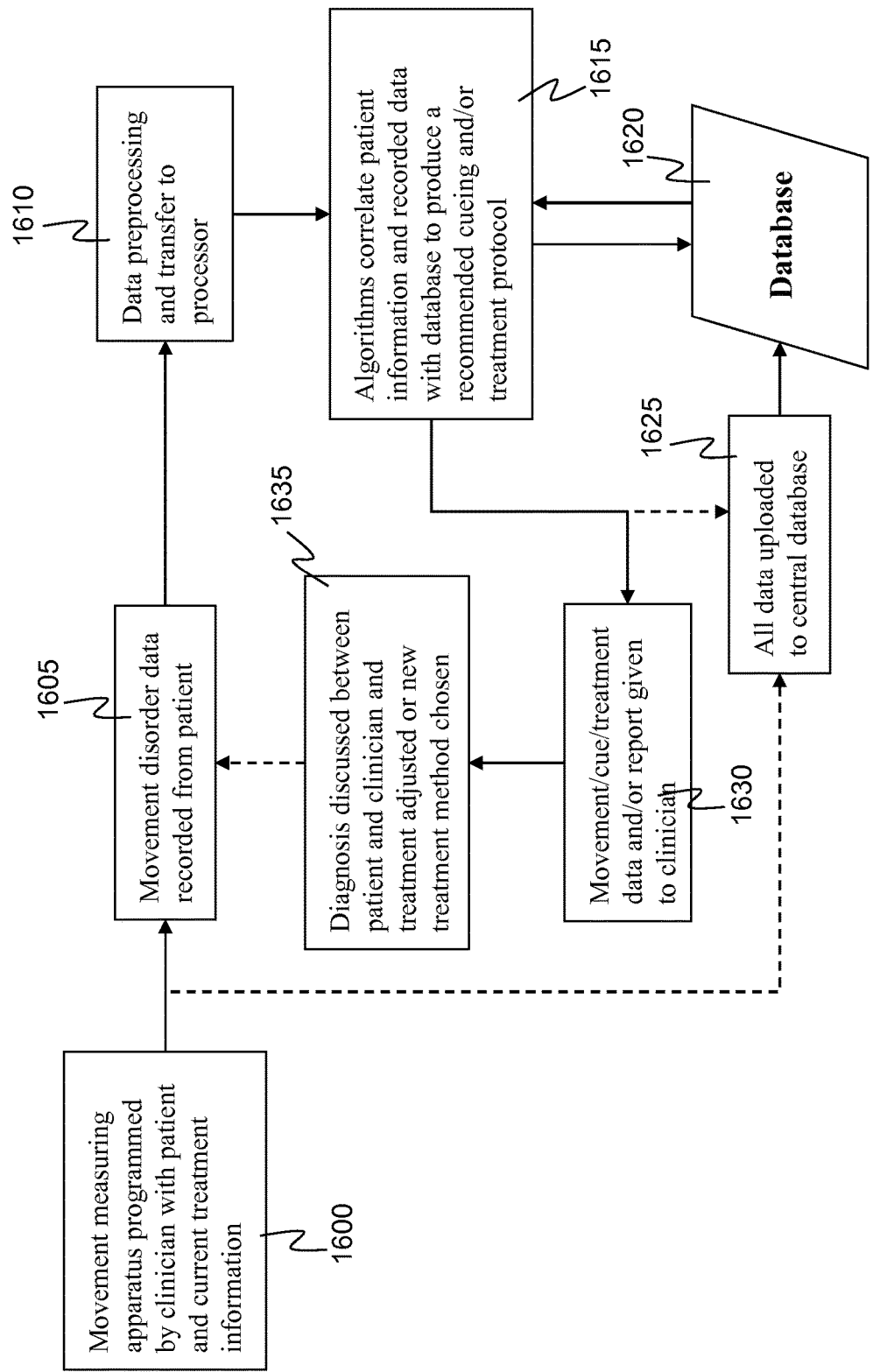
FIGS. 16A-16B. Flow charts depicting the relational processes between a movement measuring apparatus or portable therapy system or device, data, algorithms, clinician, subject, database, and treatment devices for: 16A) reporting systems providing a report to a clinician and allowing feedback or intervention by the clinician; and 16B) automated treatment systems.
Figure 16B:
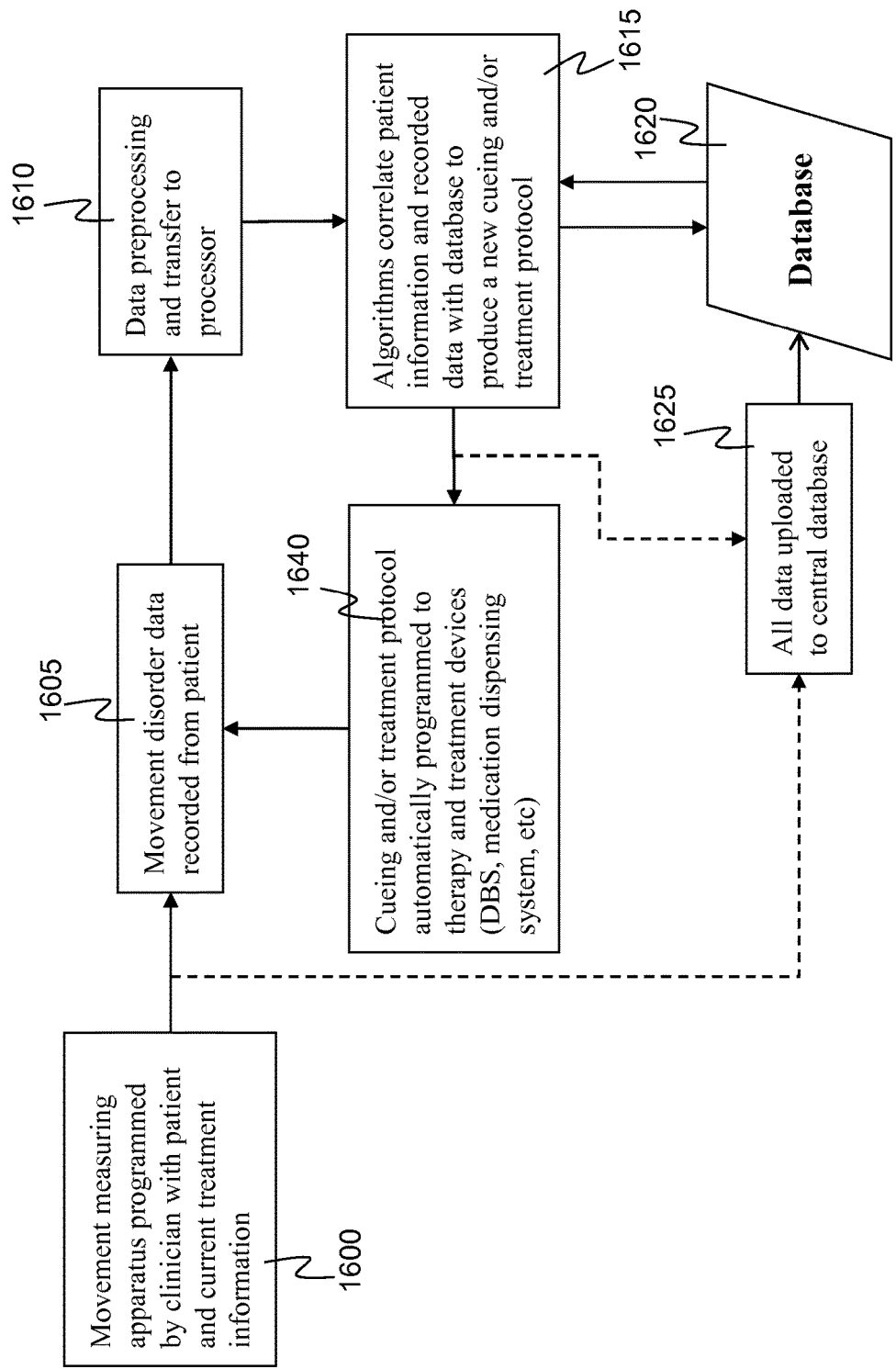

FIGS. 16A and 16B depict the relational processes between a movement measuring apparatus or portable therapy system or device, data, algorithms, clinician, subject, database, and treatment devices in many embodiments of the present invention. The first step in this process is the programming of the movement measuring apparatus or portable therapy system or device by the clinician 1600. In some embodiments, such recording will include the recording parameters, such as timing, and from which sensors, as well as information regarding the subject, such as their demographics, disorder and treatment history, and the like. Optionally, this data can be immediately uploaded 1625 to a central database 1620 so as to create the most adaptable database possible for use in future cueing and treatment determinations. Next, movement data is recorded from the subject 1605, preferably from at least three-axes each of accelerometer and gyroscopic sensors. The data is then either preprocessed by an optional, separate transceiver unit and transferred 1610 to a primary processor on the portable therapy unit, or transferred directly the portable therapy unit and preprocessed by components thereupon. Next, a trained algorithm can be used 1615 by the portable therapy unit's processor to predict or detect impairments or symptoms and optionally correlate 1615 the recorded movement data and prediction or detection data with a database. Preferably, there is two-way communication between the portable therapy system or device and database or other remote data source. The purpose of such communication is to look for which subject histories in the database are relevant, retrieve that information, and correlate the current subject information with the retrieved database information in order to produce a more customized and optimized cueing and/or treatment protocol. Optionally, this treatment information is immediately uploaded 1625 back to the central database 1620, when included, so as to create the most adaptable database possible for use in future cueing and/or treatment determinations. In FIG. 16A, a cue or stimulus is then provided to the subject and cueing and treatment report is given to a clinician 1630, after which the treatment is either ordered and the subject's portable therapy system or device and treatment device (an electrical stimulator, automated medication delivery device, or the like) are re-programmed, or discussed with the subject 1635. In FIG. 16B, after a cueing and/or treatment protocol is determined, the treatment protocol is automatically programmed 1640 in the portable therapy system or device and treatment device (an electrical stimulator, automated medication delivery device, or the like).

Figure 17:
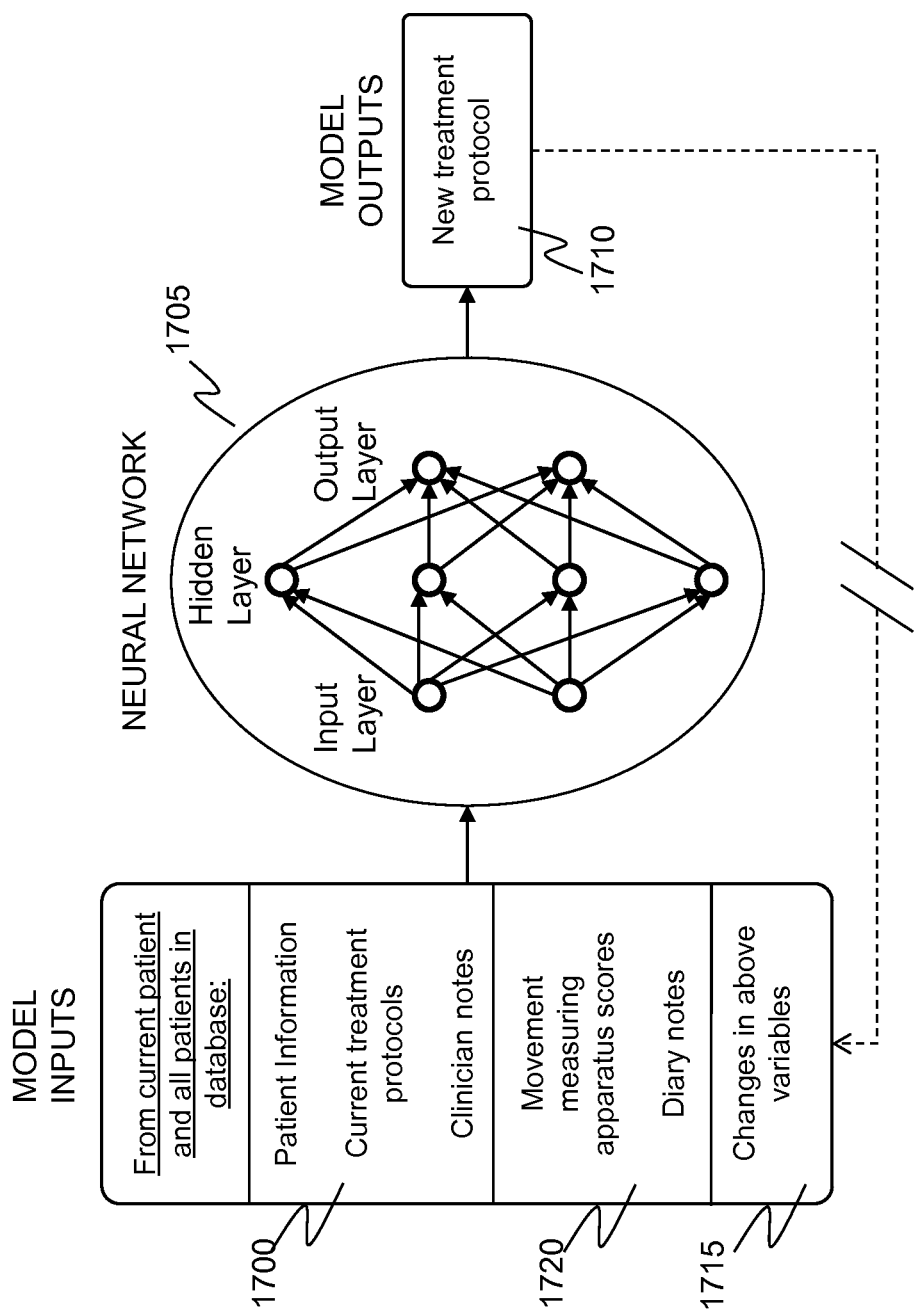
FIG. 17. Illustration of a preferred multilayer perceptron artificial neural network model for analyzing movement data to provide a suggested treatment or therapy protocol.

FIG. 17 is an illustration of the preferred embodiment of an artificial neural network algorithm used in correlating current subject data with a central database for determining a subject customized cueing and/or treatment protocol. The neural network itself 1705 is preferably a feedforward model trained through backpropagation techniques and consisting of an input layer, hidden layer, and output layer. Preferably, there are multiple input layers, including but not limited to, clinical data and definitions 1700 such as current subject demographics, disorder history, treatment history, clinician notes, and the like; subject data 1720 such as recorded movement data, diary information, and the like; and a dynamic input 1715 to account for changes in any of the other input variables with respect to time. The many inputs allow the algorithm to analyze complex data trends and dynamic interactions. Furthermore, multiple input layers allow constraints on the algorithm so that only the most appropriate data is used, while a dynamic layer helps optimize the correlation of that data to the subject's dynamic trends, so that the most efficient and optimized results are obtained. Still more preferably, data that is an input to the model is taken from or stored on a central database or database system of similar information for access by future subjects and algorithm training. The model output 1710 is simply the new cueing and/or treatment protocol. While this new cueing and/or treatment protocol may not be automatically fed back into the model input 1700 as in a closed-loop iterative process, the information is preferably added to the central database so that it can be used in the future, thereby increasing the central database's adaptability.

Figure 18:
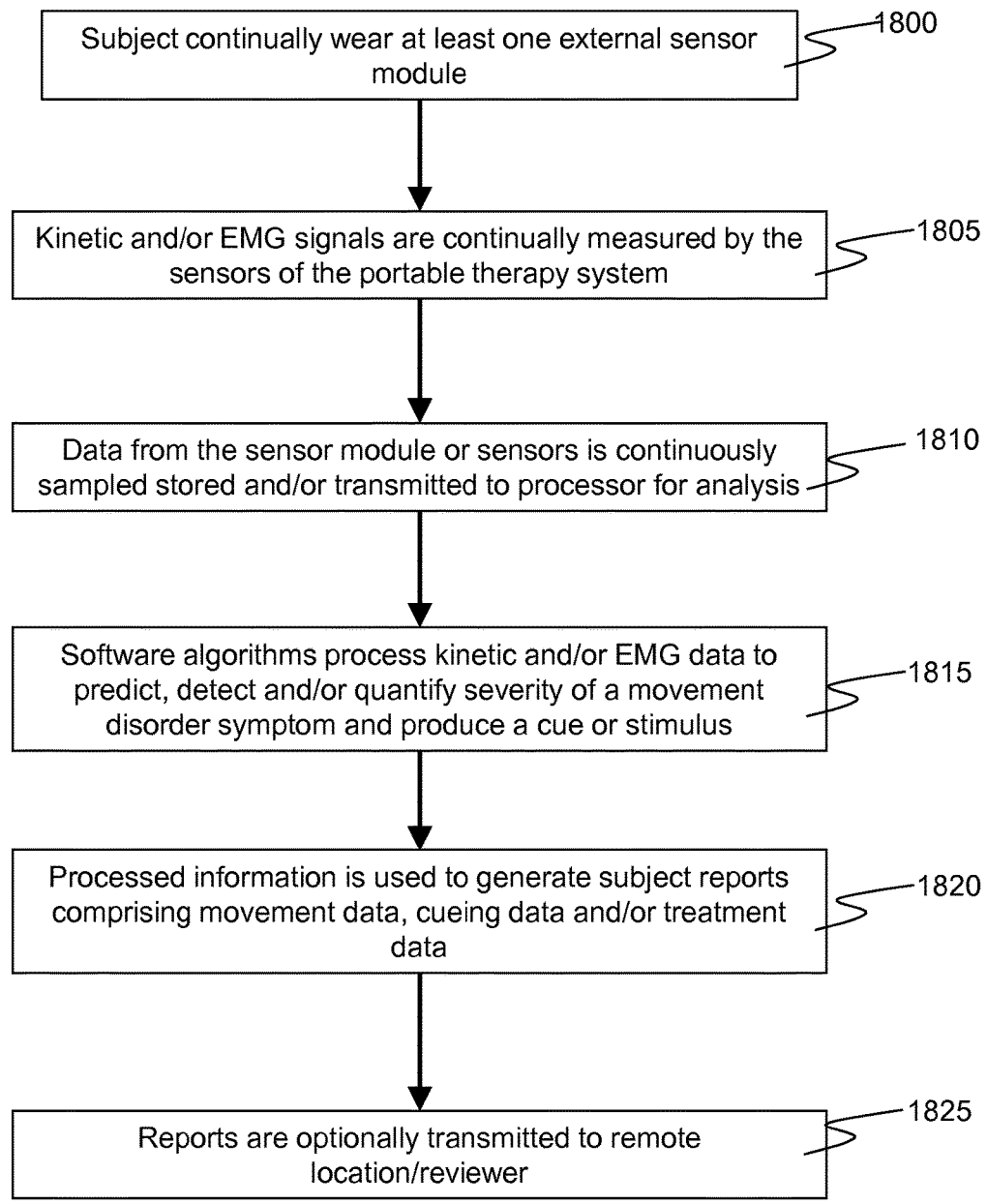
FIG. 18. Flow diagram of an embodiment operating in continuous mode to measure subject movement and generate subject reports containing the subject's movement data, FIG. 19. Flow diagram for one embodiment of a closed-loop drug delivery system of the present invention.

FIG. 18 depicts an optional, exemplary operating mode of the system of the present invention. This embodiment should be viewed as an example, but not a limitation to the present invention, and understood to be one of many methods or modes of using the system of the present invention. The depicted embodiment is a flow diagram for a continuous operating mode or method for the system of the present invention. The subjects continually wear at least one external sensor module or portable therapy system or device 1800. Kinetic motion and/or EMG are continually measured by the external sensor module 1805 or sensors of the portable therapy system or device. Data from the external sensor module or sensors of the portable therapy system or device is continuously sampled and stored to memory within the portable therapy system or device and/or transmitted to the portable therapy system or device by internal electrical connections, hardwired connections or an optional, separate transceiver module 1810. Software algorithms with the processor process kinetic and/or EMG data to predict or detect impairment or symptomatic movement and optionally to quantify the severity of the impairment or movement disorder symptom occurring 1815, and to produce a cue to the subject based on the prediction or detection and quantification. The processed information is then used to generate subject reports or data 1820 comprising at least one of measured movement data, prediction or detection data, and cueing data, and the reports or data are transmitted to technician, clinician or physician for review 1825.

Figure 19:
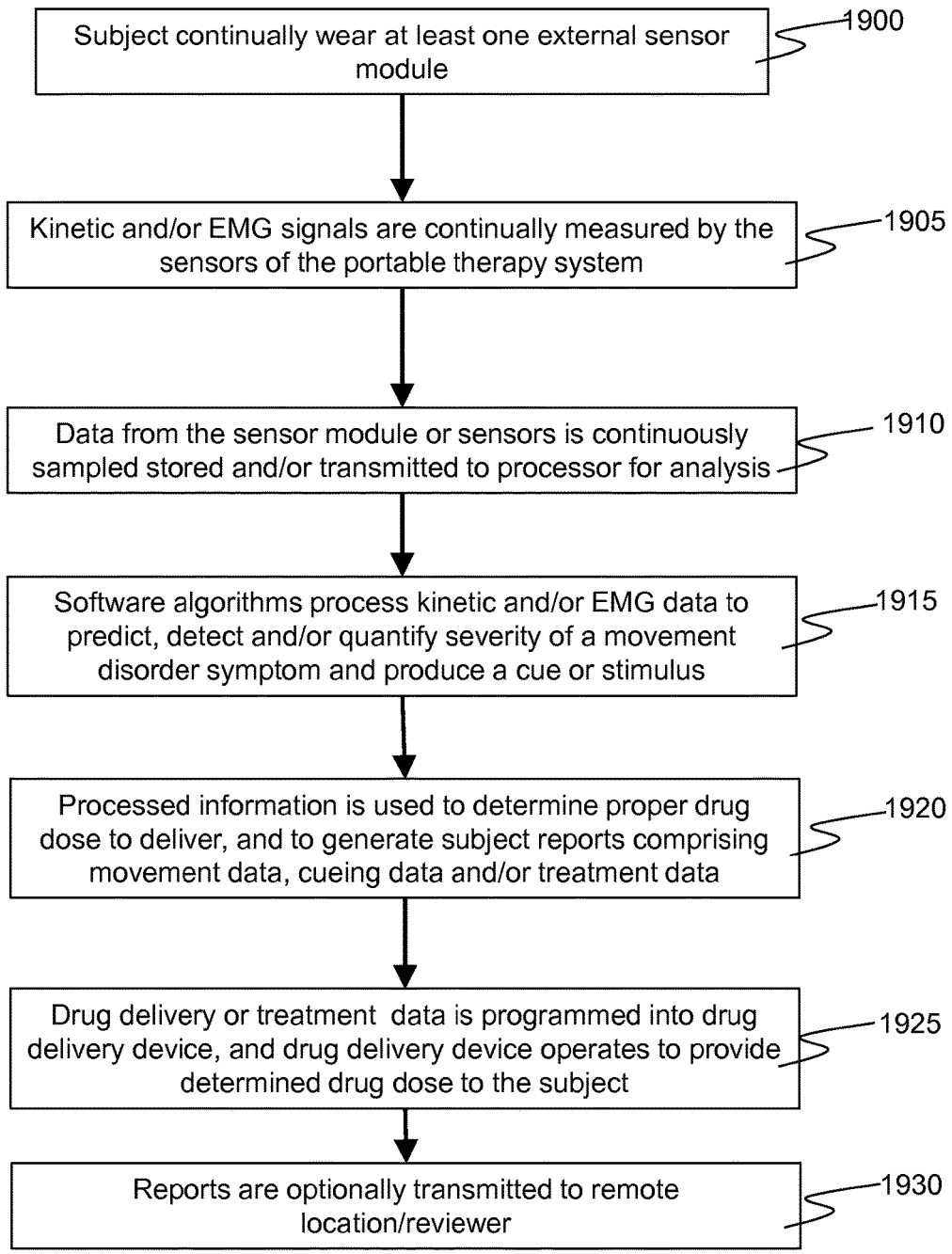

FIG. 19 depicts an optional, exemplary operating mode a flow diagram for one embodiment of a closed-loop drug delivery system of the present invention. This embodiment should be viewed as an example, but not a limitation to the present invention, and understood to be one of many methods or modes of using the system of the present invention. The subjects continually wear at least one external sensor module or portable therapy system or device 1900. Kinetic motion and/or EMG are continually measured by the external sensor module 1905 or sensors of the portable therapy system or device. Data from the external sensor module or sensors of the portable therapy system is continuously sampled and stored to memory within the portable therapy system or device or transmitted to the portable therapy by an optional, separate transceiver module 1910. Software algorithms with the processor process kinetic and/or EMG data to predict or detect impairment or symptomatic movement and optionally to quantify the severity of the impairment or movement disorder symptom occurring 1915, and to produce a cue to the subject based on the prediction or detection and quantification. The software algorithms trigger the release of medication based on the subject's impairments or symptoms, any quantification, and the cues 1920, or the overall severity of the movement disorder. The treatment protocols can further be programmed into the device for continued operation under those parameters 1925, depending on the particular embodiment and the impairment or symptom predicted or detected. The processed information is then used to generate subject reports or data 1930 comprising at least one of measured movement data, prediction or detection data, cueing data, and treatment data, and the reports or data are transmitted to technician, clinician or physician for review 1930.

Figure 20:
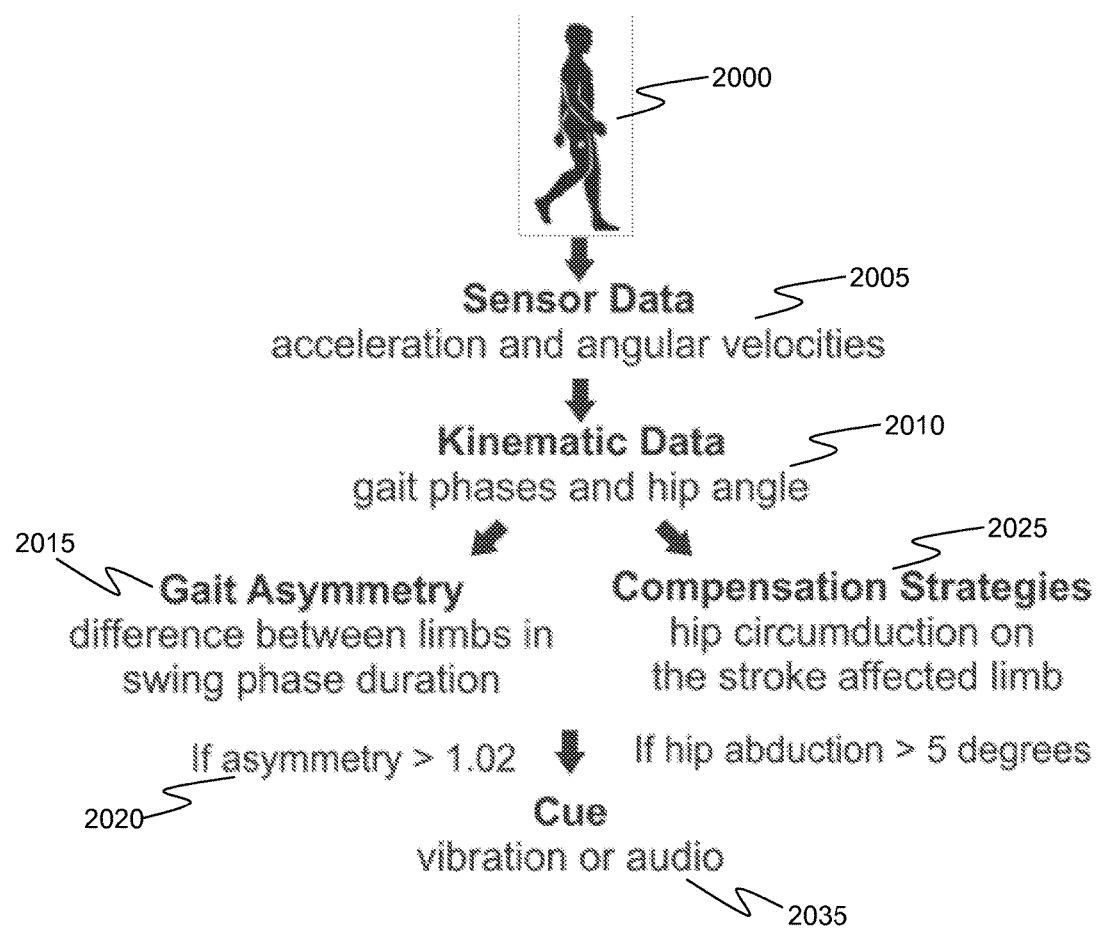
FIG. 20. Illustration of an exemplary cuing embodiment wherein the subject's movement is measured and the system provides a cue notifying the subject of measured or determined gait, balance or posture impairment or movement disorder symptom so that the subject can correct or address the impairment or symptom.

FIG. 20 depicts the cueing or stimulus methods and the data flow involved in determining and providing a cue or stimulus. A subject 2000 is provided with the portable therapy system or device comprising sensor(s), electronic components for data storage and transmission, processor with algorithm for analyzing data, and the like. Once the subject 2000 dons the portable therapy system or device, it is either turned on or is automatically turned on, and the sensors begin to acquire data 2005 corresponding to the subject's movement or some aspect or feature of the subject's movement. The actual movement data acquired 2005 depends on the particular embodiment and the particular sensor(s) used. Kinematic data is then acquired 2010 by either analyzing, processing, deriving or otherwise manipulation the raw sensor-acquired data. Kinematic data can take many forms and many varieties of kinematic features and metrics may be used by the various embodiments of the present invention. Once sensor and kinematic data have been obtained or calculated, further calculations and derivations are performed by the processor and algorithm of the portable therapy system or device to predict or identify what, if any, impairments, symptoms or other such disordered or unsafe or undesirable movement or conditions are present. In the depicted embodiment, the system predicts or detects gait asymmetry 2015 in the subject's movement, which represents a difference in the swing phase duration or movement pattern of each of the subject's limbs, and the system further detects that the subject is employing compensation strategies 2025 to overcome the impairment such as hip circumduction of the subject's limb that has been affected by conditions such as stroke or traumatic brain injury or cerebral palsy. With respect to the predicted or detected gait asymmetry, and similarly for postural sway and postural instability, the algorithm compares the measured or calculated kinematic feature value for gait asymmetry to a predefined threshold 2020, in this embodiment a threshold value of 1.02, and similarly for the compensation strategy of hip circumduction, with a threshold value of 5 degrees 2030. Preferably, threshold values will be determined individually for each subject based on his or her individual needs, level of impairment, therapy or treatment protocol, and any other variable that would affect the detection and measurement of impaired movement. For each individual kinematic feature, impairment, symptom, or other identifiable characteristic of the subject's movement that is impaired or symptomatic, if the value of the feature or metric exceeds the predefined threshold, the system provides a cue 2035, or series of cues, preferably discreetly, to notify the subject of the impaired or symptomatic movement so that the subject can focus his or her attention on the impaired or symptomatic movement and prevent or correct the movement to increase the safety and efficiency of the movement.

Figure 21:
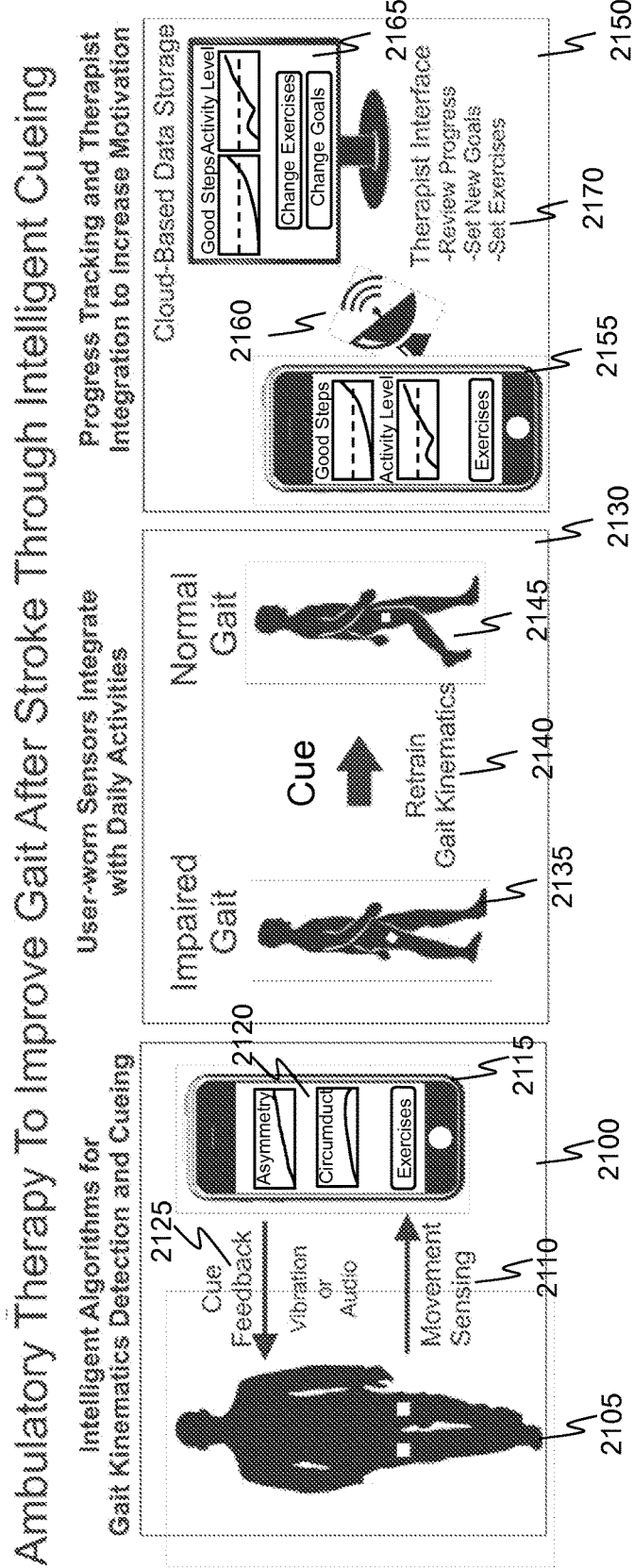
FIG. 21. Illustration of the overall sues and methods of the cuing embodiments of the present invention depicting the subjects movement being measured and receiving a cue resulting from the measured movement, the preferred improvement or result of one impairment where the subject's impairment is improved as a result of learning and training his or movement resulting from the cues, and ongoing support and interaction with clinicians to ensure proper training and improvement.

FIG. 21 depicts the process of improving a subject movement after the subject has suffered an injury or condition that affects movement, such as traumatic brain injury, stroke, or the like, through the use of a portable therapy system or device and cueing of the present invention. Using the system, as shown in the first block 2100, involves, after the subject 2105 suffers an injury or accident or exhibits a disorder or disease that affects movement, the clinician, physician, therapist or technician prescribes and provides the portable therapy system or device to the subject. The portable therapy system or device 2115 measures the subject's movement 2110 and predicts or detects impaired, symptomatic or unsafe or undesirable movement. The device 2115, which can be any device that can comprise or be connected with sensors and contains a processor capable of running the analysis and cueing algorithm(s) (e.g., smartphone with application for analysis, cueing and reporting), determines that a cue or stimulus is required based on the measured movement and predicted or detected impairment, symptom(s) or unsafe or undesirable conditions and provides the cue or stimulus 2125 to the subject. The cue or stimulus notifies the subject that impaired or symptomatic movement is imminent or is occurring, and the subject can react to the cue or stimulus to prevent or correct the movement. Additionally, the portable therapy system or device 2115 preferably comprises an integrated display device 2120, or can communicate data and information to a separate display device, such that information, data, instructions, and other messages can be conveyed to the subject 2105. Similar to above, the cuing and impairment data can be transmitted and displayed for increasing the user's and/or clinician's awareness of the subject's impairments, and for tracking the impairments over time as a function of the variables that may affect the subject's movement such as therapy or medication administered, time of day, subject activity, and the like. The system can then track impairments and show how they change over time, and display those trends in a way that raises the subject's and/or clinician's awareness of individual impairments of movement, and allows for a more targeted approach to counteracting the impairments. The portable therapy system or device 2115 may display identifications of the predicted or detected impairments, symptoms or unsafe or undesirable conditions, quantified values of the severity thereof, trend displays showing how the movement is improving or getting worse over time, or any other piece of data or information available to the system and the user. Additionally, the system may output recommended exercises, treatments plans, commands, warnings, or other such messages to give the subject 2105 more guidance in how to best react to the cue or stimulus. These outputs can be altered based on the tracked impairments in order to provide the best method of treatment or therapy to address the subject's impaired movement. Further, the outputs themselves become part of the tracking process whereby the exercises, treatment plants, warnings or other messages are tracked, and the subject's movement is continually monitored as it changes as a result of the various outputs. Thus, the system can track the effect that the outputs, and implementation of the outputs, have on the subject's impaired movement to provide increased awareness, not only of the impairments themselves so the subject can focus thereupon, but also on the effect that various exercises, treatments, therapies, or the like have on the impairments, therefore providing a more efficient and targeted approach to reducing the level of impairment in the subject's movement.

The second block 2130 depicts the therapeutic intent of the present invention. A subject with impaired, symptomatic or unsafe or undesirable movement 2135 uses the devices, methods and symptoms of the present invention, which predict or detect impaired, symptomatic or unsafe or undesirable movement and provide cues or stimuli 2140 to the subject so that the subject may react to the cues, focus on the impaired, symptomatic of unsafe movement, and prevent or correct such movement. Over time, as the device is continuously used while subject performs activities of daily living, the system will typically predict or detect, and provide cues or stimuli corresponding to, the same or similar impaired, symptomatic or unsafe or undesirable movements repeatedly. This is due to the fact that whatever injury, disorder, disease or condition that is causing the impaired, symptomatic or unsafe or undesirable movement is likely to cause the same impairment or symptoms repeatedly. Thus, the cues continuously remind the subject that the same impairment(s), symptom(s) or unsafe/undesirable movement(s) is repeating, and the subject is continuously reminded to address the same movement. Ideally, over time, with the subject's repeated and continuous focus on the recurring impairments or symptoms, the subject trains himself or herself to overcome the impairments or symptoms, and regains normal movement 2145. Thus, the system ideally provides therapy and training for the subject to naturally regain normal movement by cueing the subject to focus on performing normal motion each time the impairment or symptom arises.

The third block 2150 depicts the clinical aspect of continuous at-home monitoring and therapy. The system, though independent and allowing the subject to receive therapy and training outside of the clinical setting, still required at least occasional interaction and feedback with a clinician. Preferably, the portable therapy system or device and system 2155 comprises at least one electronic component for two-way communication 2160 with other systems and devices 2165. Preferably, the device and system 2155 are capable of wireless communication 2160 thus allowing the device and system to communicate with remote users (e.g., clinicians) and systems (e.g., databases) for transmitting movement, cueing and therapy data and receiving commands, updates, messages, and the like. Some embodiments utilize subject reports that are regularly or routinely transmitted to a clinician so that the clinician can monitor the subject's progress and send back messages, data, etc. The clinician interface 2170 is either or both in direct communication with the subject's portable therapy system or device 2155 and/or remote databases where subject data may be transmitted for storage and later access. This interaction system allows the clinician, again, to monitor the subject's progress and make changes to the therapy and treatment as might be necessary.

Figure 22:
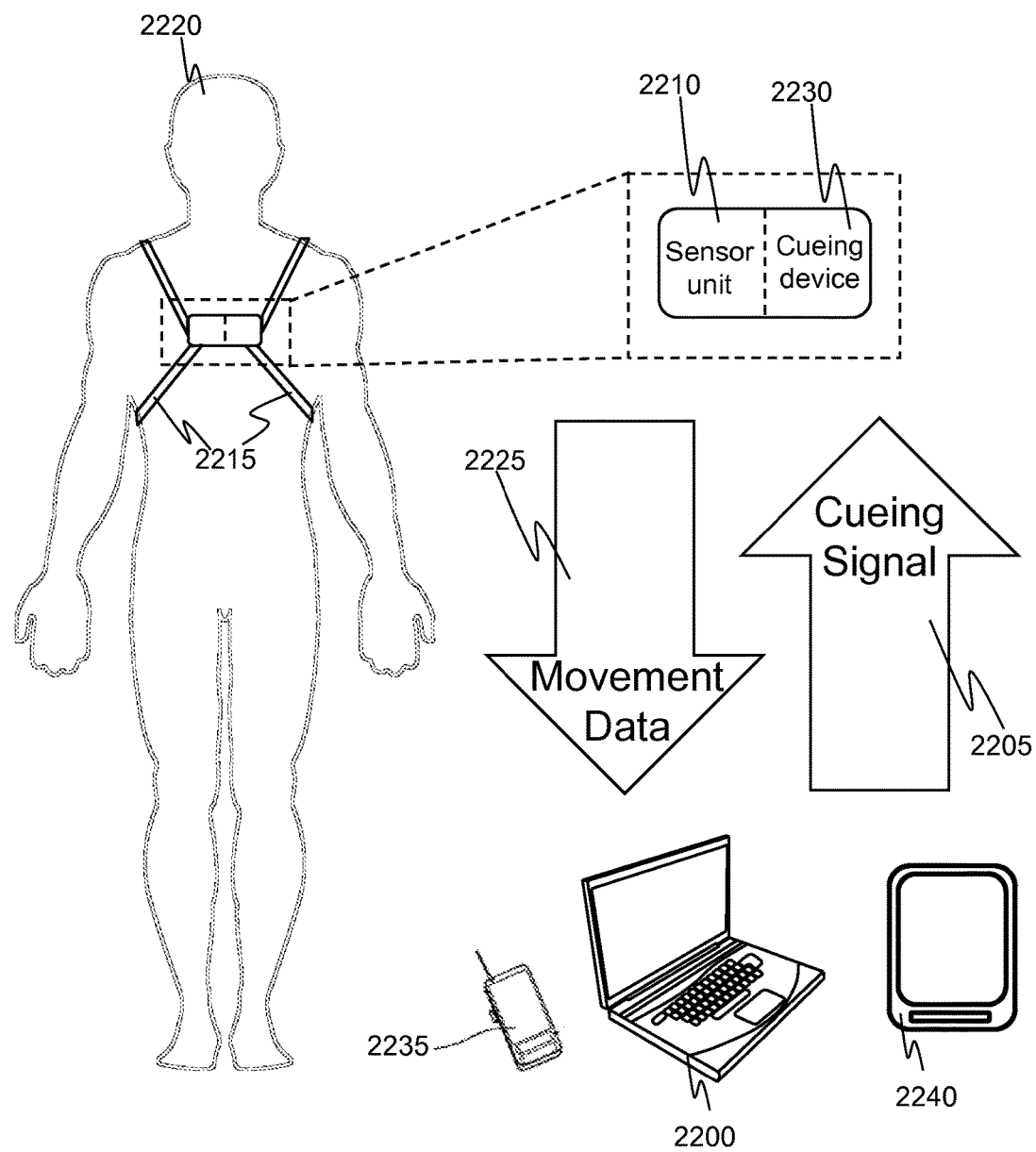
FIG. 22. Illustration of another embodiment of a cuing system wherein the subject wears a movement sensor unit comprising a cuing mechanism whereby the subject's movement is measured and movement data is transmitted to a processing device which, upon determining a movement impairment, signals the device to provide a cue to the subject to correct or address the impairment.

FIG. 22 depicts an embodiment of the present invention particularly useful for purposes of improving the subject's posture, stability and/or balance. In the depicted embodiment, the subject 2220 dons an external sensor device 2210 that may comprise accelerometers, gyroscopes, other sensors, or combinations thereof, and wears the sensor unit 2210 about his or her trunk or torso utilizing a harness or strap 2215 to hold the sensor unit 2210 in place. Both the harness or strap 2215 and sensor unit 2210 can preferably be worn discreetly beneath the subject's clothing to maintain discretion and privacy. The subject 2220 further wears an external cueing or stimulus device 2230, also utilizing the harness or strap 2215 to hold the cueing device 2230 in place. Optionally, the sensor unit 2210 and the cueing device 2230 may be comprised in the same enclosure or housing of a portable therapy device, though each may be separate units or entities attached to or worn by the subject 2220 by virtue of the same harness 2215. In this embodiment, the cueing device 2230 is a vibrational motor that vibrates against the subject chest as a cue. The sensor unit 2210 continuously acquires movement data from the subject 2220 and transmits the movement data to the portable therapy system or device which can include any type of processing unit such as a laptop or other computer 2200, smartphone 2235, or tablet 2240, though other processing unit embodiments are also possible. The portable therapy system or device, and particularly the processing unit, can be any processing device capable of receiving the movement, analyzing said data and transmitting commands or cues as a result of the analysis, and is preferably easily portable and carried or worn by the subject (e.g., smartphone). The portable therapy system or device 2200 analyzes the movement data to predict or detect impaired or symptomatic movement utilizing an algorithm(s) that compare measured and calculated kinematic feature and metric values against thresholds. When a kinematic feature or metric value exceeds (or falls below, depending on the nature of the feature ore metric), the system sends a signal 2205 that a cue needs to be provided, and the cueing device 2230 activates to provide the appropriate cue.

Figure 23:
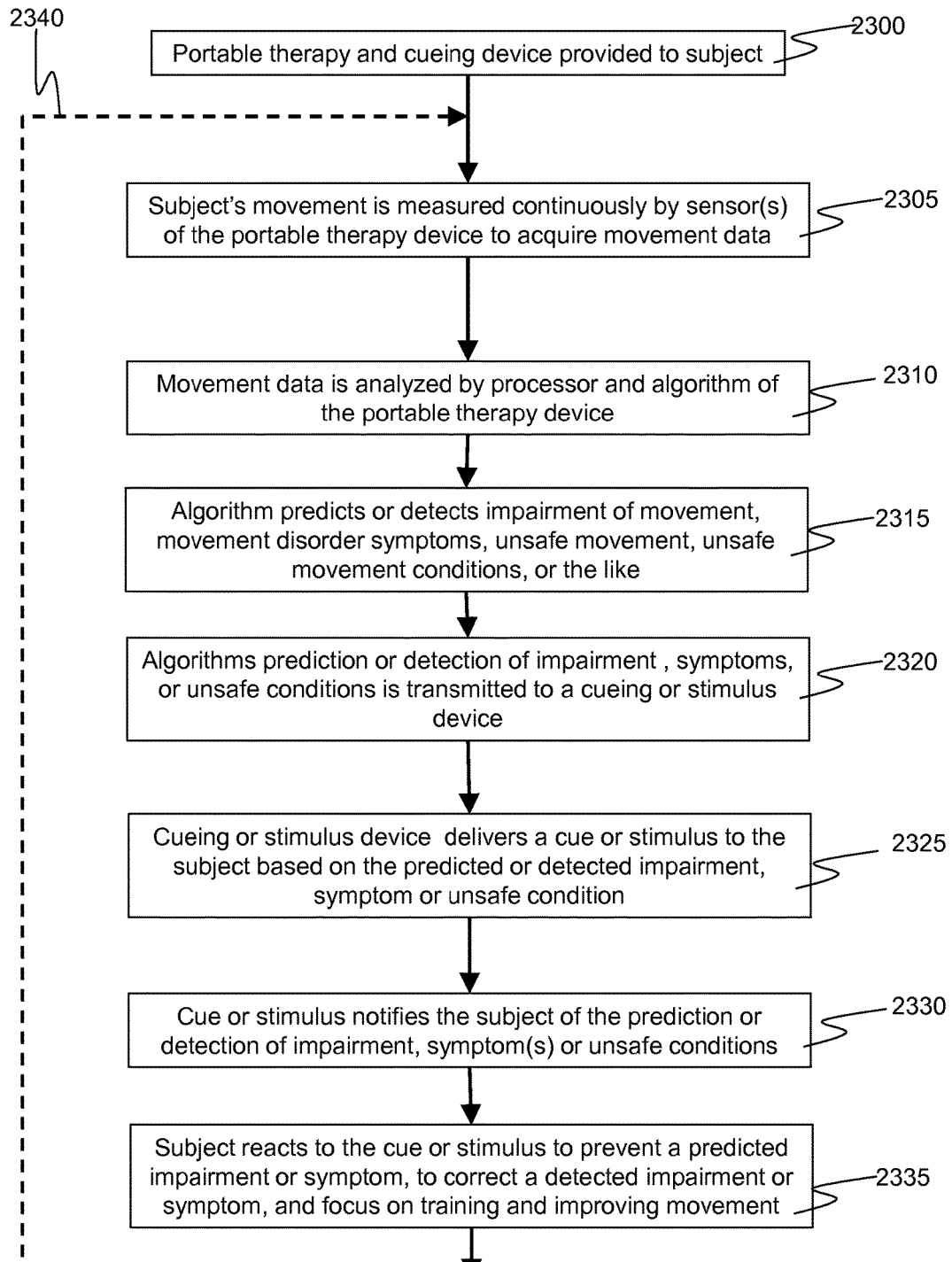
FIG. 23. Flow chart describing steps of method embodiments of the present invention whereby a subject's movement is measured continuously by a portable therapy system or device and the measured movement data is analyzed to predict or determine impaired or symptomatic movement, and a cue or stimulus is provided based on the predicted or detected impairment or symptom(s).

FIG. 23 is a flow chart depicting, in general, various method embodiments of the present invention. The first step is to provide the portable therapy system or device to the subject 2300 so that the subject may don and begin using the device while performing or carrying out activities of daily living. Once the subject dons the system and it is turned on, the portable therapy system or device continuously measures the subject's movement 2305, or some feature or aspect of movement, using the sensor(s) that are part of the system. As the sensors acquire movement data 2305 from the subject, the data is transmitted to the processor which contains an algorithm, and said processor and algorithm analyze the movement data 2310. The analysis of the movement data allows the algorithm to predict or determine 2315 any impairment of movement, symptomatic movement (typically symptoms of movement disorder), unsafe or undesirable movement or movement conditions, or the like. When the algorithm predicts or detects such an impairment, symptom or unsafe or undesirable condition, it generates a signal and transmits that signal 2320 to the cueing or stimulus device to activate the cueing or stimulus device to provide a cue or stimulus 2325 to the subject based on the predicted or determined impairment, symptom or unsafe or undesirable condition. Upon delivery of the cue or stimulus, the subject is notified 2330 that impaired, symptomatic or unsafe or undesirable movement has been predicted or detected, and the subject then reacts to the cue or stimulus 2335 in a manner to prevent, counteract or correct the impaired, symptomatic or unsafe or undesirable movement. As described above, the subject's reaction to the cue is preferably the result of some degree of training or education such that the subject is aware of what a particular cue means, and can react substantially instantaneously and without deliberation or pause to recollect the best reaction to the particular cue. Given that the system is intended to be a continuous monitoring and cueing system, once a cue is provided, the system returns 2340 to the movement measurement step 2305. More accurately, the system will have been measuring movement the entire time, but for purposes of clarification and given that the prediction or detection and cueing steps are all performed in real-time, it can be visualized as a separate step for the system to return from providing a cue to measuring the subject's movement as a result of the cue.

Figure 24:
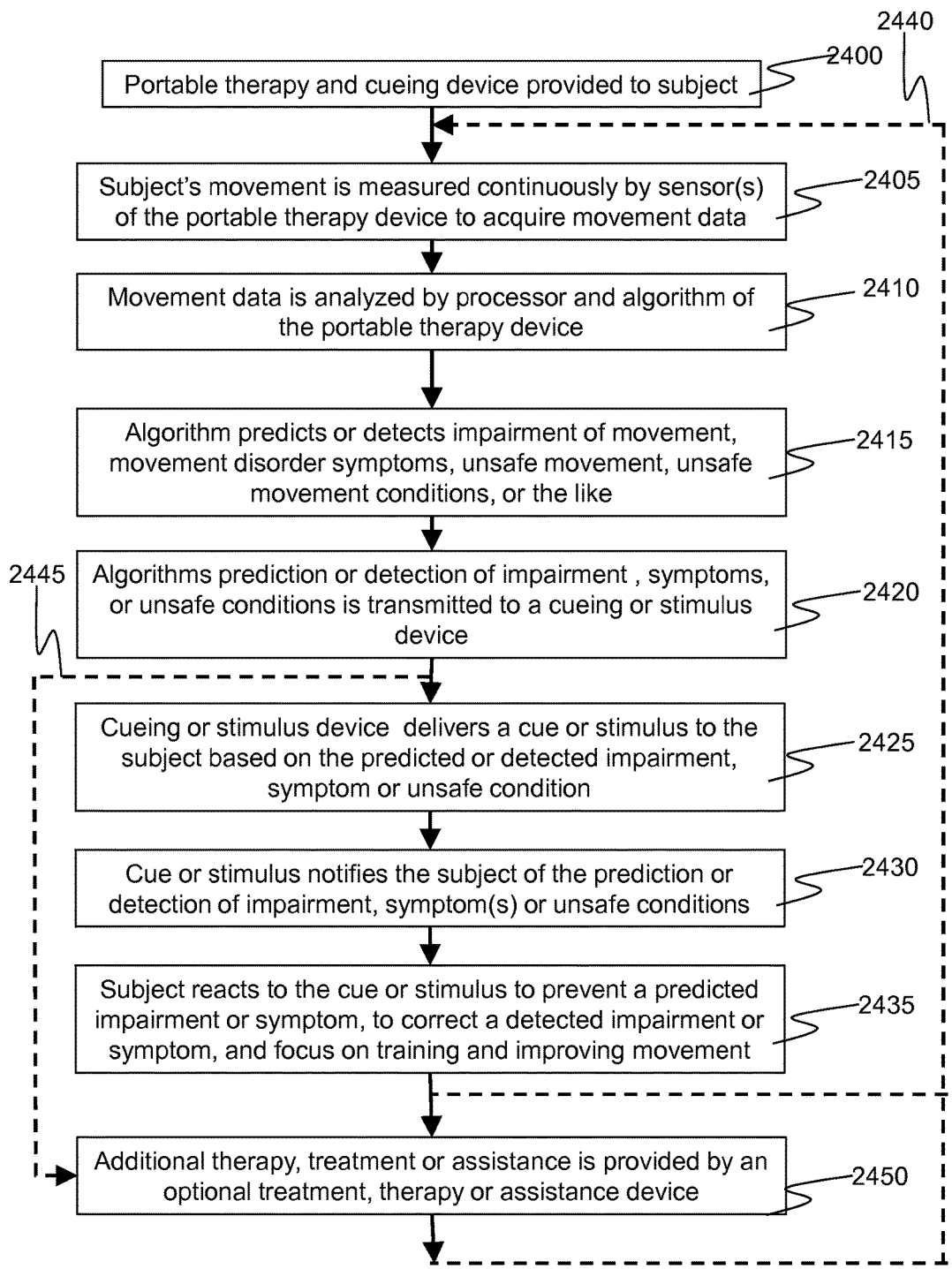
FIG. 24. Flow chart depicting, in general, various method embodiments of the present invention, including a step of providing treatment, therapy or assistance to the subject beyond the cue or stimulus.

FIG. 24 is a flow chart depicting, in general, various method embodiments of the present invention, including a step of providing treatment, therapy or assistance to the subject beyond the cue or stimulus. The first step is to provide the portable therapy system or device to the subject 2400 so that the subject may don and begin using the device while performing or carrying out activities of daily living. Once the subject dons the system and it is turned on, the portable therapy system or device continuously measures the subject's movement 2405, or some feature or aspect of movement, using the sensor(s) that are part of the system. As the sensors acquire movement data 2405 from the subject, the data is transmitted to the processor which contains an algorithm, and said processor and algorithm analyze the movement data 2410. The analysis of the movement data allows the algorithm to predict or determine 2415 any impairment of movement, symptomatic movement (typically symptoms of movement disorder), unsafe or undesirable movement or movement conditions, or the like. When the algorithm predicts or detects such an impairment, symptom or unsafe or undesirable condition, it generates a signal and transmits that signal 2420 to the cueing or stimulus device to activate the cueing or stimulus device to provide a cue or stimulus 2425 to the subject based on the predicted or determined impairment, symptom or unsafe or undesirable condition. Upon delivery of the cue or stimulus, the subject is notified 2430 that impaired, symptomatic or unsafe or undesirable movement has been predicted or detected, and the subject then reacts to the cue or stimulus 2435 in a manner to prevent, counteract or correct the impaired, symptomatic or unsafe or undesirable movement. As described above, the subject's reaction to the cue is preferably the result of some degree of training or education such that the subject is aware of what a particular cue means, and can react substantially instantaneously and without deliberation or pause to recollect the best reaction to the particular cue. Given that the system is intended to be a continuous monitoring and cueing system, once a cue is provided, the system returns 2440 to the movement measurement step 2405. More accurately, the system will have been measuring movement the entire time, but for purposes of clarification and given that the prediction or detection and cueing steps are all performed in real-time, it can be visualized as a separate step for the system to return from providing a cue to measuring the subject's movement as a result of the cue. Embodiments such as depicted further comprise a treatment, therapy or assistance device that can supplement the cueing system to help the subject in the therapy process for correcting impaired, symptomatic or unsafe or undesirable movement. Preferably, the treatment, therapy or assistance device is only employed when absolutely necessary to help improve function and prevent or mitigate injury to the subject. Such circumstances might arise if the system predicts or detects a severely impaired or symptomatic movement that could cause harm before the subject could react to a cue, or if successive cues provide no improvement or are ignored leading to persisting or worsening impairment, symptoms, or unsafe or undesirable movement. In such cases, the algorithm preferably sends a signal 2445 to the treatment, therapy or assistance device activating the device to provide a corresponding treatment, therapy or assistance 2450 to the subject. Such treatment, therapy or assistance can be of any type described herein (e.g., DBS, FES, drug or medication) or any other currently known or later developed treatment, therapy or assistance useful with subjects using the present invention. The treatment, therapy or assistance is intended to help the subject address impaired, symptomatic or unsafe or undesirable movement when a cue and resulting knowledge of the subject is insufficient. Once again, after the treatment, therapy or assistance is provided 2450, the system returns 2440, or rather maintains, the continuous measuring of the subject's movement 2405.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of providing real-time rehabilitation and training or improving quality and safety of a subject's movement comprising steps of:

providing a portable therapy device to the subject, the therapy device comprising at least two sensors, each sensor having a signal related to the subject's movement and at least one sensor for measuring the subject's motion related to the subject's gait, during activities of daily living, a processor comprising an algorithm and an output, and a cueing or stimulus device, the at least one sensor adapted to be attached to or worn on or about the subject's wrist;

measuring the subject's movement with the at least one sensor substantially continuously to acquire movement data while the subject is performing activities of daily living;

extracting, with the processor, at least one kinematic feature from the measured movement data, the at least one kinematic feature related to the subject's balance or posture;

analyzing, in real-time, the at least one kinematic feature with the algorithm to predict or detect the occurrence of a balance or posture impairment, the prediction or determination being made at least in part based on identification of the kinematic feature of circumduction compensation strategy which is identified at least in part by an abduction angle greater than 7 degrees;

transmitting the output of the algorithm to a cueing or stimulus device; and providing with the cueing or stimulus device a cue or stimulus to the subject based on the prediction or determination in real-time, wherein the cue or stimulus is adapted to notify the subject of the prediction or determination and to allow the subject to react accordingly to prevent or correct the predicted or detected balance or posture impairment.

2. The method of claim 1, wherein the portable therapy device is a smartphone that comprises at least the processor and algorithm and cueing or stimulus device, and the smartphone receives the signal from the at least one sensor, analyzes the movement data to predict or detect the occurrence of a balance or posture impairment, and provides the cue or stimulus based on the prediction or determination.

3. The method of claim 2, wherein the portable therapy device comprises at least one additional sensor, the at least one additional sensor adapted to be on or in the smartphone, the and the at least one sensor adapted to be attached to or worn on or about the subject's wrist is further adapted to be in wired or wireless communication with the smartphone.

4. The method of claim 1, wherein the portable therapy device comprises at least one additional sensor for measuring the subject's motion related to the subject's balance or posture, and at least two kinematic features are extracted and analyzed to predict or determine the occurrence of a balance impairment, at least one kinematic feature being gait asymmetry as measured a symmetry ratio (SR) and a prediction or detection of a balance or posture impairment is made when the SR is greater than 1.1.

5. The method of claim 1, wherein the portable therapy device is adapted to detect the subject's environment or location and the cue or stimulus provided is automatically adapted based on the detected environment or location by altering the type of cue or stimulus provided.

6. A method of providing real-time rehabilitation and training or improving quality and safety of a subject's movement comprising steps of:
providing a portable therapy device to the subject, the therapy device comprising at least two sensors, at least one sensor having a signal related to the subject's balance or stability and at least one sensor for measuring the subject's motion related to the subject's gait, during activities of daily living, a processor comprising an algorithm and an output, and a cueing or stimulus device, the at least one sensor adapted to be attached to or worn on or about the subject's wrist;
measuring the subject's balance or postural stability with the at least one sensor substantially continuously to acquire movement data while the subject is performing activities of daily living;
extracting, with the processor, at least one kinematic feature from the measured movement data, the at least one kinematic feature related to the subject's balance or posture;
analyzing, in real-time, the at least one kinematic feature with the processor and algorithm to predict or detect imbalance or instability of the subject, the prediction or determination being made at least in part based on identification of the kinematic feature of circumduction compensation strategy which is identified at least in part by an abduction angle greater than about 7 degrees;
transmitting the output of the algorithm to a cueing or stimulus device; and
providing with the cueing or stimulus device a cue or stimulus to the subject based on the prediction or determination in real-time,
wherein the cue or stimulus is adapted to notify the subject of the prediction or determination and to allow the subject to react accordingly to prevent or correct the predicted or detected imbalance or instability.

7. The method of claim 6, wherein the portable therapy device is a smartphone that comprises at least the processor and algorithm and cueing or stimulus device, and the smartphone receives the signal from the at least one sensor, analyzes the movement data to predict or detect the occurrence of a balance or posture impairment, and provides the cue or stimulus based on the prediction or determination.

8. The method of claim 7, wherein the portable therapy device comprises at least one additional sensor, at least one additional sensor adapted to be on or in the smartphone and the at least one sensor having a signal related to the subject's balance or stability further adapted to be in wired or wireless communication with the smartphone.

9. The method of claim 6, wherein the portable therapy device comprises at least one additional sensor for measuring the subject's motion related to the subject's balance or posture, and at least two kinematic features are extracted and analyzed to predict or determine the occurrence of a balance impairment, at least one kinematic feature being gait asymmetry as measured a symmetry ratio (SR) and a prediction or detection of a balance or posture impairment is made when the SR is greater than 1.1.

10. The method of claim 6, wherein the portable therapy device is adapted to detect the subject's environment or location and the cue or stimulus provided is automatically adapted based on the detected environment or location by altering the type of cue or stimulus provided.

11. A portable therapy system for real-time rehabilitation and training or to improve the quality and safety of a subject's movement comprising:
at least one sensor adapted to be worn or attached to a portion of the subject's body below the subject's neck and to measure a subject's movement during activities of daily living, the at least one sensor having a signal related to the subject's voluntary or involuntary movement;
a processor comprising an algorithm, the processor adapted to at least in part extract at least one kinematic feature from measured movement, the at least one kinematic feature related to the subject's balance or posture, the algorithm adapted to, at least in part, analyze, in real-time, the at least one kinematic feature to predict or detect the occurrence of a balance or posture impairment and provide an output corresponding to the prediction or determination, the prediction or determination being at least in part based on identification of the kinematic feature of circumduction compensation strategy which is identified at least in part by an abduction angle greater than about 7 degrees;
a cueing or stimulus device adapted to receive the output from the algorithm and provide at least one cue or stimulus to the subject based at least in part on the output of the algorithm in real-time,
wherein the at least one cue or stimulus is adapted to notify the subject wearing the portable therapy system of the prediction or determination and allow the subject to react accordingly to prevent or correct the predicted or detected balance or posture impairment.

12. The system of claim 11, wherein the portable therapy device is a smartphone that comprises at least the processor and algorithm and cueing or stimulus device, and the smartphone receives the signal from the at least one sensor, analyzes the movement data to predict or detect the occurrence of a balance or posture impairment, and provides the cue or stimulus based on the prediction or determination.

13. The system of claim 12, wherein the portable therapy device comprises at least one additional sensor, at least one additional sensor adapted to be on or in the smartphone and the at least one sensor adapted to be worn or attached to a portion of the subject's body below the subject's neck and to measure a subject's movement-further adapted to be in wired or wireless communication with the smartphone.

14. The system of claim 11, wherein at least two kinematic features are extracted and analyzed to predict or determine the occurrence of a balance impairment, at least one kinematic feature being gait asymmetry as measured a symmetry ratio (SR) and a prediction or detection of a balance or posture impairment is made when the SR is greater than 1.1.

* * * * *